United States Patent [19]

Little, II et al.

[11] Patent Number: 5,627,153
[45] Date of Patent: May 6, 1997

[54] ANTI-FUNGAL METHODS AND MATERIALS

[75] Inventors: Roger G. Little, II, Benicia; Edward Lim, Walnut Creek; Patrick J. Scannon, San Francisco; Lewis J. Lambert, Jr., Fremont, all of Calif.

[73] Assignee: Xoma Corporation, Berkeley, Calif.

[21] Appl. No.: 372,105

[22] Filed: Jan. 13, 1995

Related U.S. Application Data

[63] Continuation-in-part of Ser. No. 273,540, Jul. 11, 1994, abandoned, which is a continuation-in-part of Ser. No. 209,762, Mar. 11, 1994, which is a continuation-in-part of Ser. No. 183,222, Jan. 14, 1994, abandoned.

[51] Int. Cl.$^6$ .............................. A61K 38/00; C07K 1/00
[52] U.S. Cl. .............................. 514/12; 514/21; 530/324; 530/350; 530/380
[58] Field of Search ................... 514/12, 21; 530/350, 530/324, 380

[56] References Cited

U.S. PATENT DOCUMENTS

| | | | |
|---|---|---|---|
| 5,087,569 | 2/1992 | Gabay et al. | 435/212 |
| 5,089,274 | 2/1992 | Marra et al. | 424/534 |
| 5,126,257 | 6/1992 | Gabay et al. | 435/212 |
| 5,171,739 | 12/1992 | Scott | 514/12 |
| 5,198,541 | 3/1993 | Elsbach et al. | 435/69.1 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |
| 5,420,019 | 5/1995 | Theofan et al. | 435/69.1 |
| 5,447,913 | 9/1995 | Ammons et al. | 514/12 |

FOREIGN PATENT DOCUMENTS

| | | |
|---|---|---|
| WO90/09183 | 8/1990 | WIPO. |
| WO92/03535 | 3/1992 | WIPO. |
| WO92/09621 | 6/1992 | WIPO. |
| WO93/05797 | 4/1993 | WIPO. |
| WO93/06228 | 4/1993 | WIPO. |
| WO93/23434 | 11/1993 | WIPO. |
| WO93/23540 | 11/1993 | WIPO. |
| WO94/17819 | 8/1994 | WIPO. |
| WO94/18323 | 8/1994 | WIPO. |
| WO94/20128 | 9/1994 | WIPO. |
| WO94/20129 | 9/1994 | WIPO. |
| WO94/20532 | 9/1994 | WIPO. |

OTHER PUBLICATIONS

Davies, "Inactivation of Antibiotics and the Dissemination of Resistance Genes", *Science*, 264:375–381 (Apr. 15, 1994).

Eliopoulos and Moellering, "Antimicrobial Combinations", in *Antibiotics in Laboratory Medicine*, 3rd ed., pp. 432–492, (Lorian ed., Baltimore, MD) (1991).

Elsbach, "Antibiotics from within: Antibacterials from Human and Animal Sources", *Trends. Biotech*, 8(1):26–30 (Jan. 1990).

Elsbach et al., "Separation and Purification of a Potent Bactericidal/Permeability-Increasing Protein and a Closely Associated Phospholipase $A_2$ from Rabbit Polymorphonuclear Leukocytes," *J. Biol. Chem.*, 254:11000–11009 (1979).

Elsbach and Weiss, "Oxygen-Independent Antimicrobial Systems of Phagocytes," in *Inflammation: Basic Principles and Clinical Correlates*, pp. 603–636, (Gallin et al eds., Raven Press, Ltd.) (1992).

Elsbach and Weiss, "Oxygen-Independent Bactericidal Systems of Polymorphonuclear Leukocytes", in *Advances in Inflammation Research*, pp. 95–113, (Weissmann ed., Raven Press) (1981).

Gabay, "Ubiquitous Natural Antibiotics", *Science*, 264:373–374 (Apr. 15, 1994).

Gazzano–Santoro et al., "High-Affinity Binding of the Bactericidal/Permeability-Increasing Protein and a Recombinant Amino-Terminal Fragment to the Lipid A Region of Lipopolysaccharide", *Infect. Immun.*, 60(11):4754–4761 (Nov. 1992).

Georgopapadakou and Walsh, "Human Mycoses: Drugs and Targets for Emerging Pathogens", *Science*, 264:371–373 (Apr. 15, 1994).

Gray et al., "Cloning of the cDNA of a Human Neutrophil Bactericidal Protein", *J. Biol. Chem.*, 264(16):9505–9509 (Jun. 5, 1989).

Kanbe et al., "Evidence that Mannans of *Candida albicans* Are Responsible for Adherence of Yeast Forms to Spleen and Lymph Node Tissue", *Infect. Immun.*, 61(6):2578–2584 (Jun. 1993).

Klotz and Smith, "Glycosaminoglycans Inhibit *Candida albicans* Adherence to Extracellular Matrix Proteins", *FEMS Microbiology Letters*, 99:205–208 (1992).

Levy et al., "Antibacterial 15–kDa Protein Isoforms (p15s) are Members of a Novel Family of Leukocyte Proteins", *J. Biol. Chem.*, 268(8):6058–6068 (Mar. 16, 1993).

Mannion et al., "Preferential Binding of the Neutrophil Cytoplasmic Granule–Derived Bactericidal/Permeability Increasing Protein to Target Bacteria", *J. Clin. Invest.*, 142(8):2807–2812 (Apr. 15, 1989).

Mannion et al., "Separation of Sublethal and Lethal Effects of Polymorphonuclear Leukocytes on *Escherichia coli*", *J. Clin. Invest.*, 86:631–641 (Aug. 1990).

Mannion et al., "Separation of Sublethal and Lethal Effects of the Bactericidal/Permeability Increasing Protein on *Escherichia coli*", *J. Clin. Invest.*, 85:853–860 (Mar. 1990).

Ooi et al., "A 25–kDa $NH_2$–terminal Fragment Carries All the Antibacterial Activities of the Human Neutrophil 60–kDa Bactericidal/Permeability-Increasing Protein", *J. Biol. Chem.*, 262(31):14891–14894 (1987).

(List continued on next page.)

*Primary Examiner*—Cecilia J. Tsang
*Assistant Examiner*—Abdel A. Mohamed
*Attorney, Agent, or Firm*—Marshall, O'Toole, Gerstein, Murray & Borun

[57] ABSTRACT

The present invention relates to methods for treating fungal infection comprising administering to a subject suffering from a fungal infection a bactericidal/permeability-inducing (BPI) protein product.

16 Claims, 8 Drawing Sheets

OTHER PUBLICATIONS

Ooi et al., "Endotoxin–neutralizing Properties of the 25 kD N–Terminal Fragment and a Newly Isolated 30 kD C–Terminal Fragment of the 55–60 kD Bactericidal/Permeability–Increasing Protein of Human Neutrophils", *J. Exp. Med.*, 174:649–655 (Sep. 1991).

Ooi et al., "Isolation of Two Isoforms of a Novel 15–kDa Protein from Rabbit Polymorphonuclear Leukocytes that Modulate the Antibacterial Actions of Other Leukocyte Proteins," *J. Biol. Chem.*, 265:15956–15962 (1990).

Sternberg, "The Emerging Fungal Threat", *Science*, 266(9):1632–1634 (Dec. 1994).

Stratton, "In Vitro Testing: Correlations Between Bacterial Susceptibility, Body Fluid Levels and Effectiveness of Antibacterial Therapy", in *Antibiotics in Laboratory Medicine*, pp. 849–879 (Lorian ed., Williams & Wilkins) (1991).

Veld et al., "Effects of the Bactericidal/Permeability–Increasing Protein of Polymorphonuclear Leukocytes on Isolated Bacterial Cytoplasmic Membrane Vesicles", *Infect. Immun.*, 56(5):1203–1208 (May 1988).

Weiss and Olsson, "Cellular and Subcellular Localization of the Bactericidal/Permeability–Increasing Protein of Neutrophils", *Blood*, 69(2):652–659 (Feb. 1987).

Weiss et al., "Human Bactericidal/Permeability–Increasing Protein and a Recombinant $NH_2$–Terminal Fragment Cause Killing of Serum–resistant Gram–negative Bacteria in Whole Blood and Inhibit Tumor Necrosis Factor Release Induced by the Bacteria", *J. Clin. Invest.*, 90:1122–1130 (Sep. 1992).

Weiss et al., "Resistance of Gram–negative Bacteria to Purified Bactericidal Leukocyte Proteins", *J. Clin. Invest.*, 65:619–628 (Mar. 1980).

Weiss et al., "The Role of Lipopolysaccharides in the Action of the Bactericidal/Permeability–Increasing Neutrophil Protein on the Bacterial Envelope", *J. Immunol.*, 132(6):3109–3115 (Jun. 1984).

SEQUENCE LISTING ( 1 ) GENERAL INFORMATION:

( i i i ) NUMBER OF SEQUENCES: 227

( 2 ) INFORMATION FOR SEQ ID NO:1:

( i ) SEQUENCE CHARACTERISTICS:
  ( A ) LENGTH: 29 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "Domain I"

( x i ) SEQUENCE DESCRIPTION: SEQ ID NO:1:

```
Ala  Ser  Gln  Gln  Gly  Thr  Ala  Ala  Leu  Gln  Lys  Glu  Leu  Lys  Arg  Ile
 1              5                        10                           15

Lys  Ile  Pro  Asp  Tyr  Ser  Asp  Ser  Phe  Lys  Ile  Lys  His
              20                        25
```

( 2 ) INFORMATION FOR SEQ ID NO:2:

( i ) SEQUENCE CHARACTERISTICS:
  ( A ) LENGTH: 30 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.14"

( x i ) SEQUENCE DESCRIPTION: SEQ ID NO:2:

```
Gly  Thr  Ala  Ala  Leu  Gln  Lys  Glu  Leu  Lys  Arg  Ile  Lys  Ile  Pro  Asp
 1              5                        10                           15

Tyr  Ser  Asp  Ser  Phe  Lys  Ile  Lys  His  Leu  Gly  Lys  Gly  His
              20                        25                      30
```

( 2 ) INFORMATION FOR SEQ ID NO:3:

( i ) SEQUENCE CHARACTERISTICS:
  ( A ) LENGTH: 22 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.4"

( x i ) SEQUENCE DESCRIPTION: SEQ ID NO:3:

```
        Leu  Gln  Lys  Glu  Leu  Lys  Arg  Ile  Lys  Ile  Pro  Asp  Tyr  Ser  Asp  Ser
        1                  5                            10                           15

Phe  Lys  Ile  Lys  His  Leu
                       20
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.1"

( x i ) SEQUENCE DESCRIPTION: SEQ ID NO:4:

```
        Gln  Gln  Gly  Thr  Ala  Ala  Leu  Gln  Lys  Glu  Leu  Lys  Arg  Ile  Lys
        1                  5                            10                      15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.54"

( x i ) SEQUENCE DESCRIPTION: SEQ ID NO:5:

```
        Gly  Thr  Ala  Ala  Leu  Gln  Lys  Glu  Leu  Lys  Arg  Ile  Lys  Ile  Pro
        1                  5                            10                      15
```

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Domain II"

( x i ) SEQUENCE DESCRIPTION: SEQ ID NO:6:

```
        Ser  Ser  Gln  Ile  Ser  Met  Val  Pro  Asn  Val  Gly  Leu  Lys  Phe  Ser  Ile
        1                  5                            10                           15

Ser  Asn  Ala  Asn  Ile  Lys  Ile  Ser  Gly  Lys  Trp  Lys  Ala  Gln  Lys  Arg
                       20                  25                           30

Phe  Leu  Lys
                  35
```

( 2 ) INFORMATION FOR SEQ ID NO:7:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:

( A ) NAME/KEY: misc_feature
( D ) OTHER INFORMATION: "XMP.2"

( x i ) SEQUENCE DESCRIPTION: SEQ ID NO:7:

```
Ile  Lys  Ile  Ser  Gly  Lys  Trp  Lys  Ala  Gln  Lys  Arg  Phe  Leu  Lys
1              5                        10                       15
```

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.8"

( x i ) SEQUENCE DESCRIPTION: SEQ ID NO:8:

```
Lys  Trp  Lys  Ala  Gln  Lys  Arg  Phe  Leu  Lys
1              5                        10
```

( 2 ) INFORMATION FOR SEQ ID NO:9:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.58"

( x i ) SEQUENCE DESCRIPTION: SEQ ID NO:9:

```
Cys  Ile  Lys  Ile  Ser  Gly  Lys  Trp  Lys  Ala  Gln  Lys  Arg  Phe  Leu  Lys
1              5                        10                       15
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.65 oxidized"

( x i ) SEQUENCE DESCRIPTION: SEQ ID NO:10:

```
Cys  Ile  Lys  Ile  Ser  Gly  Lys  Trp  Lys  Ala  Gln  Lys  Arg  Phe  Leu  Lys
1              5                        10                       15

Cys
```

( 2 ) INFORMATION FOR SEQ ID NO:11:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.3"

( x i ) SEQUENCE DESCRIPTION: SEQ ID NO:11:

Asn Val Gly Leu Lys Phe Ser Ile Ser Asn Ala Asn Ile Lys Ile Ser
1               5                   10                  15

Gly Lys Trp Lys Ala Gln Lys Arg Phe Leu Lys
            20                  25

( 2 ) INFORMATION FOR SEQ ID NO:12:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "Domain III"

( x i ) SEQUENCE DESCRIPTION: SEQ ID NO:12:

Val His Val His Ile Ser Lys Ser Lys Val Gly Trp Leu Ile Gln Leu
1               5                   10                  15

Phe His Lys Lys Ile Glu Ser Ala Leu Arg Asn Lys
            20                  25

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.11"

( x i ) SEQUENCE DESCRIPTION: SEQ ID NO:13:

Lys Ser Lys Val Trp Leu Ile Gln Leu Phe His Lys Lys
1               5                   10

( 2 ) INFORMATION FOR SEQ ID NO:14:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.12"

( x i ) SEQUENCE DESCRIPTION: SEQ ID NO:14:

Ser Val His Val His Ile Ser Lys Ser Lys Val Gly Trp Leu Ile Gln
1               5                   10                  15

Leu Phe His Lys Lys Ile Glu Ser Ala Leu Arg Asn Lys
            20                  25

( 2 ) INFORMATION FOR SEQ ID NO:15:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.13"

( x i ) SEQUENCE DESCRIPTION: SEQ ID NO:15:

```
Lys Ser Lys Val Gly Trp Leu Ile Gln Leu Phe His Lys Lys
1                5                   10
```

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.15"

( x i ) SEQUENCE DESCRIPTION: SEQ ID NO:16:

```
Ala Lys Ile Ser Gly Lys Trp Lys Ala Gln Lys Arg Phe Leu Lys
1                5                   10                  15
```

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.16"

( x i ) SEQUENCE DESCRIPTION: SEQ ID NO:17:

```
Ile Ala Ile Ser Gly Lys Trp Lys Ala Gln Lys Arg Phe Leu Lys
1                5                   10                  15
```

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.17"

( x i ) SEQUENCE DESCRIPTION: SEQ ID NO:18:

```
Ile Lys Ala Ser Gly Lys Trp Lys Ala Gln Lys Arg Phe Leu Lys
1                5                   10                  15
```

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature (D) OTHER INFORMATION: "XMP.18"

(xi) SEQUENCE DESCRIPTION: SEQ ID NO:19:

```
Ile Lys Ile Ala Gly Lys Trp Lys Ala Gln Lys Arg Phe Leu Lys
1               5                   10                  15
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.19"

(xi) SEQUENCE DESCRIPTION: SEQ ID NO:20:

```
Ile Lys Ile Ser Ala Lys Trp Lys Ala Gln Lys Arg Phe Leu Lys
1               5                   10                  15
```

(2) INFORMATION FOR SEQ ID NO:21:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.20"

(xi) SEQUENCE DESCRIPTION: SEQ ID NO:21:

```
Ile Lys Ile Ser Gly Ala Trp Lys Ala Gln Lys Arg Phe Leu Lys
1               5                   10                  15
```

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.21"

(xi) SEQUENCE DESCRIPTION: SEQ ID NO:22:

```
Ile Lys Ile Ser Gly Lys Ala Lys Ala Gln Lys Arg Phe Leu Lys
1               5                   10                  15
```

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.22"

(xi) SEQUENCE DESCRIPTION: SEQ ID NO:23:

```
Ile Lys Ile Ser Gly Lys Trp Ala Ala Gln Lys Arg Phe Leu Lys
1               5                   10                  15
```

( 2 ) INFORMATION FOR SEQ ID NO:24:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.23"

( x i ) SEQUENCE DESCRIPTION: SEQ ID NO:24:

```
Ile Lys Ile Ser Gly Lys Trp Lys Ala Ala Lys Arg Phe Leu Lys
1               5                   10                  15
```

( 2 ) INFORMATION FOR SEQ ID NO:25:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.24"

( x i ) SEQUENCE DESCRIPTION: SEQ ID NO:25:

```
Ile Lys Ile Ser Gly Lys Trp Lys Ala Gln Ala Arg Phe Leu Lys
1               5                   10                  15
```

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.25"

( x i ) SEQUENCE DESCRIPTION: SEQ ID NO:26:

```
Ile Lys Ile Ser Gly Lys Trp Lys Ala Gln Lys Ala Phe Leu Lys
1               5                   10                  15
```

( 2 ) INFORMATION FOR SEQ ID NO:27:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.26"

( x i ) SEQUENCE DESCRIPTION: SEQ ID NO:27:

```
Ile Lys Ile Ser Gly Lys Trp Lys Ala Gln Lys Arg Ala Leu Lys
1               5                   10                  15
```

( 2 ) INFORMATION FOR SEQ ID NO:28:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.27"

( x i ) SEQUENCE DESCRIPTION: SEQ ID NO:28:

```
Ile  Lys  Ile  Ser  Gly  Lys  Trp  Lys  Ala  Gln  Lys  Arg  Phe  Ala  Lys
1                   5                        10                       15
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.28"

( x i ) SEQUENCE DESCRIPTION: SEQ ID NO:29:

```
Ile  Lys  Ile  Ser  Gly  Lys  Trp  Lys  Ala  Gln  Lys  Arg  Phe  Leu  Ala
1                   5                        10                       15
```

( 2 ) INFORMATION FOR SEQ ID NO:30:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.59"

( x i ) SEQUENCE DESCRIPTION: SEQ ID NO:30:

```
Ile  Lys  Ile  Ser  Gly  Ala  Trp  Ala  Ala  Gln  Lys  Arg  Phe  Leu  Lys
1                   5                        10                       15
```

( 2 ) INFORMATION FOR SEQ ID NO:31:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.45"

( x i ) SEQUENCE DESCRIPTION: SEQ ID NO:31:

```
Ile  Lys  Ile  Ser  Gly  Lys  Trp  Lys  Ala  Ala  Ala  Arg  Phe  Leu  Lys
1                   5                        10                       15
```

( 2 ) INFORMATION FOR SEQ ID NO:32:

( i ) SEQUENCE CHARACTERISTICS:
        ( A ) LENGTH: 15 amino acids (B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.60"

(xi) SEQUENCE DESCRIPTION: SEQ ID NO:32:

```
Ile Ala Ile Ser Gly Lys Trp Lys Ala Gln Lys Arg Phe Leu Ala
1               5                   10                  15
```

(2) INFORMATION FOR SEQ ID NO:33:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.31"

(xi) SEQUENCE DESCRIPTION: SEQ ID NO:33:

```
Ala Ser Lys Val Gly Trp Leu Ile Gln Leu Phe His Lys Lys
1               5                   10
```

(2) INFORMATION FOR SEQ ID NO:34:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.32"

(xi) SEQUENCE DESCRIPTION: SEQ ID NO:34:

```
Lys Ala Lys Val Gly Trp Leu Ile Gln Leu Phe His Lys Lys
1               5                   10
```

(2) INFORMATION FOR SEQ ID NO:35:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.33"

(xi) SEQUENCE DESCRIPTION: SEQ ID NO:35:

```
Lys Ser Ala Val Gly Trp Leu Ile Gln Leu Phe His Lys Lys
1               5                   10
```

(2) INFORMATION FOR SEQ ID NO:36:

(i) SEQUENCE CHARACTERISTICS:
(A) LENGTH: 14 amino acids
(B) TYPE: amino acid
(D) TOPOLOGY: linear (ii) MOLECULE TYPE: peptide ( i x ) FEATURE:
    ( A ) NAME/KEY: misc_feature
    ( D ) OTHER INFORMATION: "XMP.34"

( x i ) SEQUENCE DESCRIPTION: SEQ ID NO:36:

```
Lys  Ser  Lys  Ala  Gly  Trp  Leu  Ile  Gln  Leu  Phe  His  Lys  Lys
1              5                        10
```

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.35"

( x i ) SEQUENCE DESCRIPTION: SEQ ID NO:37:

```
Lys  Ser  Lys  Val  Ala  Trp  Leu  Ile  Gln  Leu  Phe  His  Lys  Lys
1              5                        10
```

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.36"

( x i ) SEQUENCE DESCRIPTION: SEQ ID NO:38:

```
Lys  Ser  Lys  Val  Gly  Ala  Leu  Ile  Gln  Leu  Phe  His  Lys  Lys
1              5                        10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.37"

( x i ) SEQUENCE DESCRIPTION: SEQ ID NO:39:

```
Lys  Ser  Lys  Val  Gly  Trp  Ala  Ile  Gln  Leu  Phe  His  Lys  Lys
1              5                        10
```

( 2 ) INFORMATION FOR SEQ ID NO:40:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.38"

( x i ) SEQUENCE DESCRIPTION: SEQ ID NO:40:

Lys Ser Lys Val Gly Trp Leu Ala Gln Leu Phe His Lys Lys
1               5                   10

( 2 ) INFORMATION FOR SEQ ID NO:41:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.39"

( x i ) SEQUENCE DESCRIPTION: SEQ ID NO:41:

Lys Ser Lys Val Gly Trp Leu Ile Ala Leu Phe His Lys Lys
1               5                   10

( 2 ) INFORMATION FOR SEQ ID NO:42:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.40"

( x i ) SEQUENCE DESCRIPTION: SEQ ID NO:42:

Lys Ser Lys Val Gly Trp Leu Ile Gln Ala Phe His Lys Lys
1               5                   10

( 2 ) INFORMATION FOR SEQ ID NO:43:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.41"

( x i ) SEQUENCE DESCRIPTION: SEQ ID NO:43:

Lys Ser Lys Val Gly Trp Leu Ile Gln Leu Ala His Lys Lys
1               5                   10

( 2 ) INFORMATION FOR SEQ ID NO:44:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.42"

( x i ) SEQUENCE DESCRIPTION: SEQ ID NO:44:

Lys Ser Lys Val Gly Trp Leu Ile Gln Leu Phe Ala Lys Lys 1          5          10

( 2 ) INFORMATION FOR SEQ ID NO:45:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.43"

( x i ) SEQUENCE DESCRIPTION: SEQ ID NO:45:

Lys Ser Lys Val Gly Trp Leu Ile Gln Leu Phe His Ala Lys
1               5                   10

( 2 ) INFORMATION FOR SEQ ID NO:46:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.44"

( x i ) SEQUENCE DESCRIPTION: SEQ ID NO:46:

Lys Ser Lys Val Gly Trp Leu Ile Gln Leu Phe His Lys Ala
1               5                   10

( 2 ) INFORMATION FOR SEQ ID NO:47:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.56"

( x i ) SEQUENCE DESCRIPTION: SEQ ID NO:47:

Ile Lys Ile Ser Gly Lys Trp Lys Ala Lys Gln Arg Phe Leu Lys
1               5                   10                  15

( 2 ) INFORMATION FOR SEQ ID NO:48:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.61"

( x i ) SEQUENCE DESCRIPTION: SEQ ID NO:48:

Ile Lys Ile Ser Gly Lys Phe Lys Ala Gln Lys Arg Phe Leu Lys
1               5                   10                  15

( 2 ) INFORMATION FOR SEQ ID NO:49:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.66"

( i x ) FEATURE:
    ( A ) NAME/KEY: Modified-site
    ( B ) LOCATION: 7
    ( D ) OTHER INFORMATION: /label= D- Trp
        / note= "The amino acid at position 7 is
        D- tryptophan"

( x i ) SEQUENCE DESCRIPTION: SEQ ID NO:49:

```
Ile  Lys  Ile  Ser  Gly  Lys  Trp  Lys  Ala  Gln  Lys  Arg  Phe  Leu  Lys
1              5                        10                       15
```

( 2 ) INFORMATION FOR SEQ ID NO:50:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.67"

( i x ) FEATURE:
        ( A ) NAME/KEY: Modified-site
        ( B ) LOCATION: 6..8
        ( D ) OTHER INFORMATION: /label= Substituted-Ala
            / note= "The alanine at position 7 is
            beta-1- naphthyl-substituted"

( x i ) SEQUENCE DESCRIPTION: SEQ ID NO:50:

```
Ile  Lys  Ile  Ser  Gly  Lys  Ala  Lys  Ala  Gln  Lys  Arg  Phe  Leu  Lys
1              5                        10                       15
```

( 2 ) INFORMATION FOR SEQ ID NO:51:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.9"

( x i ) SEQUENCE DESCRIPTION: SEQ ID NO:51:

```
Lys  Arg  Phe  Leu  Lys  Lys  Trp  Lys  Ala  Gln  Lys  Arg  Phe  Leu  Lys
1              5                        10                       15
```

( 2 ) INFORMATION FOR SEQ ID NO:52:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:

(A) NAME/KEY: misc_feature
(D) OTHER INFORMATION: "XMP.30"

(xi) SEQUENCE DESCRIPTION: SEQ ID NO:52:

Lys Trp Lys Ala Gln Lys Arg Phe Leu Lys Lys Ser Lys Val Gly Trp
1               5                   10                  15
Leu Ile Gln Leu Phe His Lys Lys
            20

(2) INFORMATION FOR SEQ ID NO:53:

(i) SEQUENCE CHARACTERISTICS:
      (A) LENGTH: 29 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.63"

(xi) SEQUENCE DESCRIPTION: SEQ ID NO:53:

Ile Lys Ile Ser Gly Lys Trp Lys Ala Gln Lys Arg Phe Leu Lys Lys
1               5                   10                  15
Ser Lys Val Gly Trp Leu Ile Gln Leu Phe His Lys Lys
            20                      25

(2) INFORMATION FOR SEQ ID NO:54:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.7"

(xi) SEQUENCE DESCRIPTION: SEQ ID NO:54:

Lys Trp Lys Ala Gln Lys Arg Phe Leu Lys Lys Trp Lys Ala Gln Lys
1               5                   10                  15
Arg Phe Leu Lys
            20

(2) INFORMATION FOR SEQ ID NO:55:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.10.1"

(xi) SEQUENCE DESCRIPTION: SEQ ID NO:55:

Lys Arg Phe Leu Lys Lys Trp Lys Ala Gln Lys Arg Phe Leu Lys Lys
1               5                   10                  15
Trp Lys Ala Gln Lys Arg Phe Leu Lys
            20                  25

(2) INFORMATION FOR SEQ ID NO:56:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.29"

( x i ) SEQUENCE DESCRIPTION: SEQ ID NO:56:

```
Lys Ser Lys Val Gly Trp Leu Ile Gln Leu Phe His Lys Lys Lys Ser
1               5                   10                  15
Lys Val Gly Trp Leu Ile Gln Leu Phe His Lys Lys
                20                  25
```

( 2 ) INFORMATION FOR SEQ ID NO:57:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.46"

( x i ) SEQUENCE DESCRIPTION: SEQ ID NO:57:

```
Lys Trp Lys Ala Ala Ala Arg Phe Leu Lys Lys Trp Lys Ala Gln Lys
1               5                   10                  15
Arg Phe Leu Lys
                20
```

( 2 ) INFORMATION FOR SEQ ID NO:58:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.47"

( x i ) SEQUENCE DESCRIPTION: SEQ ID NO:58:

```
Lys Trp Lys Ala Gln Lys Arg Phe Leu Lys Lys Trp Lys Ala Ala Ala
1               5                   10                  15
Arg Phe Leu Lys
                20
```

( 2 ) INFORMATION FOR SEQ ID NO:59:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.48"

( x i ) SEQUENCE DESCRIPTION: SEQ ID NO:59:

```
Lys Trp Lys Ala Ala Ala Arg Phe Leu Lys Lys Trp Lys Ala Ala Ala
```

Arg Phe Leu Lys
20

( 2 ) INFORMATION FOR SEQ ID NO:60:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.69"

( x i ) SEQUENCE DESCRIPTION: SEQ ID NO:60:

Lys Trp Lys Ala Ala Ala Arg Phe Leu Lys Lys Trp Lys Ala Ala Ala
1               5                   10                  15

Arg Phe Leu Lys Lys Trp Lys Ala Ala Arg Phe Leu Lys
        20                  25                  30

( 2 ) INFORMATION FOR SEQ ID NO:61:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.55"

( x i ) SEQUENCE DESCRIPTION: SEQ ID NO:61:

Gly Trp Leu Ile Gln Leu Phe His Lys Lys Ile Glu Ser Ala Leu Arg
1               5                   10                  15

Asn Lys Met Asn Ser
        20

( 2 ) INFORMATION FOR SEQ ID NO:62:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.73"

( x i ) SEQUENCE DESCRIPTION: SEQ ID NO:62:

Ile Lys Ile Ser Gly Lys Trp Lys Ala Gln Phe Arg Phe Leu Lys
1               5                   10                  15

( 2 ) INFORMATION FOR SEQ ID NO:63:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature ( D ) OTHER INFORMATION: "XMP.70"

( i x ) FEATURE:
    ( A ) NAME/KEY: Modified-site
    ( B ) LOCATION: 8..10
    ( D ) OTHER INFORMATION: /label= Substituted-Ala
        / note= "The alanine at position 7 is
        beta-3- pyridyl-substituted"

( x i ) SEQUENCE DESCRIPTION: SEQ ID NO:63:

Ile Lys Ile Ser Gly Lys Ala Lys Ala Gln Lys Arg Phe Leu Lys
1               5                   10                  15

( 2 ) INFORMATION FOR SEQ ID NO:64:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.71"

( i x ) FEATURE:
        ( A ) NAME/KEY: Modified-site
        ( B ) LOCATION: 13..15
        ( D ) OTHER INFORMATION: /label= Substituted-Ala
            / note= "The alanine at position 13 is
            beta-3- pyridyl-substituted"

( x i ) SEQUENCE DESCRIPTION: SEQ ID NO:64:

Ile Lys Ile Ser Gly Lys Trp Lys Ala Gln Lys Arg Ala Leu Lys
1               5                   10                  15

( 2 ) INFORMATION FOR SEQ ID NO:65:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.10.2"

( x i ) SEQUENCE DESCRIPTION: SEQ ID NO:65:

Gln Lys Arg Phe Leu Lys Lys Trp Lys Ala Gln Lys Arg Phe Leu Lys
1               5                   10                  15

Lys Trp Lys Ala Gln Lys Arg Phe Leu Lys
                20                  25

( 2 ) INFORMATION FOR SEQ ID NO:66:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.72"

( i x ) FEATURE:
        ( A ) NAME/KEY: Modified-site
        ( B ) LOCATION: 1..3
        ( D ) OTHER INFORMATION: /label= D- alanine / note= "The position 1 and position 2 alanine
residues are both D-alanine"

( x i ) SEQUENCE DESCRIPTION: SEQ ID NO:66:

Ala  Ala  Ile  Lys  Ile  Ser  Gly  Lys  Trp  Lys  Ala  Gln  Lys  Arg  Phe  Leu
1                   5                        10                       15

Lys ( 2 ) INFORMATION FOR SEQ ID NO:67:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.5"

( x i ) SEQUENCE DESCRIPTION: SEQ ID NO:67:

Val  His  Val  His  Ile  Ser  Lys  Ser  Lys  Val  Gly  Trp  Leu  Ile  Gln  Leu
1                   5                        10                       15

Phe  His  Lys  Lys  Ile  Glu
                    20

( 2 ) INFORMATION FOR SEQ ID NO:68:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.65 reduced"

( i x ) FEATURE:
        ( A ) NAME/KEY: Disulfide-bond
        ( B ) LOCATION: 1..17

( x i ) SEQUENCE DESCRIPTION: SEQ ID NO:68:

Cys  Ile  Lys  Ile  Ser  Gly  Lys  Trp  Lys  Ala  Gln  Lys  Arg  Phe  Leu  Lys
1                   5                        10                       15

Cys ( 2 ) INFORMATION FOR SEQ ID NO:69:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rBPI"

( x i ) SEQUENCE DESCRIPTION: SEQ ID NO:69:

Met  Arg  Glu  Asn  Met  Ala  Arg  Gly  Pro  Cys  Asn  Ala  Pro  Arg  Trp  Val
-31  -30                 -25                    -20

Ser  Leu  Met  Val  Leu  Val  Ala  Ile  Gly  Thr  Ala  Val  Thr  Ala  Ala  Val
-15                      -10                      -5                        1

Asn  Pro  Gly  Val  Val  Val  Arg  Ile  Ser  Gln  Lys  Gly  Leu  Asp  Tyr  Ala

|   |   |   |   | 5 |   |   |   |   | 10 |   |   |   |   | 15 |   |
|---|---|---|---|---|---|---|---|---|---|---|---|---|---|---|---|
| Ser | Gln | Gln | Gly | Thr | Ala | Ala | Leu | Gln | Lys | Glu | Leu | Lys | Arg | Ile | Lys |
|   |   | 20 |   |   |   |   | 25 |   |   |   |   | 30 |   |   |   |
| Ile | Pro | Asp | Tyr | Ser | Asp | Ser | Phe | Lys | Ile | Lys | His | Leu | Gly | Lys | Gly |
|   | 35 |   |   |   |   | 40 |   |   |   |   | 45 |   |   |   |   |
| His | Tyr | Ser | Phe | Tyr | Ser | Met | Asp | Ile | Arg | Glu | Phe | Gln | Leu | Pro | Ser |
| 50 |   |   |   |   | 55 |   |   |   |   | 60 |   |   |   |   | 65 |
| Ser | Gln | Ile | Ser | Met | Val | Pro | Asn | Val | Gly | Leu | Lys | Phe | Ser | Ile | Ser |
|   |   |   |   | 70 |   |   |   |   | 75 |   |   |   |   | 80 |   |
| Asn | Ala | Asn | Ile | Lys | Ile | Ser | Gly | Lys | Trp | Lys | Ala | Gln | Lys | Arg | Phe |
|   |   |   | 85 |   |   |   |   | 90 |   |   |   |   | 95 |   |   |
| Leu | Lys | Met | Ser | Gly | Asn | Phe | Asp | Leu | Ser | Ile | Glu | Gly | Met | Ser | Ile |
|   |   | 100 |   |   |   |   | 105 |   |   |   |   | 110 |   |   |   |
| Ser | Ala | Asp | Leu | Lys | Leu | Gly | Ser | Asn | Pro | Thr | Ser | Gly | Lys | Pro | Thr |
|   | 115 |   |   |   |   | 120 |   |   |   |   | 125 |   |   |   |   |
| Ile | Thr | Cys | Ser | Ser | Cys | Ser | Ser | His | Ile | Asn | Ser | Val | His | Val | His |
| 130 |   |   |   |   | 135 |   |   |   |   | 140 |   |   |   |   | 145 |
| Ile | Ser | Lys | Ser | Lys | Val | Gly | Trp | Leu | Ile | Gln | Leu | Phe | His | Lys | Lys |
|   |   |   |   | 150 |   |   |   |   | 155 |   |   |   |   | 160 |   |
| Ile | Glu | Ser | Ala | Leu | Arg | Asn | Lys | Met | Asn | Ser | Gln | Val | Cys | Glu | Lys |
|   |   |   | 165 |   |   |   |   | 170 |   |   |   |   | 175 |   |   |
| Val | Thr | Asn | Ser | Val | Ser | Ser | Lys | Leu | Gln | Pro | Tyr | Phe | Gln | Thr | Leu |
|   |   | 180 |   |   |   |   | 185 |   |   |   |   | 190 |   |   |   |
| Pro | Val | Met | Thr | Lys | Ile | Asp | Ser | Val | Ala | Gly | Ile | Asn | Tyr | Gly | Leu |
|   | 195 |   |   |   |   | 200 |   |   |   |   | 205 |   |   |   |   |
| Val | Ala | Pro | Pro | Ala | Thr | Thr | Ala | Glu | Thr | Leu | Asp | Val | Gln | Met | Lys |
| 210 |   |   |   |   | 215 |   |   |   |   | 220 |   |   |   |   | 225 |
| Gly | Glu | Phe | Tyr | Ser | Glu | Asn | His | His | Asn | Pro | Pro | Pro | Phe | Ala | Pro |
|   |   |   |   | 230 |   |   |   |   | 235 |   |   |   |   | 240 |   |
| Pro | Val | Met | Glu | Phe | Pro | Ala | Ala | His | Asp | Arg | Met | Val | Tyr | Leu | Gly |
|   |   |   | 245 |   |   |   |   | 250 |   |   |   |   | 255 |   |   |
| Leu | Ser | Asp | Tyr | Phe | Phe | Asn | Thr | Ala | Gly | Leu | Val | Tyr | Gln | Glu | Ala |
|   |   | 260 |   |   |   |   | 265 |   |   |   |   | 270 |   |   |   |
| Gly | Val | Leu | Lys | Met | Thr | Leu | Arg | Asp | Asp | Met | Ile | Pro | Lys | Glu | Ser |
|   | 275 |   |   |   |   | 280 |   |   |   |   | 285 |   |   |   |   |
| Lys | Phe | Arg | Leu | Thr | Thr | Lys | Phe | Phe | Gly | Thr | Phe | Leu | Pro | Glu | Val |
| 290 |   |   |   |   | 295 |   |   |   |   | 300 |   |   |   |   | 305 |
| Ala | Lys | Lys | Phe | Pro | Asn | Met | Lys | Ile | Gln | Ile | His | Val | Ser | Ala | Ser |
|   |   |   |   | 310 |   |   |   |   | 315 |   |   |   |   | 320 |   |
| Thr | Pro | Pro | His | Leu | Ser | Val | Gln | Pro | Thr | Gly | Leu | Thr | Phe | Tyr | Pro |
|   |   |   | 325 |   |   |   |   | 330 |   |   |   |   | 335 |   |   |
| Ala | Val | Asp | Val | Gln | Ala | Phe | Ala | Val | Leu | Pro | Asn | Ser | Ser | Leu | Ala |
|   |   | 340 |   |   |   |   | 345 |   |   |   |   | 350 |   |   |   |
| Ser | Leu | Phe | Leu | Ile | Gly | Met | His | Thr | Thr | Gly | Ser | Met | Glu | Val | Ser |
|   | 355 |   |   |   |   | 360 |   |   |   |   | 365 |   |   |   |   |
| Ala | Glu | Ser | Asn | Arg | Leu | Val | Gly | Glu | Leu | Lys | Leu | Asp | Arg | Leu | Leu |
| 370 |   |   |   |   | 375 |   |   |   |   | 380 |   |   |   |   | 385 |
| Leu | Glu | Leu | Lys | His | Ser | Asn | Ile | Gly | Pro | Phe | Pro | Val | Glu | Leu | Leu |
|   |   |   |   | 390 |   |   |   |   | 395 |   |   |   |   | 400 |   |
| Gln | Asp | Ile | Met | Asn | Tyr | Ile | Val | Pro | Ile | Leu | Val | Leu | Pro | Arg | Val |
|   |   |   | 405 |   |   |   |   | 410 |   |   |   |   | 415 |   |   |
| Asn | Glu | Lys | Leu | Gln | Lys | Gly | Phe | Pro | Leu | Pro | Thr | Pro | Ala | Arg | Val |
|   |   | 420 |   |   |   |   | 425 |   |   |   |   | 430 |   |   |   |

```
Gln Leu Tyr Asn Val Val Leu Gln Pro His Gln Asn Phe Leu Leu Phe
    435                 440                 445

Gly Ala Asp Val Val Tyr Lys
450                 455
```

( 2 ) INFORMATION FOR SEQ ID NO:70:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.74"

( x i ) SEQUENCE DESCRIPTION: SEQ ID NO:70:

```
Lys Ser Lys Val Gly Trp Leu Ile Gln Leu Phe His Lys Lys Lys Trp
1               5                   10                  15

Lys Ala Gln Lys Arg Phe Leu Lys
                20
```

( 2 ) INFORMATION FOR SEQ ID NO:71:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.76"

( i x ) FEATURE:
        ( A ) NAME/KEY: Modified-site
        ( B ) LOCATION: 10..12
        ( D ) OTHER INFORMATION: /label= D- Phe
              / note= "The amino acid at position 11 is
              D- phenylalanine"

( x i ) SEQUENCE DESCRIPTION: SEQ ID NO:71:

```
Ile Lys Ile Ser Gly Lys Trp Lys Ala Gln Phe Arg Phe Leu Lys
1               5                   10                  15
```

( 2 ) INFORMATION FOR SEQ ID NO:72:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.77"

( x i ) SEQUENCE DESCRIPTION: SEQ ID NO:72:

```
Ile Lys Ile Ser Gly Lys Trp Lys Ala Gln Trp Arg Phe Leu Lys
1               5                   10                  15
```

( 2 ) INFORMATION FOR SEQ ID NO:73:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.79"

( x i ) SEQUENCE DESCRIPTION: SEQ ID NO:73:

Ile Lys Ile Ser Gly Lys Trp Lys Ala Lys Lys Arg Phe Leu Lys
    1               5                   10                  15

( 2 ) INFORMATION FOR SEQ ID NO:74:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.80"

( i x ) FEATURE:
            ( A ) NAME/KEY: Modified-site
            ( B ) LOCATION: 10..12
            ( D ) OTHER INFORMATION: /label= Substituted-Ala
                  / note= "The alanine at position 11 is
                  beta-1- naphthyl-substituted"

( x i ) SEQUENCE DESCRIPTION: SEQ ID NO:74:

Ile Lys Ile Ser Gly Lys Trp Lys Ala Gln Ala Arg Phe Leu Lys
    1               5                   10                  15

( 2 ) INFORMATION FOR SEQ ID NO:75:

( i ) SEQUENCE CHARACTERISTICS:
            ( A ) LENGTH: 15 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.81"

( x i ) SEQUENCE DESCRIPTION: SEQ ID NO:75:

Ile Lys Ile Ser Gly Lys Trp Lys Ala Phe Lys Arg Phe Leu Lys
    1               5                   10                  15

( 2 ) INFORMATION FOR SEQ ID NO:76:

( i ) SEQUENCE CHARACTERISTICS:
            ( A ) LENGTH: 14 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.82"

( x i ) SEQUENCE DESCRIPTION: SEQ ID NO:76:

Lys Ser Lys Val Gly Trp Leu Ile Gln Leu Trp His Lys Lys
    1               5                   10

( 2 ) INFORMATION FOR SEQ ID NO:77:

( i ) SEQUENCE CHARACTERISTICS:

(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.83"

(ix) FEATURE:
(A) NAME/KEY: Modified-site
(B) LOCATION: 10..12
(D) OTHER INFORMATION: /label= Substituted-Ala
/ note= "The alanine at position 6 is
beta-1- naphthyl-substituted"

(xi) SEQUENCE DESCRIPTION: SEQ ID NO:77:

```
Lys  Ser  Lys  Val  Gly  Ala  Lys  Ile  Gln  Leu  Phe  His  Lys  Lys
1                 5                        10
```

(2) INFORMATION FOR SEQ ID NO:78:

(i) SEQUENCE CHARACTERISTICS:
(A) LENGTH: 15 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.84"

(ix) FEATURE:
(A) NAME/KEY: Modified-site
(B) LOCATION: 6..8
(D) OTHER INFORMATION: /label= Substituted-Ala
/ note= "The alanine at position 7 is
beta-1- naphthyl-substituted"

(xi) SEQUENCE DESCRIPTION: SEQ ID NO:78:

```
Ile  Lys  Ile  Ser  Gly  Lys  Ala  Lys  Ala  Gln  Phe  Arg  Phe  Leu  Lys
1                 5                        10                        15
```

(2) INFORMATION FOR SEQ ID NO:79:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.85"

(xi) SEQUENCE DESCRIPTION: SEQ ID NO:79:

```
Lys  Ser  Lys  Val  Leu  Trp  Leu  Ile  Gln  Leu  Phe  His  Lys  Lys
1                 5                        10
```

(2) INFORMATION FOR SEQ ID NO:80:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.86"

( x i ) SEQUENCE DESCRIPTION: SEQ ID NO:80:

Lys Ser Lys Val Gly Trp Leu Ile Leu Leu Phe His Lys Lys
1               5                   10

( 2 ) INFORMATION FOR SEQ ID NO:81:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.87"

( x i ) SEQUENCE DESCRIPTION: SEQ ID NO:81:

Lys Ser Lys Val Gly Trp Leu Ile Gln Leu Phe Leu Lys Lys
1               5                   10

( 2 ) INFORMATION FOR SEQ ID NO:82:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.88"

( x i ) SEQUENCE DESCRIPTION: SEQ ID NO:82:

Ile Lys Ile Ser Gly Lys Trp Lys Ala Phe Phe Arg Phe Leu Lys
1               5                   10                  15

( 2 ) INFORMATION FOR SEQ ID NO:83:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.98"

( i x ) FEATURE:
        ( A ) NAME/KEY: Modified-site
        ( B ) LOCATION: 2
        ( D ) OTHER INFORMATION: /label= Substituted-Trp
          / note= "The alanine at position 2 is
          beta-1- naphthyl-substituted"

( x i ) SEQUENCE DESCRIPTION: SEQ ID NO:83:

Lys Trp Lys Ala Gln Phe Arg Phe Leu Lys Lys Ser Lys Val Gly Trp
1               5                   10                  15

Leu Ile Phe Leu Phe His Lys Lys
                20

( 2 ) INFORMATION FOR SEQ ID NO:84:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.89"

( i x ) FEATURE:
    ( A ) NAME/KEY: Modified-site
    ( B ) LOCATION: 6..8
    ( D ) OTHER INFORMATION: /label= Substituted-Ala
        / note= "The alanine at position 7 is
        beta-1- naphthyl-substituted"

( x i ) SEQUENCE DESCRIPTION: SEQ ID NO:84:

```
Ile Lys Ile Ser Gly Lys Ala Lys Ala Phe Lys Arg Phe Leu Lys
1               5                   10                  15
```

( 2 ) INFORMATION FOR SEQ ID NO:85:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.90"

( i x ) FEATURE:
        ( A ) NAME/KEY: Modified-site
        ( B ) LOCATION: 6..8
        ( D ) OTHER INFORMATION: /label= Substituted-Ala
            / note= "The alanine at position 7 is
            beta-1- naphthyl-substituted"

( x i ) SEQUENCE DESCRIPTION: SEQ ID NO:85:

```
Ile Lys Ile Ser Gly Lys Ala Lys Ala Phe Phe Arg Phe Leu Lys
1               5                   10                  15
```

( 2 ) INFORMATION FOR SEQ ID NO:86:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.91"

( x i ) SEQUENCE DESCRIPTION: SEQ ID NO:86:

```
Lys Ser Lys Val Gly Trp Leu Ile Phe Leu Phe His Lys Lys
1               5                   10
```

( 2 ) INFORMATION FOR SEQ ID NO:87:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.92"

( x i ) SEQUENCE DESCRIPTION: SEQ ID NO:87:

```
Lys  Ser  Lys  Val  Gly  Trp  Leu  Ile  Lys  Leu  Phe  His  Lys  Lys
 1              5                        10
```

( 2 ) INFORMATION FOR SEQ ID NO:88:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.93"

( i x ) FEATURE:
        ( A ) NAME/KEY: Modified-site
        ( B ) LOCATION: 6..8
        ( D ) OTHER INFORMATION: /label= Substituted-Ala
            / note= "The alanine at position 7 is
            beta-1- naphthyl-substituted"

( x i ) SEQUENCE DESCRIPTION: SEQ ID NO:88:

```
Ile  Lys  Ile  Ser  Gly  Lys  Ala  Lys  Ala  Gln  Phe  Arg  Phe  Leu  Lys  Lys
 1              5                        10                            15

Ser  Lys  Val  Gly  Trp  Leu  Ile  Gln  Leu  Phe  His  Lys  Lys
          20                        25
```

( 2 ) INFORMATION FOR SEQ ID NO:89:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.94"

( x i ) SEQUENCE DESCRIPTION: SEQ ID NO:89:

```
Lys  Ser  Lys  Val  Gly  Trp  Leu  Ile  Gln  Leu  Phe  Phe  Lys  Lys
 1              5                        10
```

( 2 ) INFORMATION FOR SEQ ID NO:90:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.95"

( x i ) SEQUENCE DESCRIPTION: SEQ ID NO:90:

```
Lys  Ser  Lys  Val  Phe  Trp  Leu  Ile  Gln  Leu  Phe  His  Lys  Lys
 1              5                        10
```

( 2 ) INFORMATION FOR SEQ ID NO:91:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.96"

( x i ) SEQUENCE DESCRIPTION: SEQ ID NO:91:

Lys Ser Lys Val Gly Trp Leu Ile Gln Leu Phe His Lys Phe
1               5                   10

( 2 ) INFORMATION FOR SEQ ID NO:92:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.97"

( x i ) SEQUENCE DESCRIPTION: SEQ ID NO:92:

Lys Ser Lys Val Lys Trp Leu Ile Gln Leu Phe His Lys Lys
1               5                   10

( 2 ) INFORMATION FOR SEQ ID NO:93:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.99"

( x i ) SEQUENCE DESCRIPTION: SEQ ID NO:93:

Lys Trp Lys Ala Gln Trp Arg Phe Leu Lys Lys Trp Lys Ala Gln Trp
1               5                   10                  15

Arg Phe Leu Lys Lys Trp Lys Ala Gln Trp Arg Phe Leu Lys
            20                  25                  30

( 2 ) INFORMATION FOR SEQ ID NO:94:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.100"

( x i ) SEQUENCE DESCRIPTION: SEQ ID NO:94:

Lys Ser Lys Val Lys Trp Leu Ile Lys Leu Phe His Lys Lys
1               5                   10

( 2 ) INFORMATION FOR SEQ ID NO:95:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( i x ) FEATURE:

( A ) NAME/KEY: misc_feature
( D ) OTHER INFORMATION: "XMP.101"

( x i ) SEQUENCE DESCRIPTION: SEQ ID NO:95:

| Lys | Ser | Lys | Val | Lys | Trp | Leu | Ile | Lys | Leu | Phe | Phe | Lys | Phe | Lys | Ser |
|---|---|---|---|---|---|---|---|---|---|---|---|---|---|---|---|
| 1 | | | | 5 | | | | | 10 | | | | | 15 | |

| Lys | Val | Lys | Trp | Leu | Ile | Lys | Leu | Phe | Phe | Lys | Phe |
|---|---|---|---|---|---|---|---|---|---|---|---|
| | | | 20 | | | | | 25 | | | |

( 2 ) INFORMATION FOR SEQ ID NO:96:

( i ) SEQUENCE CHARACTERISTICS:
      ( A ) LENGTH: 24 amino acids
      ( B ) TYPE: amino acid
      ( D ) TOPOLOGY: linear ( i i ) MOLECULE TYPE: peptide ( i x ) FEATURE:
      ( A ) NAME/KEY: misc_feature
      ( D ) OTHER INFORMATION: "XMP.102"

( x i ) SEQUENCE DESCRIPTION: SEQ ID NO:96:

| Lys | Trp | Lys | Ala | Gln | Phe | Arg | Phe | Leu | Lys | Lys | Ser | Lys | Val | Gly | Trp |
|---|---|---|---|---|---|---|---|---|---|---|---|---|---|---|---|
| 1 | | | | 5 | | | | | 10 | | | | | 15 | |

| Leu | Ile | Leu | Leu | Phe | His | Lys | Lys |
|---|---|---|---|---|---|---|---|
| | | | 20 | | | | |

( 2 ) INFORMATION FOR SEQ ID NO:97:

( i ) SEQUENCE CHARACTERISTICS:
      ( A ) LENGTH: 1443 base pairs
      ( B ) TYPE: nucleic acid
      ( C ) STRANDEDNESS: single
      ( D ) TOPOLOGY: linear ( i i ) MOLECULE TYPE: DNA ( i x ) FEATURE:
      ( A ) NAME/KEY: CDS
      ( B ) LOCATION: 1..1443

( i x ) FEATURE:
      ( A ) NAME/KEY: mat_peptide
      ( B ) LOCATION: 76..1443

( i x ) FEATURE:
      ( A ) NAME/KEY: misc_feature
      ( D ) OTHER INFORMATION: "rLBP"

( x i ) SEQUENCE DESCRIPTION: SEQ ID NO:97:

| ATG | GGG | GCC | TTG | GCC | AGA | GCC | CTG | CCG | TCC | ATA | CTG | CTG | GCA | TTG | CTG | 48 |
|---|---|---|---|---|---|---|---|---|---|---|---|---|---|---|---|---|
| Met | Gly | Ala | Leu | Ala | Arg | Ala | Leu | Pro | Ser | Ile | Leu | Leu | Ala | Leu | Leu | |
| -25 | | | | -20 | | | | | -15 | | | | | -10 | | |

| CTT | ACG | TCC | ACC | CCA | GAG | GCT | CTG | GGT | GCC | AAC | CCC | GGC | TTG | GTC | GCC | 96 |
|---|---|---|---|---|---|---|---|---|---|---|---|---|---|---|---|---|
| Leu | Thr | Ser | Thr | Pro | Glu | Ala | Leu | Gly | Ala | Asn | Pro | Gly | Leu | Val | Ala | |
| | | | | -5 | | | | | 1 | | | | | 5 | | |

| AGG | ATC | ACC | GAC | AAG | GGA | CTG | CAG | TAT | GCG | GCC | CAG | GAG | GGG | CTA | TTG | 144 |
|---|---|---|---|---|---|---|---|---|---|---|---|---|---|---|---|---|
| Arg | Ile | Thr | Asp | Lys | Gly | Leu | Gln | Tyr | Ala | Ala | Gln | Glu | Gly | Leu | Leu | |
| | | | 10 | | | | | 15 | | | | | 20 | | | |

| GCT | CTG | CAG | AGT | GAG | CTG | CTC | AGG | ATC | ACG | CTG | CCT | GAC | TTC | ACC | GGG | 192 |
|---|---|---|---|---|---|---|---|---|---|---|---|---|---|---|---|---|
| Ala | Leu | Gln | Ser | Glu | Leu | Leu | Arg | Ile | Thr | Leu | Pro | Asp | Phe | Thr | Gly | |
| | | 25 | | | | | 30 | | | | | 35 | | | | |

| GAC | TTG | AGG | ATC | CCC | CAC | GTC | GGC | CGT | GGG | CGC | TAT | GAG | TTC | CAC | AGC | 240 |
|---|---|---|---|---|---|---|---|---|---|---|---|---|---|---|---|---|
| Asp | Leu | Arg | Ile | Pro | His | Val | Gly | Arg | Gly | Arg | Tyr | Glu | Phe | His | Ser | |
| | 40 | | | | | 45 | | | | | 50 | | | | 55 | |

| CTG | AAC | ATC | CAC | AGC | TGT | GAG | CTG | CTT | CAC | TCT | GCG | CTG | AGG | CCT | GTC | 288 |
|---|---|---|---|---|---|---|---|---|---|---|---|---|---|---|---|---|
| Leu | Asn | Ile | His | Ser | Cys | Glu | Leu | Leu | His | Ser | Ala | Leu | Arg | Pro | Val | |

|  |  |  |  |  |  |  |  |  |  |  |  |  |  |  |  |
|---|---|---|---|---|---|---|---|---|---|---|---|---|---|---|---|
|  |  |  |  | 60 |  |  |  |  | 65 |  |  |  |  | 70 |  |
| CCT | GGC | CAG | GGC | CTG | AGT | CTC | AGC | ATC | TCC | GAC | TCC | TCC | ATC | CGG | GTC |
| Pro | Gly | Gln | Gly<br>75 | Leu | Ser | Leu | Ser | Ile<br>80 | Ser | Asp | Ser | Ser | Ile<br>85 | Arg | Val |

336

| CAG | GGC | AGG | TGG | AAG | GTG | CGC | AAG | TCA | TTC | TTC | AAA | CTA | CAG | GGC | TCC |
|---|---|---|---|---|---|---|---|---|---|---|---|---|---|---|---|
| Gln | Gly | Arg<br>90 | Trp | Lys | Val | Arg | Lys<br>95 | Ser | Phe | Phe | Lys | Leu<br>100 | Gln | Gly | Ser |

384

| TTT | GAT | GTC | AGT | GTC | AAG | GGC | ATC | AGC | ATT | TCG | GTC | AAC | CTC | CTG | TTG |
|---|---|---|---|---|---|---|---|---|---|---|---|---|---|---|---|
| Phe | Asp | Val<br>105 | Ser | Val | Lys | Gly | Ile<br>110 | Ser | Ile | Ser | Val | Asn<br>115 | Leu | Leu | Leu |

432

| GGC | AGC | GAG | TCC | TCC | GGG | AGG | CCC | ACA | GTT | ACT | GCC | TCC | AGC | TGC | AGC |
|---|---|---|---|---|---|---|---|---|---|---|---|---|---|---|---|
| Gly<br>120 | Ser | Glu | Ser | Ser | Gly<br>125 | Arg | Pro | Thr | Val | Thr<br>130 | Ala | Ser | Ser | Cys | Ser<br>135 |

480

| AGT | GAC | ATC | GCT | GAC | GTG | GAG | GTG | GAC | ATG | TCG | GGA | GAC | TTG | GGG | TGG |
|---|---|---|---|---|---|---|---|---|---|---|---|---|---|---|---|
| Ser | Asp | Ile | Ala | Asp<br>140 | Val | Glu | Val | Asp | Met<br>145 | Ser | Gly | Asp | Leu | Gly<br>150 | Trp |

528

| CTG | TTG | AAC | CTC | TTC | CAC | AAC | CAG | ATT | GAG | TCC | AAG | TTC | CAG | AAA | GTA |
|---|---|---|---|---|---|---|---|---|---|---|---|---|---|---|---|
| Leu | Leu | Asn | Leu | Phe<br>155 | His | Asn | Gln | Ile | Glu<br>160 | Ser | Lys | Phe | Gln | Lys<br>165 | Val |

576

| CTG | GAG | AGC | AGG | ATT | TGC | GAA | ATG | ATC | CAG | AAA | TCG | GTG | TCC | TCC | GAT |
|---|---|---|---|---|---|---|---|---|---|---|---|---|---|---|---|
| Leu | Glu | Ser | Arg<br>170 | Ile | Cys | Glu | Met | Ile<br>175 | Gln | Lys | Ser | Val | Ser<br>180 | Ser | Asp |

624

| CTA | CAG | CCT | TAT | CTC | CAA | ACT | CTG | CCA | GTT | ACA | ACA | GAG | ATT | GAC | AGT |
|---|---|---|---|---|---|---|---|---|---|---|---|---|---|---|---|
| Leu | Gln | Pro<br>185 | Tyr | Leu | Gln | Thr | Leu<br>190 | Pro | Val | Thr | Thr | Glu<br>195 | Ile | Asp | Ser |

672

| TTC | GCC | GAC | ATT | GAT | TAT | AGC | TTA | GTG | GAA | GCC | CCT | CGG | GCA | ACA | GCC |
|---|---|---|---|---|---|---|---|---|---|---|---|---|---|---|---|
| Phe<br>200 | Ala | Asp | Ile | Asp | Tyr<br>205 | Ser | Leu | Val | Glu | Ala<br>210 | Pro | Arg | Ala | Thr | Ala<br>215 |

720

| CAG | ATG | CTG | GAG | GTG | ATG | TTT | AAG | GGT | GAA | ATC | TTT | CAT | CGT | AAC | CAC |
|---|---|---|---|---|---|---|---|---|---|---|---|---|---|---|---|
| Gln | Met | Leu | Glu | Val<br>220 | Met | Phe | Lys | Gly | Glu<br>225 | Ile | Phe | His | Arg | Asn<br>230 | His |

768

| CGT | TCT | CCA | GTT | ACC | CTC | CTT | GCT | GCA | GTC | ATG | AGC | CTT | CCT | GAG | GAA |
|---|---|---|---|---|---|---|---|---|---|---|---|---|---|---|---|
| Arg | Ser | Pro | Val<br>235 | Thr | Leu | Leu | Ala | Ala<br>240 | Val | Met | Ser | Leu | Pro<br>245 | Glu | Glu |

816

| CAC | AAC | AAA | ATG | GTC | TAC | TTT | GCC | ATC | TCG | GAT | TAT | GTC | TTC | AAC | ACG |
|---|---|---|---|---|---|---|---|---|---|---|---|---|---|---|---|
| His | Asn | Lys<br>250 | Met | Val | Tyr | Phe | Ala<br>255 | Ile | Ser | Asp | Tyr | Val<br>260 | Phe | Asn | Thr |

864

| GCC | AGC | CTG | GTT | TAT | CAT | GAG | GAA | GGA | TAT | CTG | AAC | TTC | TCC | ATC | ACA |
|---|---|---|---|---|---|---|---|---|---|---|---|---|---|---|---|
| Ala | Ser<br>265 | Leu | Val | Tyr | His | Glu<br>270 | Glu | Gly | Tyr | Leu | Asn<br>275 | Phe | Ser | Ile | Thr |

912

| GAT | GAG | ATG | ATA | CCG | CCT | GAC | TCT | AAT | ATC | CGA | CTG | ACC | ACC | AAG | TCC |
|---|---|---|---|---|---|---|---|---|---|---|---|---|---|---|---|
| Asp<br>280 | Glu | Met | Ile | Pro | Pro<br>285 | Asp | Ser | Asn | Ile | Arg<br>290 | Leu | Thr | Thr | Lys | Ser<br>295 |

960

| TTC | CGA | CCC | TTC | GTC | CCA | CGG | TTA | GCC | AGG | CTC | TAC | CCC | AAC | ATG | AAC |
|---|---|---|---|---|---|---|---|---|---|---|---|---|---|---|---|
| Phe | Arg | Pro | Phe | Val<br>300 | Pro | Arg | Leu | Ala | Arg<br>305 | Leu | Tyr | Pro | Asn | Met<br>310 | Asn |

1008

| CTG | GAA | CTC | CAG | GGA | TCA | GTG | CCC | TCT | GCT | CCG | CTC | CTG | AAC | TTC | AGC |
|---|---|---|---|---|---|---|---|---|---|---|---|---|---|---|---|
| Leu | Glu | Leu | Gln | Gly<br>315 | Ser | Val | Pro | Ser | Ala<br>320 | Pro | Leu | Leu | Asn | Phe<br>325 | Ser |

1056

| CCT | GGG | AAT | CTG | TCT | GTG | GAC | CCC | TAT | ATG | GAG | ATA | GAT | GCC | TTT | GTG |
|---|---|---|---|---|---|---|---|---|---|---|---|---|---|---|---|
| Pro | Gly | Asn<br>330 | Leu | Ser | Val | Asp | Pro<br>335 | Tyr | Met | Glu | Ile | Asp<br>340 | Ala | Phe | Val |

1104

| CTC | CTG | CCC | AGC | TCC | AGC | AAG | GAG | CCT | GTC | TTC | CGG | CTC | AGT | GTG | GCC |
|---|---|---|---|---|---|---|---|---|---|---|---|---|---|---|---|
| Leu<br>345 | Leu | Pro | Ser | Ser | Ser<br>350 | Lys | Glu | Pro | Val | Phe<br>355 | Arg | Leu | Ser | Val | Ala |

1152

| ACT | AAT | GTG | TCC | GCC | ACC | TTG | ACC | TTC | AAT | ACC | AGC | AAG | ATC | ACT | GGG |
|---|---|---|---|---|---|---|---|---|---|---|---|---|---|---|---|
| Thr<br>360 | Asn | Val | Ser | Ala | Thr<br>365 | Leu | Thr | Phe | Asn | Thr<br>370 | Ser | Lys | Ile | Thr | Gly<br>375 |

1200

| TTC | CTG | AAG | CCA | GGA | AAG | GTA | AAA | GTG | GAA | CTG | AAA | GAA | TCC | AAA | GTT |
|---|---|---|---|---|---|---|---|---|---|---|---|---|---|---|---|
| Phe | Leu | Lys | Pro | Gly | Lys | Val | Lys | Val | Glu | Leu | Lys | Glu | Ser | Lys | Val |

1248

|  |  |  |  |  | 380 |  |  |  |  | 385 |  |  |  |  | 390 |  |
|---|---|---|---|---|---|---|---|---|---|---|---|---|---|---|---|---|
| GGA | CTA | TTC | AAT | GCA | GAG | CTG | TTG | GAA | GCG | CTC | CTC | AAC | TAT | TAC | ATC | 1296 |
| Gly | Leu | Phe | Asn | Ala | Glu | Leu | Leu | Glu | Ala | Leu | Leu | Asn | Tyr | Tyr | Ile |  |
|  |  |  | 395 |  |  |  |  | 400 |  |  |  |  | 405 |  |  |  |
| CTT | AAC | ACC | TTC | TAC | CCC | AAG | TTC | AAT | GAT | AAG | TTG | GCC | GAA | GGC | TTC | 1344 |
| Leu | Asn | Thr | Phe | Tyr | Pro | Lys | Phe | Asn | Asp | Lys | Leu | Ala | Glu | Gly | Phe |  |
|  |  | 410 |  |  |  |  | 415 |  |  |  |  | 420 |  |  |  |  |
| CCC | CTT | CCT | CTG | CTG | AAG | CGT | GTT | CAG | CTC | TAC | GAC | CTT | GGG | CTG | CAG | 1392 |
| Pro | Leu | Pro | Leu | Leu | Lys | Arg | Val | Gln | Leu | Tyr | Asp | Leu | Gly | Leu | Gln |  |
|  | 425 |  |  |  |  | 430 |  |  |  |  | 435 |  |  |  |  |  |
| ATC | CAT | AAG | GAC | TTC | CTG | TTC | TTG | GGT | GCC | AAT | GTC | CAA | TAC | ATG | AGA | 1440 |
| Ile | His | Lys | Asp | Phe | Leu | Phe | Leu | Gly | Ala | Asn | Val | Gln | Tyr | Met | Arg |  |
| 440 |  |  |  | 445 |  |  |  |  | 450 |  |  |  |  |  | 455 |  |
| GTT |  |  |  |  |  |  |  |  |  |  |  |  |  |  |  | 1443 |
| Val |  |  |  |  |  |  |  |  |  |  |  |  |  |  |  |  |

( 2 ) INFORMATION FOR SEQ ID NO:98:

( i ) SEQUENCE CHARACTERISTICS:
        ( A ) LENGTH: 481 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( D ) OTHER INFORMATION: "rLBP"

( x i ) SEQUENCE DESCRIPTION: SEQ ID NO:98:

| Met | Gly | Ala | Leu | Ala | Arg | Ala | Leu | Pro | Ser | Ile | Leu | Ala | Leu | Leu |
|---|---|---|---|---|---|---|---|---|---|---|---|---|---|---|
| -25 |  |  |  |  | -20 |  |  |  |  | -15 |  |  |  | -10 |
| Leu | Thr | Ser | Thr | Pro | Glu | Ala | Leu | Gly | Ala | Asn | Pro | Gly | Leu | Val | Ala |
|  |  |  |  | -5 |  |  |  |  | 1 |  |  |  | 5 |  |  |
| Arg | Ile | Thr | Asp | Lys | Gly | Leu | Gln | Tyr | Ala | Ala | Gln | Glu | Gly | Leu | Leu |
|  |  | 10 |  |  |  |  | 15 |  |  |  |  | 20 |  |  |  |
| Ala | Leu | Gln | Ser | Glu | Leu | Leu | Arg | Ile | Thr | Leu | Pro | Asp | Phe | Thr | Gly |
|  | 25 |  |  |  |  | 30 |  |  |  |  | 35 |  |  |  |  |
| Asp | Leu | Arg | Ile | Pro | His | Val | Gly | Arg | Gly | Arg | Tyr | Glu | Phe | His | Ser |
| 40 |  |  |  | 45 |  |  |  |  | 50 |  |  |  |  |  | 55 |
| Leu | Asn | Ile | His | Ser | Cys | Glu | Leu | Leu | His | Ser | Ala | Leu | Arg | Pro | Val |
|  |  |  | 60 |  |  |  |  | 65 |  |  |  |  | 70 |  |  |
| Pro | Gly | Gln | Gly | Leu | Ser | Leu | Ser | Ile | Ser | Asp | Ser | Ser | Ile | Arg | Val |
|  |  | 75 |  |  |  |  | 80 |  |  |  |  | 85 |  |  |  |
| Gln | Gly | Arg | Trp | Lys | Val | Arg | Lys | Ser | Phe | Phe | Lys | Leu | Gln | Gly | Ser |
|  |  | 90 |  |  |  |  | 95 |  |  |  |  | 100 |  |  |  |
| Phe | Asp | Val | Ser | Val | Lys | Gly | Ile | Ser | Ile | Ser | Val | Asn | Leu | Leu | Leu |
|  | 105 |  |  |  |  | 110 |  |  |  |  | 115 |  |  |  |  |
| Gly | Ser | Glu | Ser | Ser | Gly | Arg | Pro | Thr | Val | Thr | Ala | Ser | Ser | Cys | Ser |
| 120 |  |  |  |  | 125 |  |  |  |  | 130 |  |  |  |  | 135 |
| Ser | Asp | Ile | Ala | Asp | Val | Glu | Val | Asp | Met | Ser | Gly | Asp | Leu | Gly | Trp |
|  |  |  |  | 140 |  |  |  |  | 145 |  |  |  |  | 150 |  |
| Leu | Leu | Asn | Leu | Phe | His | Asn | Gln | Ile | Glu | Ser | Lys | Phe | Gln | Lys | Val |
|  |  |  | 155 |  |  |  |  | 160 |  |  |  |  | 165 |  |  |
| Leu | Glu | Ser | Arg | Ile | Cys | Glu | Met | Ile | Gln | Lys | Ser | Val | Ser | Ser | Asp |
|  |  | 170 |  |  |  |  | 175 |  |  |  |  | 180 |  |  |  |
| Leu | Gln | Pro | Tyr | Leu | Gln | Thr | Leu | Pro | Val | Thr | Thr | Glu | Ile | Asp | Ser |
|  | 185 |  |  |  |  | 190 |  |  |  |  | 195 |  |  |  |  |
| Phe | Ala | Asp | Ile | Asp | Tyr | Ser | Leu | Val | Glu | Ala | Pro | Arg | Ala | Thr | Ala |

```
              200                 205                 210                 215
Gln  Met  Leu  Glu  Val  Met  Phe  Lys  Gly  Glu  Ile  Phe  His  Arg  Asn  His
                         220                 225                 230

Arg  Ser  Pro  Val  Thr  Leu  Leu  Ala  Ala  Val  Met  Ser  Leu  Pro  Glu  Glu
                         235                 240                 245

His  Asn  Lys  Met  Val  Tyr  Phe  Ala  Ile  Ser  Asp  Tyr  Val  Phe  Asn  Thr
               250                 255                 260

Ala  Ser  Leu  Val  Tyr  His  Glu  Gly  Tyr  Leu  Asn  Phe  Ser  Ile  Thr
     265                 270                 275

Asp  Glu  Met  Ile  Pro  Pro  Asp  Ser  Asn  Ile  Arg  Leu  Thr  Thr  Lys  Ser
280                      285                 290                      295

Phe  Arg  Pro  Phe  Val  Pro  Arg  Leu  Ala  Arg  Leu  Tyr  Pro  Asn  Met  Asn
                         300                 305                      310

Leu  Glu  Leu  Gln  Gly  Ser  Val  Pro  Ser  Ala  Pro  Leu  Leu  Asn  Phe  Ser
                    315                 320                      325

Pro  Gly  Asn  Leu  Ser  Val  Asp  Pro  Tyr  Met  Glu  Ile  Asp  Ala  Phe  Val
               330                 335                 340

Leu  Leu  Pro  Ser  Ser  Ser  Lys  Glu  Pro  Val  Phe  Arg  Leu  Ser  Val  Ala
     345                 350                      355

Thr  Asn  Val  Ser  Ala  Thr  Leu  Thr  Phe  Asn  Thr  Ser  Lys  Ile  Thr  Gly
360                      365                 370                      375

Phe  Leu  Lys  Pro  Gly  Lys  Val  Lys  Val  Glu  Leu  Lys  Glu  Ser  Lys  Val
                    380                 385                      390

Gly  Leu  Phe  Asn  Ala  Glu  Leu  Leu  Glu  Ala  Leu  Leu  Asn  Tyr  Tyr  Ile
               395                 400                 405

Leu  Asn  Thr  Phe  Tyr  Pro  Lys  Phe  Asn  Asp  Lys  Leu  Ala  Glu  Gly  Phe
          410                 415                 420

Pro  Leu  Pro  Leu  Leu  Lys  Arg  Val  Gln  Leu  Tyr  Asp  Leu  Gly  Leu  Gln
     425                 430                 435

Ile  His  Lys  Asp  Phe  Leu  Phe  Leu  Gly  Ala  Asn  Val  Gln  Tyr  Met  Arg
440                 445                 450                      455

Val
```

( 2 ) INFORMATION FOR SEQ ID NO:99:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.57"

( x i ) SEQUENCE DESCRIPTION: SEQ ID NO:99:

```
Cys  Ile  Lys  Ile  Ser  Gly  Lys  Trp  Lys  Ala  Gln  Lys  Arg  Pro  Leu  Cys
1              5                        10                       15
```

( 2 ) INFORMATION FOR SEQ ID NO:100:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature (D) OTHER INFORMATION: "XMP.75"

(xi) SEQUENCE DESCRIPTION: SEQ ID NO:100:

Ile Lys Lys Arg Ala Ile Ser Phe Leu Gly Lys Lys Trp Gln Lys
1               5                   10                  15

(2) INFORMATION FOR SEQ ID NO:101:

(i) SEQUENCE CHARACTERISTICS:
      (A) LENGTH: 20 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.282"

(xi) SEQUENCE DESCRIPTION: SEQ ID NO:101:

Lys Trp Lys Ala Phe Phe Arg Phe Leu Lys Lys Trp Lys Ala Phe Phe
1               5                   10                  15

Arg Phe Leu Lys
            20

(2) INFORMATION FOR SEQ ID NO:102:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.103"

(xi) SEQUENCE DESCRIPTION: SEQ ID NO:102:

Ile Lys Ile Ser Gly Lys Trp Lys Ala Trp Lys Arg Phe Leu Lys Lys
1               5                   10                  15

(2) INFORMATION FOR SEQ ID NO:103:

(i) SEQUENCE CHARACTERISTICS:
      (A) LENGTH: 14 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.104"

(xi) SEQUENCE DESCRIPTION: SEQ ID NO:103:

Lys Ser Lys Val Gly Trp Leu Ile Ser Leu Phe His Lys Lys
1               5                   10

(2) INFORMATION FOR SEQ ID NO:104:

(i) SEQUENCE CHARACTERISTICS:
      (A) LENGTH: 16 amino acids
      (B) TYPE: amino acid
      (D) TOPOLOGY: linear (ii) MOLECULE TYPE: peptide (ix) FEATURE:
      (A) NAME/KEY: misc_feature
      (D) OTHER INFORMATION: "XMP.105"

( i x ) FEATURE:
    ( A ) NAME/KEY: Modified-site
    ( B ) LOCATION: 13
    ( C ) OTHER INFORMATION: /label= Substituted-Ala
        / note= "The alanine at position 13 is beta-1-
        naphthyl- substituted."

( x i ) SEQUENCE DESCRIPTION: SEQ ID NO:104:

Ile Lys Ile Ser Gly Lys Trp Lys Ala Trp Lys Arg Ala Leu Lys Lys
1               5                   10                  15

( 2 ) INFORMATION FOR SEQ ID NO:105:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.106"

( x i ) SEQUENCE DESCRIPTION: SEQ ID NO:105:

Lys Ser Lys Val Gly Trp Leu Ile Thr Leu Phe His Lys Lys
1               5                   10

( 2 ) INFORMATION FOR SEQ ID NO:106:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.107"

( x i ) SEQUENCE DESCRIPTION: SEQ ID NO:106:

Lys Ser Lys Val Gly Trp Leu Ile Gln Leu Phe Trp Lys Lys
1               5                   10

( 2 ) INFORMATION FOR SEQ ID NO:107:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.108"

( x i ) SEQUENCE DESCRIPTION: SEQ ID NO:107:

Lys Ser Lys Val Gly Trp Leu Ile Gln Leu Phe His Lys Trp
1               5                   10

( 2 ) INFORMATION FOR SEQ ID NO:108:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide

```
( i x ) FEATURE:
        ( A ) NAME/KEY: misc_feature
        ( D ) OTHER INFORMATION: "XMP.109"

( i x ) FEATURE:
        ( A ) NAME/KEY: Modified-site
        ( B ) LOCATION: 11
        ( C ) OTHER INFORMATION: /label= Substituted-Ala
                / note= "The alanine at position 11 is beta-1-
                naphthyl- substituted."

( x i ) SEQUENCE DESCRIPTION: SEQ ID NO:108:

Lys  Ser  Lys  Val  Gly  Trp  Leu  Ile  Gln  Leu  Ala  His  Lys  Lys
1                  5                            10

( 2 ) INFORMATION FOR SEQ ID NO:109:

( i ) SEQUENCE CHARACTERISTICS:
                ( A ) LENGTH: 14 amino acids
                ( B ) TYPE: amino acid
                ( D ) TOPOLOGY: linear ( i i ) MOLECULE TYPE: peptide ( i x ) FEATURE:
                ( A ) NAME/KEY: misc_feature
                ( D ) OTHER INFORMATION: "XMP.110"

( i x ) FEATURE:
                ( A ) NAME/KEY: Modified-site
                ( B ) LOCATION: 12
                ( C ) OTHER INFORMATION: /label= Substituted-Ala
                        / note= "The alanine at position 12 is beta-1-
                        naphthyl- substituted."

( x i ) SEQUENCE DESCRIPTION: SEQ ID NO:109:

Lys  Ser  Lys  Val  Gly  Trp  Leu  Ile  Gln  Leu  Phe  Ala  Lys  Lys
1                  5                            10

( 2 ) INFORMATION FOR SEQ ID NO:110:

( i ) SEQUENCE CHARACTERISTICS:
                ( A ) LENGTH: 14 amino acids
                ( B ) TYPE: amino acid
                ( D ) TOPOLOGY: linear ( i i ) MOLECULE TYPE: peptide ( i x ) FEATURE:
                ( A ) NAME/KEY: misc_feature
                ( D ) OTHER INFORMATION: "XMP.111"

( i x ) FEATURE:
                ( A ) NAME/KEY: Modified-site
                ( B ) LOCATION: 14
                ( C ) OTHER INFORMATION: /label= Substituted-Ala
                        / note= "The alanine at position 14 is beta-1-
                        naphthyl- substituted."

( x i ) SEQUENCE DESCRIPTION: SEQ ID NO:110:

Lys  Ser  Lys  Val  Gly  Trp  Leu  Ile  Gln  Leu  Phe  His  Lys  Ala
1                  5                            10

( 2 ) INFORMATION FOR SEQ ID NO:111:

( i ) SEQUENCE CHARACTERISTICS:
                ( A ) LENGTH: 15 amino acids
                ( B ) TYPE: amino acid
                ( D ) TOPOLOGY: linear ( i i ) MOLECULE TYPE: peptide ( i x ) FEATURE:
                ( A ) NAME/KEY: misc_feature
```

(D) OTHER INFORMATION: "XMP.112"

(ix) FEATURE:
    (A) NAME/KEY: Modified-site
    (B) LOCATION: 7
    (C) OTHER INFORMATION: /label= Substituted-Ala
      / note= "The alanine at position 7 is beta-1-
      naphthyl- substituted."

(ix) FEATURE:
    (A) NAME/KEY: Modified-site
    (B) LOCATION: 11
    (C) OTHER INFORMATION: /label= Substituted-Ala
      / note= "The alanine at position 11 is beta-1-
      naphthyl- substituted."

(xi) SEQUENCE DESCRIPTION: SEQ ID NO:111:

```
Ile Lys Ile Ser Gly Lys Ala Lys Ala Gln Ala Arg Phe Leu Lys
1               5                   10                  15
```

(2) INFORMATION FOR SEQ ID NO:112:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "XMP.113"

(xi) SEQUENCE DESCRIPTION: SEQ ID NO:112:

```
Lys Ser Lys Val Gly Trp Leu Ile Gln Phe Phe His Lys Lys
1               5                   10
```

(2) INFORMATION FOR SEQ ID NO:113:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "XMP.114"

(xi) SEQUENCE DESCRIPTION: SEQ ID NO:113:

```
Lys Trp Gln Leu Arg Ser Lys Gly Lys Ile Lys Ile Phe Lys Ala
1               5                   10                  15
```

(2) INFORMATION FOR SEQ ID NO:114:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (ix) FEATURE:
    (A) NAME/KEY: misc_feature
    (D) OTHER INFORMATION: "XMP.116"

(ix) FEATURE:
    (A) NAME/KEY: Modified-site
    (B) LOCATION: 6
    (C) OTHER INFORMATION: /label= Substituted-Ala
      / note= "The alanine at position 6 is beta-1-
      naphthyl- substituted."

( x i ) SEQUENCE DESCRIPTION: SEQ ID NO:114:

```
Lys  Ser  Lys  Val  Lys  Ala  Leu  Ile  Gln  Leu  Phe  His  Lys  Lys
1              5                        10
```

( 2 ) INFORMATION FOR SEQ ID NO:115:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.119"

( i x ) FEATURE:
        ( A ) NAME/KEY: Modified-site
        ( B ) LOCATION: 7
        ( C ) OTHER INFORMATION: /label= Substituted-Ala
            / note= "The alanine at position 7 is beta-1-
            naphthyl- substituted."

( i x ) FEATURE:
        ( A ) NAME/KEY: Modified-site
        ( B ) LOCATION: 10
        ( C ) OTHER INFORMATION: /label= Substituted-Ala
            / note= "The alanine at position 10 is beta-1-
            naphthyl- substituted."

( x i ) SEQUENCE DESCRIPTION: SEQ ID NO:115:

```
Ile  Lys  Ile  Ser  Gly  Lys  Ala  Lys  Ala  Ala  Lys  Arg  Phe  Leu  Lys
1              5                        10                       15
```

( 2 ) INFORMATION FOR SEQ ID NO:116:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.120"

( x i ) SEQUENCE DESCRIPTION: SEQ ID NO:116:

```
Ile  Lys  Ile  Ser  Gly  Lys  Trp  Lys  Ala  Gln  Lys  Arg  Lys  Leu  Lys
1              5                        10                       15
```

( 2 ) INFORMATION FOR SEQ ID NO:117:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.121"

( i x ) FEATURE:
        ( A ) NAME/KEY: Modified-site
        ( B ) LOCATION: 10
        ( C ) OTHER INFORMATION: /label= Substituted-Ala
            / note= "The alanine at position 10 is beta-1-
            naphthyl- substituted."

( i x ) FEATURE:
        ( A ) NAME/KEY: Modified-site (B) LOCATION: 11
(C) OTHER INFORMATION: /label= Substituted-Ala
    / note= "The alanine at position 11 is beta-1-
    naphthyl- substituted."

(x i) SEQUENCE DESCRIPTION: SEQ ID NO:117:

```
Ile Lys Ile Ser Gly Lys Trp Lys Ala Ala Ala Arg Phe Leu Lys
1               5                   10                  15
```

(2) INFORMATION FOR SEQ ID NO:118:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.122"

(i x) FEATURE:
        (A) NAME/KEY: Modified-site
        (B) LOCATION: 7
        (C) OTHER INFORMATION: /label= Substituted-Ala
            / note= "The alanine at position 7 is beta-1-
            naphthyl- substituted."

(i x) FEATURE:
        (A) NAME/KEY: Modified-site
        (B) LOCATION: 10
        (C) OTHER INFORMATION: /label= Substituted-Ala
            / note= "The alanine at position 10 is beta-1-
            naphthyl- substituted."

(i x) FEATURE:
        (A) NAME/KEY: Modified-site
        (B) LOCATION: 11
        (C) OTHER INFORMATION: /label= Substituted-Ala
            / note= "The alanine at position 11 is beta-1-
            naphthyl- substituted."

(x i) SEQUENCE DESCRIPTION: SEQ ID NO:118:

```
Ile Lys Ile Ser Gly Lys Ala Lys Ala Ala Ala Arg Phe Leu Lys
1               5                   10                  15
```

(2) INFORMATION FOR SEQ ID NO:119:

(i) SEQUENCE CHARACTERISTICS:
        (A) LENGTH: 14 amino acids
        (B) TYPE: amino acid
        (D) TOPOLOGY: linear (i i) MOLECULE TYPE: peptide (i x) FEATURE:
        (A) NAME/KEY: misc_feature
        (D) OTHER INFORMATION: "XMP.123"

(i x) FEATURE:
        (A) NAME/KEY: Modified-site
        (B) LOCATION: 9
        (C) OTHER INFORMATION: /label= Substituted-Phe
            / note= "The phenylalanine at position 9 is
            p-amino- substituted."

(x i) SEQUENCE DESCRIPTION: SEQ ID NO:119:

```
Lys Ser Lys Val Gly Trp Leu Ile Phe Leu Phe His Lys Lys
1               5                   10
```

(2) INFORMATION FOR SEQ ID NO:120:

(i) SEQUENCE CHARACTERISTICS:

(A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.124"

(xi) SEQUENCE DESCRIPTION: SEQ ID NO:120:

Lys Ser Lys Val Lys Trp Leu Ile Gln Leu Trp His Lys Lys
   1               5                   10

(2) INFORMATION FOR SEQ ID NO:121:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.125"

(xi) SEQUENCE DESCRIPTION: SEQ ID NO:121:

Lys Ser Lys Val Gly Trp Leu Ile Tyr Leu Phe His Lys Lys
   1               5                   10

(2) INFORMATION FOR SEQ ID NO:122:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.126"

(ix) FEATURE:
        (A) NAME/KEY: Modified-site
        (B) LOCATION: 6
        (C) OTHER INFORMATION: /label= D- Trp
            / note= "The amino acid at position 6 is
            D- tryptophan."

(xi) SEQUENCE DESCRIPTION: SEQ ID NO:122:

Lys Ser Lys Val Gly Trp Leu Ile Gln Leu Phe His Lys Lys
   1               5                   10

(2) INFORMATION FOR SEQ ID NO:123:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.127"

(xi) SEQUENCE DESCRIPTION: SEQ ID NO:123:

Lys Ser Lys Val Gly Phe Leu Ile Gln Leu Phe His Lys Lys
   1               5                   10

( 2 ) INFORMATION FOR SEQ ID NO:124:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.128"

( i x ) FEATURE:
        ( A ) NAME/KEY: Modified-site
        ( B ) LOCATION: 6
        ( C ) OTHER INFORMATION: /label= D- Phe
            / note= "The amino acid at position 6 is
            D- phenylalanine."

( x i ) SEQUENCE DESCRIPTION: SEQ ID NO:124:

Lys Ser Lys Val Gly Phe Leu Ile Gln Leu Pro His Lys Lys
1               5                   10

( 2 ) INFORMATION FOR SEQ ID NO:125:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.129"

( i x ) FEATURE:
        ( A ) NAME/KEY: Modified-site
        ( B ) LOCATION: 6
        ( C ) OTHER INFORMATION: /label= Substituted-Ala
            / note= "The alanine at position 6 is
            D-1-beta-1- naphthyl-
            substituted."

( x i ) SEQUENCE DESCRIPTION: SEQ ID NO:125:

Lys Ser Lys Val Gly Ala Leu Ile Gln Leu Phe His Lys Lys
1               5                   10

( 2 ) INFORMATION FOR SEQ ID NO:126:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.130"

( i x ) FEATURE:
        ( A ) NAME/KEY: Modified-site
        ( B ) LOCATION: 6
        ( C ) OTHER INFORMATION: /label= Substituted-Ala
            / note= "The alanine at position 6 is
            2-beta-1- naphthyl-
            substituted."

( x i ) SEQUENCE DESCRIPTION: SEQ ID NO:126:

Lys Ser Lys Val Gly Ala Leu Ile Gln Leu Phe His Lys Lys
1               5                   10

( 2 ) INFORMATION FOR SEQ ID NO:127:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.131"

( i x ) FEATURE:
        ( A ) NAME/KEY: Modified-site
        ( B ) LOCATION: 6
        ( C ) OTHER INFORMATION: /label= Substituted-Ala
            / note= "The alanine at position 6 is
            D-2-beta-1- naphthyl-
            substituted."

( x i ) SEQUENCE DESCRIPTION: SEQ ID NO:127:

Lys  Ser  Lys  Val  Gly  Ala  Leu  Ile  Gln  Leu  Phe  His  Lys  Lys
1                  5                            10

( 2 ) INFORMATION FOR SEQ ID NO:128:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.132"

( i x ) FEATURE:
        ( A ) NAME/KEY: Modified-site
        ( B ) LOCATION: 6
        ( C ) OTHER INFORMATION: /label= Substituted-Ala
            / note= "The alanine at position 6 is
            pyridyl- substituted."

( x i ) SEQUENCE DESCRIPTION: SEQ ID NO:128:

Lys  Ser  Lys  Val  Gly  Ala  Leu  Ile  Gln  Leu  Phe  His  Lys  Lys
1                  5                            10

( 2 ) INFORMATION FOR SEQ ID NO:129:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.133"

( i x ) FEATURE:
        ( A ) NAME/KEY: Modified-site
        ( B ) LOCATION: 6
        ( C ) OTHER INFORMATION: /label= Substituted-Phe
            / note= "The phenylalanine at position 6 is
            para-amino-
            substituted."

( x i ) SEQUENCE DESCRIPTION: SEQ ID NO:129:

Lys  Ser  Lys  Val  Gly  Phe  Leu  Ile  Gln  Leu  Phe  His  Lys  Lys
1                  5                            10

( 2 ) INFORMATION FOR SEQ ID NO:130:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.134"

( i x ) FEATURE:
        ( A ) NAME/KEY: Modified-site
        ( B ) LOCATION: 5
        ( C ) OTHER INFORMATION: /label= Substituted-Phe
            / note= "The phenylalanine at position 5 is
            para-amino- substituted."

( x i ) SEQUENCE DESCRIPTION: SEQ ID NO:130:

Lys Ser Lys Val Phe Trp Leu Ile Gln Leu Phe His Lys Lys
1               5                   10

( 2 ) INFORMATION FOR SEQ ID NO:131:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.135"

( x i ) SEQUENCE DESCRIPTION: SEQ ID NO:131:

Lys Ser Lys Val Gly Lys Leu Ile Gln Leu Pro His Lys Lys
1               5                   10

( 2 ) INFORMATION FOR SEQ ID NO:132:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.136"

( x i ) SEQUENCE DESCRIPTION: SEQ ID NO:132:

Ile Lys Ile Ser Gly Lys Trp Lys Ala Gln Glu Arg Phe Leu Lys
1               5                   10                  15

( 2 ) INFORMATION FOR SEQ ID NO:133:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.137"

( x i ) SEQUENCE DESCRIPTION: SEQ ID NO:133:

Cys Lys Ser Lys Val Gly Trp Leu Ile Gln Leu Phe His Lys Lys Cys (2) INFORMATION FOR SEQ ID NO:134:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.138"

(xi) SEQUENCE DESCRIPTION: SEQ ID NO:134:

```
Lys Ser Lys Val Lys Phe Leu Ile Gln Leu Phe His Lys Lys
1               5                   10
```

(2) INFORMATION FOR SEQ ID NO:135:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.139"

(xi) SEQUENCE DESCRIPTION: SEQ ID NO:135:

```
Lys Ser Lys Val Gly Tyr Leu Ile Gln Leu Phe His Lys Lys
1               5                   10
```

(2) INFORMATION FOR SEQ ID NO:136:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.140"

(ix) FEATURE:
        (A) NAME/KEY: Modified-site
        (B) LOCATION: 1
        (C) OTHER INFORMATION: /label= Substituted-Ala
        / note= "The alanine at position 1 is
        beta-1- naphthyl-substituted."

(ix) FEATURE:
        (A) NAME/KEY: Modified-site
        (B) LOCATION: 2
        (C) OTHER INFORMATION: /label= Substituted-Ala
        / note= "The alanine at position 2 is
        beta-1- naphthyl-substituted."

(xi) SEQUENCE DESCRIPTION: SEQ ID NO:136:

```
Ala Ala Arg Phe Leu Lys Phe
1               5
```

(2) INFORMATION FOR SEQ ID NO:137:

(i) SEQUENCE CHARACTERISTICS:
        (A) LENGTH: 15 amino acids
        (B) TYPE: amino acid
        (D) TOPOLOGY: linear ( i i ) MOLECULE TYPE: peptide ( i x ) FEATURE:
    ( A ) NAME/KEY: misc_feature
    ( D ) OTHER INFORMATION: "XMP.141"

( x i ) SEQUENCE DESCRIPTION: SEQ ID NO:137:

```
Ile Lys Ile Ser Gly Lys Trp Lys Ala Gln Lys Arg Trp Leu Lys
1               5                   10                  15
```

( 2 ) INFORMATION FOR SEQ ID NO:138:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.142"

( x i ) SEQUENCE DESCRIPTION: SEQ ID NO:138:

```
Lys Ser Lys Val Gly Trp Leu Ile Gln Trp Phe His Lys Lys
1               5                   10
```

( 2 ) INFORMATION FOR SEQ ID NO:139:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.143"

( i x ) FEATURE:
        ( A ) NAME/KEY: Modified-site
        ( B ) LOCATION: 10
        ( C ) OTHER INFORMATION: /label= Substituted-Ala
            / note= "The alanine at position 10 is
            beta-1- naphthyl-substituted."

( x i ) SEQUENCE DESCRIPTION: SEQ ID NO:139:

```
Lys Ser Lys Val Gly Trp Leu Ile Gln Ala Phe His Lys Lys
1               5                   10
```

( 2 ) INFORMATION FOR SEQ ID NO:140:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.144"

( i x ) FEATURE:
        ( A ) NAME/KEY: Modified-site
        ( B ) LOCATION: 6
        ( C ) OTHER INFORMATION: /label= Substituted-Ala
            / note= "The alanine at position 6 is
            cyclohexyl- substituted."

( x i ) SEQUENCE DESCRIPTION: SEQ ID NO:140:

```
        Lys  Ser  Lys  Val  Gly  Ala  Leu  Ile  Gln  Leu  Phe  His  Lys  Lys
        1                  5                        10
```

( 2 ) INFORMATION FOR SEQ ID NO:141:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.145"

( x i ) SEQUENCE DESCRIPTION: SEQ ID NO:141:

```
        Lys  Trp  Lys  Ala  Ala  Ala  Arg  Phe  Leu  Lys  Lys  Ser  Lys  Val  Gly  Trp
        1                  5                        10                         15

Leu  Ile  Gln  Leu  Phe  His  Lys  Lys
                            20
```

( 2 ) INFORMATION FOR SEQ ID NO:142:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.146"

( i x ) FEATURE:
        ( A ) NAME/KEY: Modified-site
        ( B ) LOCATION: 12
        ( C ) OTHER INFORMATION: /label= Substituted-Ala
            / note= "The alanine at position 12 is
            beta-1- naphthyl-substituted."

( i x ) FEATURE:
        ( A ) NAME/KEY: Modified-site
        ( B ) LOCATION: 14
        ( C ) OTHER INFORMATION: /label= Substituted-Ala
            / note= "The alanine at position 14 is
            beta-1- naphthyl-substituted."

( x i ) SEQUENCE DESCRIPTION: SEQ ID NO:142:

```
        Lys  Ser  Lys  Val  Gly  Trp  Leu  Ile  Gln  Leu  Phe  Ala  Lys  Ala
        1                  5                        10
```

( 2 ) INFORMATION FOR SEQ ID NO:143:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.147"

( x i ) SEQUENCE DESCRIPTION: SEQ ID NO:143:

```
        Ile  Lys  Ile  Ser  Gly  Lys  Trp  Lys  Ala  Glu  Lys  Lys  Phe  Leu  Lys
        1                  5                        10                         15
```

( 2 ) INFORMATION FOR SEQ ID NO:144:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.148"

( i x ) FEATURE:
  ( A ) NAME/KEY: Modified-site
  ( B ) LOCATION: 6
  ( C ) OTHER INFORMATION: /label= Substituted-Ala
    / note= "The alanine at position 6 is
    beta-1- naphthyl-substituted."

( i x ) FEATURE:
  ( A ) NAME/KEY: Modified-site
  ( B ) LOCATION: 12
  ( C ) OTHER INFORMATION: /label= Substituted-Ala
    / note= "The alanine at position 12 is
    beta-1- naphthyl-substituted."

( x i ) SEQUENCE DESCRIPTION: SEQ ID NO:144:

```
Lys  Ser  Lys  Val  Gly  Ala  Leu  Ile  Gln  Leu  Phe  Ala  Lys  Lys
1              5                        10
```

( 2 ) INFORMATION FOR SEQ ID NO:145:

( i ) SEQUENCE CHARACTERISTICS:
  ( A ) LENGTH: 1813 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 31..1491

( i x ) FEATURE:
  ( A ) NAME/KEY: mat_peptide
  ( B ) LOCATION: 124..1491

( i x ) FEATURE:
  ( A ) NAME/KEY: misc_feature
  ( D ) OTHER INFORMATION: "rBPI"

( x i ) SEQUENCE DESCRIPTION: SEQ ID NO:145:

```
CAGGCCTTGA GGTTTTGGCA GCTCTGGAGG ATG AGA GAG AAC ATG GCC AGG GGC        54
                                Met Arg Glu Asn Met Ala Arg Gly
                                -31 -30                     -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20             -15                     -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
10              15                  20                      25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
                30                  35                      40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
                45                  50                      55

ATC CGT GAA TTC CAG CTT CCC AGT TCC CAG ATA AGC ATG GTG CCC AAT        342
```

```
Ile Arg Glu Phe Gln Leu Pro Ser Ser Gln Ile Ser Met Val Pro Asn
        60              65              70

GTG GGC CTT AAG TTC TCC ATC AGC AAC GCC AAT ATC AAG ATC AGC GGG    390
Val Gly Leu Lys Phe Ser Ile Ser Asn Ala Asn Ile Lys Ile Ser Gly
    75              80              85

AAA TGG AAG GCA CAA AAG AGA TTC TTA AAA ATG AGC GGC AAT TTT GAC    438
Lys Trp Lys Ala Gln Lys Arg Phe Leu Lys Met Ser Gly Asn Phe Asp
90              95              100             105

CTG AGC ATA GAA GGC ATG TCC ATT TCG GCT GAT CTG AAG CTG GGC AGT    486
Leu Ser Ile Glu Gly Met Ser Ile Ser Ala Asp Leu Lys Leu Gly Ser
                110             115             120

AAC CCC ACG TCA GGC AAG CCC ACC ATC ACC TGC TCC AGC TGC AGC AGC    534
Asn Pro Thr Ser Gly Lys Pro Thr Ile Thr Cys Ser Ser Cys Ser Ser
            125             130             135

CAC ATC AAC AGT GTC CAC GTG CAC ATC TCA AAG AGC AAA GTC GGG TGG    582
His Ile Asn Ser Val His Val His Ile Ser Lys Ser Lys Val Gly Trp
        140             145             150

CTG ATC CAA CTC TTC CAC AAA AAA ATT GAG TCT GCG CTT CGA AAC AAG    630
Leu Ile Gln Leu Phe His Lys Lys Ile Glu Ser Ala Leu Arg Asn Lys
    155             160             165

ATG AAC AGC CAG GTC TGC GAG AAA GTG ACC AAT TCT GTA TCC TCC AAG    678
Met Asn Ser Gln Val Cys Glu Lys Val Thr Asn Ser Val Ser Ser Lys
170             175             180             185

CTG CAA CCT TAT TTC CAG ACT CTG CCA GTA ATG ACC AAA ATA GAT TCT    726
Leu Gln Pro Tyr Phe Gln Thr Leu Pro Val Met Thr Lys Ile Asp Ser
                190             195             200

GTG GCT GGA ATC AAC TAT GGT CTG GTG GCA CCT CCA GCA ACC ACG GCT    774
Val Ala Gly Ile Asn Tyr Gly Leu Val Ala Pro Pro Ala Thr Thr Ala
            205             210             215

GAG ACC CTG GAT GTA CAG ATG AAG GGG GAG TTT TAC AGT GAG AAC CAC    822
Glu Thr Leu Asp Val Gln Met Lys Gly Glu Phe Tyr Ser Glu Asn His
        220             225             230

CAC AAT CCA CCT CCC TTT GCT CCA CCA GTG ATG GAG TTT CCC GCT GCC    870
His Asn Pro Pro Pro Phe Ala Pro Pro Val Met Glu Phe Pro Ala Ala
    235             240             245

CAT GAC CGC ATG GTA TAC CTG GGC CTC TCA GAC TAC TTC TTC AAC ACA    918
His Asp Arg Met Val Tyr Leu Gly Leu Ser Asp Tyr Phe Phe Asn Thr
250             255             260             265

GCC GGG CTT GTA TAC CAA GAG GCT GGG GTC TTG AAG ATG ACC CTT AGA    966
Ala Gly Leu Val Tyr Gln Glu Ala Gly Val Leu Lys Met Thr Leu Arg
                270             275             280

GAT GAC ATG ATT CCA AAG GAG TCC AAA TTT CGA CTG ACA ACC AAG TTC    1014
Asp Asp Met Ile Pro Lys Glu Ser Lys Phe Arg Leu Thr Thr Lys Phe
            285             290             295

TTT GGA ACC TTC CTA CCT GAG GTG GCC AAG AAG TTT CCC AAC ATG AAG    1062
Phe Gly Thr Phe Leu Pro Glu Val Ala Lys Lys Phe Pro Asn Met Lys
        300             305             310

ATA CAG ATC CAT GTC TCA GCC TCC ACC CCG CCA CAC CTG TCT GTG CAG    1110
Ile Gln Ile His Val Ser Ala Ser Thr Pro Pro His Leu Ser Val Gln
    315             320             325

CCC ACC GGC CTT ACC TTC TAC CCT GCC GTG GAT GTC CAG GCC TTT GCC    1158
Pro Thr Gly Leu Thr Phe Tyr Pro Ala Val Asp Val Gln Ala Phe Ala
330             335             340             345

GTC CTC CCC AAC TCC TCC CTG GCT TCC CTC TTC CTG ATT GGC ATG CAC    1206
Val Leu Pro Asn Ser Ser Leu Ala Ser Leu Phe Leu Ile Gly Met His
                350             355             360

ACA ACT GGT TCC ATG GAG GTC AGC GCC GAG TCC AAC AGG CTT GTT GGA    1254
Thr Thr Gly Ser Met Glu Val Ser Ala Glu Ser Asn Arg Leu Val Gly
            365             370             375

GAG CTC AAG CTG GAT AGG CTG CTC CTG GAA CTG AAG CAC TCA AAT ATT    1302
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Glu | Leu | Lys | Leu | Asp | Arg | Leu | Leu | Leu | Glu | Leu | Lys | His | Ser | Asn | Ile  |
|     | 380 |     |     |     |     |     | 385 |     |     |     | 390 |     |     |     |      |
| GGC | CCC | TTC | CCG | GTT | GAA | TTG | CTG | CAG | GAT | ATC | ATG | AAC | TAC | ATT | GTA  | 1350 |
| Gly | Pro | Phe | Pro | Val | Glu | Leu | Leu | Gln | Asp | Ile | Met | Asn | Tyr | Ile | Val  |
|     | 395 |     |     |     | 400 |     |     |     |     | 405 |     |     |     |     |      |
| CCC | ATT | CTT | GTG | CTG | CCC | AGG | GTT | AAC | GAG | AAA | CTA | CAG | AAA | GGC | TTC  | 1398 |
| Pro | Ile | Leu | Val | Leu | Pro | Arg | Val | Asn | Glu | Lys | Leu | Gln | Lys | Gly | Phe  |
| 410 |     |     |     |     | 415 |     |     |     |     | 420 |     |     |     |     | 425  |
| CCT | CTC | CCG | ACG | CCG | GCC | AGA | GTC | CAG | CTC | TAC | AAC | GTA | GTG | CTT | CAG  | 1446 |
| Pro | Leu | Pro | Thr | Pro | Ala | Arg | Val | Gln | Leu | Tyr | Asn | Val | Val | Leu | Gln  |
|     |     |     |     | 430 |     |     |     |     | 435 |     |     |     |     | 440 |      |
| CCT | CAC | CAG | AAC | TTC | CTG | CTG | TTC | GGT | GCA | GAC | GTT | GTC | TAT | AAA |      | 1491 |
| Pro | His | Gln | Asn | Phe | Leu | Leu | Phe | Gly | Ala | Asp | Val | Val | Tyr | Lys |      |
|     |     |     | 445 |     |     |     |     | 450 |     |     |     |     | 455 |     |      |

```
TGAAGGCACC  AGGGGTGCCG  GGGGCTGTCA  GCCGCACCTG  TTCCTGATGG  GCTGTGGGGC       1551
ACCGGCTGCC  TTTCCCCAGG  GAATCCTCTC  CAGATCTTAA  CCAAGAGCCC  CTTGCAAACT       1611
TCTTCGACTC  AGATTCAGAA  ATGATCTAAA  CACGAGGAAA  CATTATTCAT  TGGAAAAGTG       1671
CATGGTGTGT  ATTTTAGGGA  TTATGAGCTT  CTTTCAAGGG  CTAAGGCTGC  AGAGATATTT       1731
CCTCCAGGAA  TCGTGTTTCA  ATTGTAACCA  AGAAATTTCC  ATTTGTGCTT  CATGAAAAAA       1791
AACTTCTGGT  TTTTTTCATG  TG                                                   1813
```

( 2 ) INFORMATION FOR SEQ ID NO:146:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:146:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Arg | Glu | Asn | Met | Ala | Arg | Gly | Pro | Cys | Asn | Ala | Pro | Arg | Trp | Val |
| -31 | -30 |     |     |     | -25 |     |     |     |     | -20 |     |     |     |     |     |
| Ser | Leu | Met | Val | Leu | Val | Ala | Ile | Gly | Thr | Ala | Val | Thr | Ala | Ala | Val |
| -15 |     |     |     |     | -10 |     |     |     |     | -5  |     |     |     |     | 1   |
| Asn | Pro | Gly | Val | Val | Val | Arg | Ile | Ser | Gln | Lys | Gly | Leu | Asp | Tyr | Ala |
|     |     |     | 5   |     |     |     |     | 10  |     |     |     |     | 15  |     |     |
| Ser | Gln | Gln | Gly | Thr | Ala | Ala | Leu | Gln | Lys | Glu | Leu | Lys | Arg | Ile | Lys |
|     |     | 20  |     |     |     |     | 25  |     |     |     |     | 30  |     |     |     |
| Ile | Pro | Asp | Tyr | Ser | Asp | Ser | Phe | Lys | Ile | Lys | His | Leu | Gly | Lys | Gly |
|     | 35  |     |     |     | 40  |     |     |     |     | 45  |     |     |     |     |     |
| His | Tyr | Ser | Phe | Tyr | Ser | Met | Asp | Ile | Arg | Glu | Phe | Gln | Leu | Pro | Ser |
| 50  |     |     |     |     | 55  |     |     |     |     | 60  |     |     |     |     | 65  |
| Ser | Gln | Ile | Ser | Met | Val | Pro | Asn | Val | Gly | Leu | Lys | Phe | Ser | Ile | Ser |
|     |     |     |     | 70  |     |     |     |     | 75  |     |     |     |     | 80  |     |
| Asn | Ala | Asn | Ile | Lys | Ile | Ser | Gly | Lys | Trp | Lys | Ala | Gln | Lys | Arg | Phe |
|     |     |     | 85  |     |     |     |     | 90  |     |     |     |     | 95  |     |     |
| Leu | Lys | Met | Ser | Gly | Asn | Phe | Asp | Leu | Ser | Ile | Glu | Gly | Met | Ser | Ile |
|     |     | 100 |     |     |     |     | 105 |     |     |     |     | 110 |     |     |     |
| Ser | Ala | Asp | Leu | Lys | Leu | Gly | Ser | Asn | Pro | Thr | Ser | Gly | Lys | Pro | Thr |
|     | 115 |     |     |     |     | 120 |     |     |     |     | 125 |     |     |     |     |
| Ile | Thr | Cys | Ser | Ser | Cys | Ser | Ser | His | Ile | Asn | Ser | Val | His | Val | His |
| 130 |     |     |     |     | 135 |     |     |     |     | 140 |     |     |     |     | 145 |
| Ile | Ser | Lys | Ser | Lys | Val | Gly | Trp | Leu | Ile | Gln | Leu | Phe | His | Lys | Lys |
|     |     |     | 150 |     |     |     |     | 155 |     |     |     |     | 160 |     |     |
| Ile | Glu | Ser | Ala | Leu | Arg | Asn | Lys | Met | Asn | Ser | Gln | Val | Cys | Glu | Lys |

```
                              165                      170                      175
Val  Thr  Asn  Ser  Val  Ser  Ser  Lys  Leu  Gln  Pro  Tyr  Phe  Gln  Thr  Leu
               180                      185                      190

Pro  Val  Met  Thr  Lys  Ile  Asp  Ser  Val  Ala  Gly  Ile  Asn  Tyr  Gly  Leu
     195                      200                      205

Val  Ala  Pro  Pro  Ala  Thr  Thr  Ala  Glu  Thr  Leu  Asp  Val  Gln  Met  Lys
210                      215                      220                      225

Gly  Glu  Phe  Tyr  Ser  Glu  Asn  His  His  Asn  Pro  Pro  Pro  Phe  Ala  Pro
               230                      235                      240

Pro  Val  Met  Glu  Phe  Pro  Ala  Ala  His  Asp  Arg  Met  Val  Tyr  Leu  Gly
               245                      250                      255

Leu  Ser  Asp  Tyr  Phe  Phe  Asn  Thr  Ala  Gly  Leu  Val  Tyr  Gln  Glu  Ala
          260                      265                      270

Gly  Val  Leu  Lys  Met  Thr  Leu  Arg  Asp  Asp  Met  Ile  Pro  Lys  Glu  Ser
     275                      280                      285

Lys  Phe  Arg  Leu  Thr  Thr  Lys  Phe  Phe  Gly  Thr  Phe  Leu  Pro  Glu  Val
290                      295                      300                      305

Ala  Lys  Lys  Phe  Pro  Asn  Met  Lys  Ile  Gln  Ile  His  Val  Ser  Ala  Ser
               310                      315                      320

Thr  Pro  Pro  His  Leu  Ser  Val  Gln  Pro  Thr  Gly  Leu  Thr  Phe  Tyr  Pro
               325                      330                      335

Ala  Val  Asp  Val  Gln  Ala  Phe  Ala  Val  Leu  Pro  Asn  Ser  Ser  Leu  Ala
               340                      345                      350

Ser  Leu  Phe  Leu  Ile  Gly  Met  His  Thr  Thr  Gly  Ser  Met  Glu  Val  Ser
     355                      360                      365

Ala  Glu  Ser  Asn  Arg  Leu  Val  Gly  Glu  Leu  Lys  Leu  Asp  Arg  Leu  Leu
370                      375                      380                      385

Leu  Glu  Leu  Lys  His  Ser  Asn  Ile  Gly  Pro  Phe  Pro  Val  Glu  Leu  Leu
               390                      395                      400

Gln  Asp  Ile  Met  Asn  Tyr  Ile  Val  Pro  Ile  Leu  Val  Leu  Pro  Arg  Val
               405                      410                      415

Asn  Glu  Lys  Leu  Gln  Lys  Gly  Phe  Pro  Leu  Pro  Thr  Pro  Ala  Arg  Val
               420                      425                      430

Gln  Leu  Tyr  Asn  Val  Val  Leu  Gln  Pro  His  Gln  Asn  Phe  Leu  Leu  Phe
     435                      440                      445

Gly  Ala  Asp  Val  Val  Tyr  Lys
450                      455
```

( 2 ) INFORMATION FOR SEQ ID NO:147:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.149"

( x i ) SEQUENCE DESCRIPTION: SEQ ID NO:147:

```
Lys  Trp  Lys  Val  Phe  Lys  Lys  Ile  Glu  Lys  Lys  Ser  Lys  Val  Gly  Trp
1              5                        10                       15

Leu  Ile  Gln  Leu  Phe  His  Lys  Lys
               20
```

( 2 ) INFORMATION FOR SEQ ID NO:148:

( i ) SEQUENCE CHARACTERISTICS:
  ( A ) LENGTH: 20 amino acids
  ( B ) TYPE: amino acid
  ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.150"

( x i ) SEQUENCE DESCRIPTION: SEQ ID NO:148:

Lys Trp Ala Phe Ala Lys Lys Gln Lys Lys Arg Leu Lys Arg Gln Trp
1               5                   10                  15

Leu Lys Lys Phe
            20

( 2 ) INFORMATION FOR SEQ ID NO:149:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.153"

( x i ) SEQUENCE DESCRIPTION: SEQ ID NO:149:

Lys Trp Lys Ala Gln Lys Arg Phe Leu Lys Lys Trp Lys Ala Gln Lys
1               5                   10                  15

Arg Phe Leu Lys Lys Trp Lys Ala Gln Lys Arg Phe Leu Lys
            20                  25                  30

( 2 ) INFORMATION FOR SEQ ID NO:150:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.154"

( i x ) FEATURE:
    ( A ) NAME/KEY: Modified-site
    ( B ) LOCATION: 5
    ( C ) OTHER INFORMATION: /label= Substituted-Ala
      / note= "Position 5 is
      beta-1- naphthyl-substituted."

( i x ) FEATURE:
    ( A ) NAME/KEY: Modified-site
    ( B ) LOCATION: 6
    ( C ) OTHER INFORMATION: /label= Substituted-Ala
      / note= "Position 6 is
      beta-1- naphthyl-substituted."

( x i ) SEQUENCE DESCRIPTION: SEQ ID NO:150:

Lys Trp Lys Ala Ala Ala Arg Phe Leu Lys Lys Trp Lys Ala Gln Lys
1               5                   10                  15

Arg Phe Leu Lys
            20

( 2 ) INFORMATION FOR SEQ ID NO:151:

( i ) SEQUENCE CHARACTERISTICS:
   ( A ) LENGTH: 20 amino acids
   ( B ) TYPE: amino acid
   ( D ) TOPOLOGY: linear ( i i ) MOLECULE TYPE: peptide ( i x ) FEATURE:
   ( A ) NAME/KEY: misc_feature
   ( D ) OTHER INFORMATION: "XMP.155"

( i x ) FEATURE:
   ( A ) NAME/KEY: Modified-site
   ( B ) LOCATION: 15
   ( C ) OTHER INFORMATION: /label= Substituted-Ala
       / note= "Position 15 is
       beta-1- naphthyl-substituted."

( i x ) FEATURE:
   ( A ) NAME/KEY: Modified-site
   ( B ) LOCATION: 16
   ( C ) OTHER INFORMATION: /label= Substituted-Ala
       / note= "Position 16 is
       beta-1- naphthyl-substituted."

( x i ) SEQUENCE DESCRIPTION: SEQ ID NO:151:

Lys Trp Lys Ala Gln Lys Arg Phe Leu Lys Lys Trp Lys Ala Ala Ala
1               5                   10                  15

Arg Phe Leu Lys
            20

( 2 ) INFORMATION FOR SEQ ID NO:152:

( i ) SEQUENCE CHARACTERISTICS:
   ( A ) LENGTH: 20 amino acids
   ( B ) TYPE: amino acid
   ( D ) TOPOLOGY: linear ( i i ) MOLECULE TYPE: peptide ( i x ) FEATURE:
   ( A ) NAME/KEY: misc_feature
   ( D ) OTHER INFORMATION: "XMP.156"

( i x ) FEATURE:
   ( A ) NAME/KEY: Modified-site
   ( B ) LOCATION: 5
   ( C ) OTHER INFORMATION: /label= Substituted-Ala
       / note= "Position 5 is
       beta-1- naphthyl-substituted."

( i x ) FEATURE:
   ( A ) NAME/KEY: Modified-site
   ( B ) LOCATION: 6
   ( C ) OTHER INFORMATION: /label= Substituted-Ala
       / note= "Position 6 is
       beta-1- naphthyl-substituted."

( i x ) FEATURE:
   ( A ) NAME/KEY: Modified-site
   ( B ) LOCATION: 15
   ( C ) OTHER INFORMATION: /label= Substituted-Ala
       / note= "Position 15 is
       beta-1- naphthyl-substituted."

( i x ) FEATURE:
   ( A ) NAME/KEY: Modified-site
   ( B ) LOCATION: 16
   ( C ) OTHER INFORMATION: /label= Substituted-Ala
       / note= "Position 16 is
       beta-1- naphthyl-substituted."

( x i ) SEQUENCE DESCRIPTION: SEQ ID NO:152:

Lys Trp Lys Ala Ala Ala Arg Phe Leu Lys Lys Trp Lys Ala Ala Ala
1               5                   10                  15

Arg Phe Leu Lys
            20

( 2 ) INFORMATION FOR SEQ ID NO:153:

( i ) SEQUENCE CHARACTERISTICS:
            ( A ) LENGTH: 30 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.157"

( i x ) FEATURE:
            ( A ) NAME/KEY: Modified-site
            ( B ) LOCATION: 5
            ( C ) OTHER INFORMATION: /label= Substituted-Ala
                    / note= "Position 5 is
                    beta-1- naphthyl-substituted."

( i x ) FEATURE:
            ( A ) NAME/KEY: Modified-site
            ( B ) LOCATION: 6
            ( C ) OTHER INFORMATION: /label= Substituted-Ala
                    / note= "Position 6 is
                    beta-1- naphthyl-substituted."

( i x ) FEATURE:
            ( A ) NAME/KEY: Modified-site
            ( B ) LOCATION: 15
            ( C ) OTHER INFORMATION: /label= Substituted-Ala
                    / note= "Position 15 is
                    beta-1- naphthyl-substituted."

( i x ) FEATURE:
            ( A ) NAME/KEY: Modified-site
            ( B ) LOCATION: 16
            ( C ) OTHER INFORMATION: /label= Substituted-Ala
                    / note= "Position 16 is
                    beta-1- naphthyl-substituted."

( i x ) FEATURE:
            ( A ) NAME/KEY: Modified-site
            ( B ) LOCATION: 25
            ( C ) OTHER INFORMATION: /label= Substituted-Ala
                    / note= "Position 25 is
                    beta-1- naphthyl-substituted."

( i x ) FEATURE:
            ( A ) NAME/KEY: Modified-site
            ( B ) LOCATION: 26
            ( C ) OTHER INFORMATION: /label= Substituted-Ala
                    / note= "Position 26 is
                    beta-1- naphthyl-substituted."

( x i ) SEQUENCE DESCRIPTION: SEQ ID NO:153:

Lys Trp Lys Ala Ala Ala Arg Phe Leu Lys Lys Trp Lys Ala Ala Ala
1               5                   10                  15

Arg Phe Leu Lys Lys Trp Lys Ala Ala Ala Arg Phe Leu Lys
            20                  25                  30

( 2 ) INFORMATION FOR SEQ ID NO:154:

( i ) SEQUENCE CHARACTERISTICS:
            ( A ) LENGTH: 29 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature ( D ) OTHER INFORMATION: "XMP.158"

( i x ) FEATURE:
  ( A ) NAME/KEY: Modified-site
  ( B ) LOCATION: 10
  ( C ) OTHER INFORMATION: /label= Substituted-Ala
    / note= "Position 10 is
    beta-1- naphthyl-substituted."

( i x ) FEATURE:
  ( A ) NAME/KEY: Modified-site
  ( B ) LOCATION: 11
  ( C ) OTHER INFORMATION: /label= Substituted-Ala
    / note= "Position 11 is
    beta-1- naphthyl-substituted."

( x i ) SEQUENCE DESCRIPTION: SEQ ID NO:154:

```
Ile Lys Ile Ser Gly Lys Trp Lys Ala Ala Ala Arg Phe Leu Lys Lys
1               5                   10                  15
Ser Lys Val Gly Trp Leu Ile Gln Leu Phe His Lys Lys
            20                  25
```

( 2 ) INFORMATION FOR SEQ ID NO:155:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.159"

( i x ) FEATURE:
    ( A ) NAME/KEY: Modified-site
    ( B ) LOCATION: 2
    ( C ) OTHER INFORMATION: /label= Substituted-Ala
      / note= "Position 2 is
      beta-1- naphthyl-substituted."

( i x ) FEATURE:
    ( A ) NAME/KEY: Modified-site
    ( B ) LOCATION: 6
    ( C ) OTHER INFORMATION: /label= Substituted-Ala
      / note= "Position 6 is
      beta-1- naphthyl-substituted."

( x i ) SEQUENCE DESCRIPTION: SEQ ID NO:155:

```
Lys Ala Lys Ala Gln Ala Arg Phe Leu Lys Lys Ser Lys Val Gly Trp
1               5                   10                  15
Leu Ile Gln Leu Trp His Lys Lys
            20
```

( 2 ) INFORMATION FOR SEQ ID NO:156:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.160"

( i x ) FEATURE:
    ( A ) NAME/KEY: Modified-site
    ( B ) LOCATION: 2
    ( C ) OTHER INFORMATION: /label= Substituted-Ala
      / note= "Position 2 is
      beta-1- naphthyl-substituted."

( i x ) FEATURE:
    ( A ) NAME/KEY: Modified-site
    ( B ) LOCATION: 6
    ( C ) OTHER INFORMATION: /label= Substituted-Ala
        / note= "Position 6 is
        beta-1- naphthyl-substituted."

( i x ) FEATURE:
    ( A ) NAME/KEY: Modified-site
    ( B ) LOCATION: 12
    ( C ) OTHER INFORMATION: /label= Substituted-Ala
        / note= "Position 12 is
        beta-1- naphthyl-substituted."

( i x ) FEATURE:
    ( A ) NAME/KEY: Modified-site
    ( B ) LOCATION: 16
    ( C ) OTHER INFORMATION: /label= Substituted-Ala
        / note= "Position 16 is
        beta-1- naphthyl-substituted."

( x i ) SEQUENCE DESCRIPTION: SEQ ID NO:156:

```
Lys  Ala  Lys  Ala  Gln  Ala  Arg  Phe  Leu  Lys  Lys  Ala  Lys  Ala  Gln  Ala
1                  5                       10                      15
Arg  Phe  Leu  Lys
              20
```

( 2 ) INFORMATION FOR SEQ ID NO:157:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.161"

( x i ) SEQUENCE DESCRIPTION: SEQ ID NO:157:

```
Lys  Ser  Lys  Val  Lys  Ala  Leu  Ile  Gln  Leu  Phe  His  Lys  Lys
1                  5                       10
```

( 2 ) INFORMATION FOR SEQ ID NO:158:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.162"

( x i ) SEQUENCE DESCRIPTION: SEQ ID NO:158:

```
Lys  Trp  Lys  Ala  Gln  Trp  Arg  Phe  Leu  Lys  Lys  Ser  Lys  Val  Gly  Trp
1                  5                       10                      15
Leu  Ile  Gln  Leu  Phe  His  Lys  Lys
              20
```

( 2 ) INFORMATION FOR SEQ ID NO:159:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.163"

( x i ) SEQUENCE DESCRIPTION: SEQ ID NO:159:

```
Lys Trp Lys Ala Gln Trp Arg Phe Leu Lys Lys Trp Lys Ala Gln Trp
1               5                   10                  15
Arg Phe Leu Lys
            20
```

( 2 ) INFORMATION FOR SEQ ID NO:160:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.164"

( i x ) FEATURE:
        ( A ) NAME/KEY: Modified-site
        ( B ) LOCATION: 5
        ( C ) OTHER INFORMATION: /label= Substituted-Ala
            / note= "Position 5 is
            beta-1- naphthyl-substituted."

( i x ) FEATURE:
        ( A ) NAME/KEY: Modified-site
        ( B ) LOCATION: 15
        ( C ) OTHER INFORMATION: /label= Substituted-Ala
            / note= "Position 15 is
            beta-1- naphthyl-substituted."

( x i ) SEQUENCE DESCRIPTION: SEQ ID NO:160:

```
Lys Trp Lys Ala Ala Lys Arg Phe Leu Lys Lys Trp Lys Ala Ala Lys
1               5                   10                  15
Arg Phe Leu Lys
            20
```

( 2 ) INFORMATION FOR SEQ ID NO:161:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.165"

( i x ) FEATURE:
        ( A ) NAME/KEY: Modified-site
        ( B ) LOCATION: 2
        ( C ) OTHER INFORMATION: /label= Substituted-Ala
            / note= "Position 2 is
            beta-1- naphthyl-substituted."

( i x ) FEATURE:
        ( A ) NAME/KEY: Modified-site
        ( B ) LOCATION: 12
        ( C ) OTHER INFORMATION: /label= Substituted-Ala
            / note= "Position 12 is
            beta-1- naphthyl-substituted."

( x i ) SEQUENCE DESCRIPTION: SEQ ID NO:161:

```
Lys Ala Lys Ala Gln Phe Arg Phe Leu Lys Lys Ala Lys Ala Gln Phe
```

```
        1               5                    10                   15
```

Arg Phe Leu Lys
                 20

( 2 ) INFORMATION FOR SEQ ID NO:162:

( i ) SEQUENCE CHARACTERISTICS:
            ( A ) LENGTH: 14 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.166"

( x i ) SEQUENCE DESCRIPTION: SEQ ID NO:162:

Lys Ser Lys Val Gly Val Leu Ile Gln Leu Phe His Lys Lys
    1               5                   10

( 2 ) INFORMATION FOR SEQ ID NO:163:

( i ) SEQUENCE CHARACTERISTICS:
            ( A ) LENGTH: 8 amino acids
            ( B ) TYPE: amino acid
            ( D ) TOPOLOGY: linear ( i i ) MOLECULE TYPE: peptide ( i x ) FEATURE:
            ( A ) NAME/KEY: misc_feature
            ( D ) OTHER INFORMATION: "XMP.167"

( x i ) SEQUENCE DESCRIPTION: SEQ ID NO:163:

Lys Trp Lys Ala Gln Lys Arg Phe
    1               5

( 2 ) INFORMATION FOR SEQ ID NO:164:

( i ) SEQUENCE CHARACTERISTICS:
            ( A ) LENGTH: 14 amino acids
            ( B ) TYPE: amino acid
            ( D ) TOPOLOGY: circular ( i i ) MOLECULE TYPE: peptide ( i x ) FEATURE:
            ( A ) NAME/KEY: misc_feature
            ( D ) OTHER INFORMATION: "XMP.168"

( x i ) SEQUENCE DESCRIPTION: SEQ ID NO:164:

Cys Lys Trp Lys Ala Gln Lys Arg Phe Leu Lys Met Ser Cys
    1               5                   10

( 2 ) INFORMATION FOR SEQ ID NO:165:

( i ) SEQUENCE CHARACTERISTICS:
            ( A ) LENGTH: 10 amino acids
            ( B ) TYPE: amino acid
            ( D ) TOPOLOGY: circular ( i i ) MOLECULE TYPE: peptide ( i x ) FEATURE:
            ( A ) NAME/KEY: misc_feature
            ( D ) OTHER INFORMATION: "XMP.169"

( x i ) SEQUENCE DESCRIPTION: SEQ ID NO:165:

Cys Lys Trp Lys Ala Gln Lys Arg Phe Cys
    1               5                   10

( 2 ) INFORMATION FOR SEQ ID NO:166:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.221"

( i x ) FEATURE:
        ( A ) NAME/KEY: Modified-site
        ( B ) LOCATION: 13
        ( C ) OTHER INFORMATION: /label= Substituted-Ala
            / note= "Position 13 is
            beta-1- naphthyl-substituted."

( x i ) SEQUENCE DESCRIPTION: SEQ ID NO:166:

```
Ile Lys Ile Ser Gly Lys Trp Lys Ala Gln Lys Arg Ala Leu Lys
1               5                   10                  15
```

( 2 ) INFORMATION FOR SEQ ID NO:167:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.222"

( i x ) FEATURE:
        ( A ) NAME/KEY: Modified-site
        ( B ) LOCATION: 6
        ( C ) OTHER INFORMATION: /label= Substituted-Ala
            / note= "Position 6 is
            beta-1- naphthyl-substituted."

( i x ) FEATURE:
        ( A ) NAME/KEY: Modified-site
        ( B ) LOCATION: 14
        ( C ) OTHER INFORMATION: /label= Substituted-Ala
            / note= "Position 14 is
            beta-1- naphthyl-substituted."

( x i ) SEQUENCE DESCRIPTION: SEQ ID NO:167:

```
Lys Ser Lys Val Gly Ala Leu Ile Gln Leu Phe His Lys Ala
1               5                   10
```

( 2 ) INFORMATION FOR SEQ ID NO:168:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.223"

( i x ) FEATURE:
        ( A ) NAME/KEY: Modified-site
        ( B ) LOCATION: 6
        ( C ) OTHER INFORMATION: /label= Substituted-Ala
            / note= "Position 6 is
            beta-1- naphthyl-substituted."

( i x ) FEATURE:
    ( A ) NAME/KEY: Modified-site
    ( B ) LOCATION: 10
    ( C ) OTHER INFORMATION: /label= Substituted-Ala
        / note= "Position 10 is
        beta-1- naphthyl-substituted."

( x i ) SEQUENCE DESCRIPTION: SEQ ID NO:168:

```
Lys Ser Lys Val Gly Ala Leu Ile Gln Ala Phe His Lys Lys
1               5                   10
```

( 2 ) INFORMATION FOR SEQ ID NO:169:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.224"

( i x ) FEATURE:
        ( A ) NAME/KEY: Modified-site
        ( B ) LOCATION: 6
        ( C ) OTHER INFORMATION: /label= Substituted-Ala
            / note= "Position 6 is
            beta-1- naphthyl-substituted."

( i x ) FEATURE:
        ( A ) NAME/KEY: Modified-site
        ( B ) LOCATION: 9
        ( C ) OTHER INFORMATION: /label= Substituted-Phe
            / note= "Position 9 is
            para-amino- substituted."

( x i ) SEQUENCE DESCRIPTION: SEQ ID NO:169:

```
Lys Ser Lys Val Gly Ala Leu Ile Phe Leu Phe His Lys Lys
1               5                   10
```

( 2 ) INFORMATION FOR SEQ ID NO:170:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.225"

( i x ) FEATURE:
        ( A ) NAME/KEY: Modified-site
        ( B ) LOCATION: 6
        ( C ) OTHER INFORMATION: /label= Substituted-Ala
            / note= "Position 6 is
            beta-1- naphthyl-substituted."

( i x ) FEATURE:
        ( A ) NAME/KEY: Modified-site
        ( B ) LOCATION: 5
        ( C ) OTHER INFORMATION: /label= Substituted-Phe
            / note= "Position 5 is
            para-amino- substituted."

( x i ) SEQUENCE DESCRIPTION: SEQ ID NO:170:

```
Lys Ser Lys Val Phe Ala Leu Ile Gln Leu Phe His Lys Lys
1               5                   10
```

( 2 ) INFORMATION FOR SEQ ID NO:171:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.226"

( i x ) FEATURE:
    ( A ) NAME/KEY: Modified-site
    ( B ) LOCATION: 6
    ( C ) OTHER INFORMATION: /label= Substituted-Ala
      / note= "Position 6 is
      beta-1- naphthyl-substituted."

( x i ) SEQUENCE DESCRIPTION: SEQ ID NO:171:

Lys Ser Lys Val Gly Ala Leu Ile Gln Leu Trp His Lys Lys
1      5          10

( 2 ) INFORMATION FOR SEQ ID NO:172:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.227"

( i x ) FEATURE:
    ( A ) NAME/KEY: Modified-site
    ( B ) LOCATION: 10
    ( C ) OTHER INFORMATION: /label= Substituted-Ala
      / note= "Position 10 is
      beta-1- naphthyl-substituted."

( i x ) FEATURE:
    ( A ) NAME/KEY: Modified-site
    ( B ) LOCATION: 14
    ( C ) OTHER INFORMATION: /label= Substituted-Ala
      / note= "Position 14 is
      beta-1- naphthyl-substituted."

( x i ) SEQUENCE DESCRIPTION: SEQ ID NO:172:

Lys Ser Lys Val Gly Trp Leu Ile Gln Ala Phe His Lys Ala
1      5          10

( 2 ) INFORMATION FOR SEQ ID NO:173:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.228"

( i x ) FEATURE:
    ( A ) NAME/KEY: Modified-site
    ( B ) LOCATION: 9
    ( C ) OTHER INFORMATION: /label= Substituted-Phe
      / note= "Position 9 is
      para-amino- substituted."

( i x ) FEATURE:

(A) NAME/KEY: Modified-site
(B) LOCATION: 14
(C) OTHER INFORMATION: /label= Substituted-Ala
/ note= "Position 14 is
beta-1- naphthyl-substituted."

(xi) SEQUENCE DESCRIPTION: SEQ ID NO:173:

Lys Ser Lys Val Gly Trp Leu Ile Phe Leu Phe His Lys Ala
1               5                   10

(2) INFORMATION FOR SEQ ID NO:174:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.229"

(ix) FEATURE:
(A) NAME/KEY: Modified-site
(B) LOCATION: 5
(C) OTHER INFORMATION: /label= Substituted-Ala
/ note= "Position 5 is
para-amino- substituted."

(ix) FEATURE:
(A) NAME/KEY: Modified-site
(B) LOCATION: 14
(C) OTHER INFORMATION: /label= Substituted-Ala
/ note= "Position 14 is
beta-1- naphthyl-substituted."

(xi) SEQUENCE DESCRIPTION: SEQ ID NO:174:

Lys Ser Lys Val Phe Trp Leu Ile Gln Leu Phe His Lys Ala
1               5                   10

(2) INFORMATION FOR SEQ ID NO:175:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.230"

(ix) FEATURE:
(A) NAME/KEY: Modified-site
(B) LOCATION: 14
(C) OTHER INFORMATION: /label= Substituted-Ala
/ note= "Position 14 is
beta-1- naphthyl-substituted."

(xi) SEQUENCE DESCRIPTION: SEQ ID NO:175:

Lys Ser Lys Val Gly Trp Leu Ile Gln Leu Trp His Lys Ala
1               5                   10

(2) INFORMATION FOR SEQ ID NO:176:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
 (A) NAME/KEY: misc_feature
 (D) OTHER INFORMATION: "XMP.231"

(ix) FEATURE:
 (A) NAME/KEY: Modified-site
 (B) LOCATION: 10
 (C) OTHER INFORMATION: /label= Substituted-Ala
  / note= "Position 10 is
  beta-1- naphthyl-substituted."

(ix) FEATURE:
 (A) NAME/KEY: Modified-site
 (B) LOCATION: 12
 (C) OTHER INFORMATION: /label= Substituted-Ala
  / note= "Position 12 is
  beta-1- naphthyl-substituted."

(xi) SEQUENCE DESCRIPTION: SEQ ID NO:176:

Lys Ser Lys Val Gly Trp Leu Ile Gln Ala Phe Ala Lys Lys
1               5                   10

(2) INFORMATION FOR SEQ ID NO:177:

(i) SEQUENCE CHARACTERISTICS:
  (A) LENGTH: 14 amino acids
  (B) TYPE: amino acid
  (D) TOPOLOGY: linear (ii) MOLECULE TYPE: peptide (ix) FEATURE:
  (A) NAME/KEY: misc_feature
  (D) OTHER INFORMATION: "XMP.232"

(ix) FEATURE:
  (A) NAME/KEY: Modified-site
  (B) LOCATION: 9
  (C) OTHER INFORMATION: /label= Substituted-Phe
   / note= "Position 9 is
   para-amino- substituted."

(ix) FEATURE:
  (A) NAME/KEY: Modified-site
  (B) LOCATION: 12
  (C) OTHER INFORMATION: /label= Substituted-Ala
   / note= "Position 12 is
   beta-1- naphthyl-substituted."

(xi) SEQUENCE DESCRIPTION: SEQ ID NO:177:

Lys Ser Lys Val Gly Trp Leu Ile Phe Leu Phe Ala Lys Lys
1               5                   10

(2) INFORMATION FOR SEQ ID NO:178:

(i) SEQUENCE CHARACTERISTICS:
  (A) LENGTH: 14 amino acids
  (B) TYPE: amino acid
  (D) TOPOLOGY: linear (ii) MOLECULE TYPE: peptide (ix) FEATURE:
  (A) NAME/KEY: misc_feature
  (D) OTHER INFORMATION: "XMP.233"

(ix) FEATURE:
  (A) NAME/KEY: Modified-site
  (B) LOCATION: 5
  (C) OTHER INFORMATION: /label= Substituted-Phe
   / note= "Position 5 is
   para-amino- substituted."

(ix) FEATURE:
  (A) NAME/KEY: Modified-site
  (B) LOCATION: 12

( C ) OTHER INFORMATION: /label= Substituted-Ala
/ note= "Position 12 is
beta-1- naphthyl-substituted."

( x i ) SEQUENCE DESCRIPTION: SEQ ID NO:178:

Lys Ser Lys Val Phe Trp Leu Ile Gln Leu Phe Ala Lys Lys
1               5                   10

( 2 ) INFORMATION FOR SEQ ID NO:179:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.234"

( i x ) FEATURE:
( A ) NAME/KEY: Modified-site
( B ) LOCATION: 12
( C ) OTHER INFORMATION: /label= Substituted-Ala
/ note= "Position 12 is
beta-1- naphthyl-substituted."

( x i ) SEQUENCE DESCRIPTION: SEQ ID NO:179:

Lys Ser Lys Val Gly Trp Leu Ile Gln Leu Trp Ala Lys Lys
1               5                   10

( 2 ) INFORMATION FOR SEQ ID NO:180:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature
( D ) OTHER INFORMATION: "XMP.235"

( i x ) FEATURE:
( A ) NAME/KEY: Modified-site
( B ) LOCATION: 9
( C ) OTHER INFORMATION: /label= Substituted-Phe
/ note= "Position 9 is
para-amino- substituted."

( i x ) FEATURE:
( A ) NAME/KEY: Modified-site
( B ) LOCATION: 10
( C ) OTHER INFORMATION: /label= Substituted-Ala
/ note= "Position 10 is
beta-1- naphthyl-substituted."

( x i ) SEQUENCE DESCRIPTION: SEQ ID NO:180:

Lys Ser Lys Val Gly Trp Leu Ile Phe Ala Phe His Lys Lys
1               5                   10

( 2 ) INFORMATION FOR SEQ ID NO:181:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( i x ) FEATURE:
( A ) NAME/KEY: misc_feature (D) OTHER INFORMATION: "XMP.236"

(ix) FEATURE:
(A) NAME/KEY: Modified-site
(B) LOCATION: 5
(C) OTHER INFORMATION: /label= Substituted-Phe
/ note= "Position 5 is
para-amino- substituted."

(ix) FEATURE:
(A) NAME/KEY: Modified-site
(B) LOCATION: 10
(C) OTHER INFORMATION: /label= Substituted-Ala
/ note= "Position 10 is
beta-1- naphthyl-substituted."

(xi) SEQUENCE DESCRIPTION: SEQ ID NO:181:

Lys Ser Lys Val Phe Trp Leu Ile Gln Ala Phe His Lys Lys
1               5                   10

(2) INFORMATION FOR SEQ ID NO:182:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.237"

(ix) FEATURE:
(A) NAME/KEY: Modified-site
(B) LOCATION: 10
(C) OTHER INFORMATION: /label= Substituted-Ala
/ note= "Position 10 is
beta-1- naphthyl-substituted."

(xi) SEQUENCE DESCRIPTION: SEQ ID NO:182:

Lys Ser Lys Val Gly Trp Leu Ile Gln Ala Trp His Lys Lys
1               5                   10

(2) INFORMATION FOR SEQ ID NO:183:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.238"

(ix) FEATURE:
(A) NAME/KEY: Modified-site
(B) LOCATION: 5
(C) OTHER INFORMATION: /label= Substituted-Phe
/ note= "Position 5 is
para-amino- substituted."

(ix) FEATURE:
(A) NAME/KEY: Modified-site
(B) LOCATION: 9
(C) OTHER INFORMATION: /label= Substituted-Phe
/ note= "Position 9 is
para-amino- substituted."

(xi) SEQUENCE DESCRIPTION: SEQ ID NO:183:

Lys Ser Lys Val Phe Trp Leu Ile Phe Leu Phe His Lys Lys
1               5                   10

( 2 ) INFORMATION FOR SEQ ID NO:184:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.239"

( i x ) FEATURE:
        ( A ) NAME/KEY: Modified-site
        ( B ) LOCATION: 9
        ( C ) OTHER INFORMATION: /label= Substituted-Phe
            / note= "Position 9 is
            para-amino- substituted."

( x i ) SEQUENCE DESCRIPTION: SEQ ID NO:184:

Lys Ser Lys Val Gly Trp Leu Ile Phe Leu Trp His Lys Lys
1               5                   10

( 2 ) INFORMATION FOR SEQ ID NO:185:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.240"

( i x ) FEATURE:
        ( A ) NAME/KEY: Modified-site
        ( B ) LOCATION: 5
        ( C ) OTHER INFORMATION: /label= Substituted-Phe
            / note= "Position 5 is
            para-amino- substituted."

( x i ) SEQUENCE DESCRIPTION: SEQ ID NO:185:

Lys Ser Lys Val Phe Trp Leu Ile Gln Leu Trp His Lys Lys
1               5                   10

( 2 ) INFORMATION FOR SEQ ID NO:186:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.247"

( i x ) FEATURE:
        ( A ) NAME/KEY: Modified-site
        ( B ) LOCATION: 2
        ( C ) OTHER INFORMATION: /label= Substituted-Ala
            / note= "Position 2 is
            beta-1- naphthyl-substituted."

( i x ) FEATURE:
        ( A ) NAME/KEY: Modified-site
        ( B ) LOCATION: 6
        ( C ) OTHER INFORMATION: /label= Substituted-Ala
            / note= "Position 6 is
            beta-1- naphthyl-substituted."

( x i ) SEQUENCE DESCRIPTION: SEQ ID NO:186:

Lys Ala Lys Ala Gln Ala Arg Phe Leu Lys Lys Ser Lys Val Gly Trp
1               5                   10                  15

Leu Ile Leu Leu Phe His Lys Lys
                20

( 2 ) INFORMATION FOR SEQ ID NO:187:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.245"

( x i ) SEQUENCE DESCRIPTION: SEQ ID NO:187:

Lys Trp Lys Ala Gln Phe Arg Phe Leu Lys Lys Ser Lys Val Gly Trp
1               5                   10                  15

Leu Ile Gln Leu Trp His Lys Lys
                20

( 2 ) INFORMATION FOR SEQ ID NO:188:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.246"

( i x ) FEATURE:
        ( A ) NAME/KEY: Modified-site
        ( B ) LOCATION: 16
        ( C ) OTHER INFORMATION: /label= Substituted-Ala
        / note= "Position 16 is
        D-beta-2- naphthyl-substituted."

( x i ) SEQUENCE DESCRIPTION: SEQ ID NO:188:

Lys Trp Lys Ala Gln Phe Arg Phe Leu Lys Lys Ser Lys Val Gly Ala
1               5                   10                  15

Leu Ile Gln Leu Phe His Lys Lys
                20

( 2 ) INFORMATION FOR SEQ ID NO:189:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.248"

( i x ) FEATURE:
        ( A ) NAME/KEY: Modified-site
        ( B ) LOCATION: 2
        ( C ) OTHER INFORMATION: /label= Substituted-Ala
        / note= "Position 2 is
        beta-1- naphthyl-substituted."

( i x ) FEATURE:
          ( A ) NAME/KEY: Modified-site
          ( B ) LOCATION: 6
          ( C ) OTHER INFORMATION: /label= Substituted-Ala
                  / note= "Position 6 is
                  beta-1- naphthyl-substituted."

( i x ) FEATURE:
          ( A ) NAME/KEY: Modified-site
          ( B ) LOCATION: 16
          ( C ) OTHER INFORMATION: /label= Substituted-Ala
                  / note= "Position 16 is
                  D-beta-2- naphthyl-substituted."

( x i ) SEQUENCE DESCRIPTION: SEQ ID NO:189:

Lys Ala Lys Ala Gln Ala Arg Phe Leu Lys Lys Ser Lys Val Gly Ala
1               5                   10                  15

Leu Ile Gln Leu Phe His Lys Lys
            20

( 2 ) INFORMATION FOR SEQ ID NO:190:

( i ) SEQUENCE CHARACTERISTICS:
          ( A ) LENGTH: 14 amino acids
          ( B ) TYPE: amino acid
          ( D ) TOPOLOGY: linear ( i i ) MOLECULE TYPE: peptide ( i x ) FEATURE:
          ( A ) NAME/KEY: misc_feature
          ( D ) OTHER INFORMATION: "XMP.242"

( i x ) FEATURE:
          ( A ) NAME/KEY: Modified-site
          ( B ) LOCATION: 6
          ( C ) OTHER INFORMATION: /label= Substituted-Ala
                  / note= "Position 6 is
                  D-beta-2- naphthyl-substituted."

( x i ) SEQUENCE DESCRIPTION: SEQ ID NO:190:

Lys Ser Lys Val Gly Ala Leu Ile Leu Leu Phe His Lys Lys
1               5                   10

( 2 ) INFORMATION FOR SEQ ID NO:191:

( i ) SEQUENCE CHARACTERISTICS:
          ( A ) LENGTH: 28 amino acids
          ( B ) TYPE: amino acid
          ( D ) TOPOLOGY: linear ( i i ) MOLECULE TYPE: peptide ( i x ) FEATURE:
          ( A ) NAME/KEY: misc_feature
          ( D ) OTHER INFORMATION: "XMP.272"

( x i ) SEQUENCE DESCRIPTION: SEQ ID NO:191:

Lys Ser Lys Val Gly Trp Leu Ile Leu Leu Phe His Lys Lys Lys Ser
1               5                   10                  15

Lys Val Gly Trp Leu Ile Leu Leu Phe His Lys Lys
            20                  25

( 2 ) INFORMATION FOR SEQ ID NO:192:

( i ) SEQUENCE CHARACTERISTICS:
          ( A ) LENGTH: 28 amino acids
          ( B ) TYPE: amino acid
          ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.275"

( x i ) SEQUENCE DESCRIPTION: SEQ ID NO:192:

```
Lys  Ser  Lys  Val  Gly  Trp  Leu  Ile  Phe  Leu  Phe  His  Lys  Lys  Lys  Ser
1              5                        10                       15
Lys  Val  Gly  Trp  Leu  Ile  Phe  Leu  Phe  His  Lys  Lys
              20                        25
```

( 2 ) INFORMATION FOR SEQ ID NO:193:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.270"

( x i ) SEQUENCE DESCRIPTION: SEQ ID NO:193:

```
Lys  Ser  Lys  Val  Gly  Trp  Leu  Ile  Leu  Leu  Phe  His  Lys  Lys  Lys  Ser
1              5                        10                       15
Lys  Val  Gly  Trp  Leu  Ile  Gln  Leu  Phe  His  Lys  Lys
              20                        25
```

( 2 ) INFORMATION FOR SEQ ID NO:194:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.271"

( x i ) SEQUENCE DESCRIPTION: SEQ ID NO:194:

```
Lys  Ser  Lys  Val  Gly  Trp  Leu  Ile  Gln  Leu  Phe  His  Lys  Lys  Lys  Ser
1              5                        10                       15
Lys  Val  Gly  Trp  Leu  Ile  Leu  Leu  Phe  His  Lys  Lys
              20                        25
```

( 2 ) INFORMATION FOR SEQ ID NO:195:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.273"

( x i ) SEQUENCE DESCRIPTION: SEQ ID NO:195:

```
Lys  Ser  Lys  Val  Gly  Trp  Leu  Ile  Phe  Leu  Phe  His  Lys  Lys  Lys  Ser
1              5                        10                       15
Lys  Val  Gly  Trp  Leu  Ile  Gln  Leu  Phe  His  Lys  Lys
              20                        25
```

( 2 ) INFORMATION FOR SEQ ID NO:196:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.274"

( x i ) SEQUENCE DESCRIPTION: SEQ ID NO:196:

Lys Ser Lys Val Gly Trp Leu Ile Gln Leu Phe His Lys Lys Lys Ser
1               5                   10                  15

Lys Val Gly Trp Leu Ile Phe Leu Phe His Lys Lys
            20                  25

( 2 ) INFORMATION FOR SEQ ID NO:197:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.276"

( x i ) SEQUENCE DESCRIPTION: SEQ ID NO:197:

Lys Trp Lys Ala Gln Phe Arg Phe Leu Lys Lys Ser Lys Val Gly Trp
1               5                   10                  15

Leu Ile Phe Leu Phe His Lys Lys
            20

( 2 ) INFORMATION FOR SEQ ID NO:198:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.241"

( x i ) SEQUENCE DESCRIPTION: SEQ ID NO:198:

Lys Ser Lys Val Gly Trp Leu Ile Leu Leu Trp His Lys Lys
1               5                   10

( 2 ) INFORMATION FOR SEQ ID NO:199:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.243"

( i x ) FEATURE:
        ( A ) NAME/KEY: Modified-site
        ( B ) LOCATION: 6
        ( C ) OTHER INFORMATION: /label= Substituted-Ala
            / note= "Position 6 is D-beta-2- naphthyl-substituted."

( x i ) SEQUENCE DESCRIPTION: SEQ ID NO:199:

Lys  Ser  Lys  Val  Gly  Ala  Leu  Ile  Gln  Leu  Trp  His  Lys  Lys
1                        5                        10

( 2 ) INFORMATION FOR SEQ ID NO:200:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.244"

( i x ) FEATURE:
        ( A ) NAME/KEY: Modified-site
        ( B ) LOCATION: 6
        ( C ) OTHER INFORMATION: /label= Substituted-Ala
            / note= "Position 6 is
            D-beta-2- naphthyl-substituted."

( x i ) SEQUENCE DESCRIPTION: SEQ ID NO:200:

Lys  Ser  Lys  Val  Gly  Ala  Leu  Ile  Leu  Leu  Trp  His  Lys  Lys
1                        5                        10

( 2 ) INFORMATION FOR SEQ ID NO:201:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.249"

( x i ) SEQUENCE DESCRIPTION: SEQ ID NO:201:

Lys  Ser  Lys  Val  Gly  Gly  Leu  Ile  Gln  Leu  Phe  His  Lys  Lys
1                        5                        10

( 2 ) INFORMATION FOR SEQ ID NO:202:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.250"

( x i ) SEQUENCE DESCRIPTION: SEQ ID NO:202:

Lys  Ser  Lys  Val  Gly  Leu  Leu  Ile  Gln  Leu  Phe  His  Lys  Lys
1                        5                        10

( 2 ) INFORMATION FOR SEQ ID NO:203:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
  ( A ) NAME/KEY: misc_feature
  ( D ) OTHER INFORMATION: "XMP.251"

( x i ) SEQUENCE DESCRIPTION: SEQ ID NO:203:

Lys Ser Lys Val Gly Ile Leu Ile Gln Leu Phe His Lys Lys
1               5                   10

( 2 ) INFORMATION FOR SEQ ID NO:204:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.252"

( i x ) FEATURE:
    ( A ) NAME/KEY: Modified-site
    ( B ) LOCATION: 6
    ( D ) OTHER INFORMATION: /label= D- Ala
        / note= "The amino acid at position 6 is
        D-alanine"

( x i ) SEQUENCE DESCRIPTION: SEQ ID NO:204:

Lys Ser Lys Val Gly Ala Leu Ile Gln Leu Phe His Lys Lys
1               5                   10

( 2 ) INFORMATION FOR SEQ ID NO:205:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.253"

( i x ) FEATURE:
    ( A ) NAME/KEY: Modified-site
    ( B ) LOCATION: 6
    ( D ) OTHER INFORMATION: /label= D- Val
        / note= "The amino acid at position 6 is
        D-valine"

( x i ) SEQUENCE DESCRIPTION: SEQ ID NO:205:

Lys Ser Lys Val Gly Val Leu Ile Gln Leu Phe His Lys Lys
1               5                   10

( 2 ) INFORMATION FOR SEQ ID NO:206:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.254"

( i x ) FEATURE:
    ( A ) NAME/KEY: Modified-site
    ( B ) LOCATION: 6
    ( D ) OTHER INFORMATION: /label= beta-Ala / note= "The amino acid at position 6 is
  beta- alanine"

( x i ) SEQUENCE DESCRIPTION: SEQ ID NO:206:

Lys  Ser  Lys  Val  Gly  Ala  Leu  Ile  Gln  Leu  Phe  His  Lys  Lys
1                  5                            10

( 2 ) INFORMATION FOR SEQ ID NO:207:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.255"

( i x ) FEATURE:
    ( A ) NAME/KEY: Modified-site
    ( B ) LOCATION: 6
    ( D ) OTHER INFORMATION: /label= delta-aba
        / note= "The amino acid at position 6 is
          delta- aminobutyric acid"

( x i ) SEQUENCE DESCRIPTION: SEQ ID NO:207:

Lys  Ser  Lys  Val  Gly  Xaa  Leu  Ile  Gln  Leu  Phe  His  Lys  Lys
1                  5                            10

( 2 ) INFORMATION FOR SEQ ID NO:208:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.256"

( i x ) FEATURE:
    ( A ) NAME/KEY: Modified-site
    ( B ) LOCATION: 6
    ( D ) OTHER INFORMATION: /label= gaba
        / note= "The amino acid at position 6 is
          gamma- aminobutyric acid"

( x i ) SEQUENCE DESCRIPTION: SEQ ID NO:208:

Lys  Ser  Lys  Val  Gly  Xaa  Leu  Ile  Gln  Leu  Phe  His  Lys  Lys
1                  5                            10

( 2 ) INFORMATION FOR SEQ ID NO:209:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.257"

( i x ) FEATURE:
    ( A ) NAME/KEY: Modified-site
    ( B ) LOCATION: 6
    ( D ) OTHER INFORMATION: /label= d- methyl-A
        / note= "The amino acid at position 6 is
          delta-Methyl- alanine"

( x i ) SEQUENCE DESCRIPTION: SEQ ID NO:209:

Lys Ser Lys Val Gly Ala Leu Ile Gln Leu Phe His Lys Lys
1               5                   10

( 2 ) INFORMATION FOR SEQ ID NO:210:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.258"

( i x ) FEATURE:
        ( A ) NAME/KEY: Modified-site
        ( B ) LOCATION: 6
        ( D ) OTHER INFORMATION: /label= t- butyl-G
            / note= "The amino acid at position 6 is
            tert-butyl- glycine"

( x i ) SEQUENCE DESCRIPTION: SEQ ID NO:210:

Lys Ser Lys Val Gly Gly Leu Ile Gln Leu Phe His Lys Lys
1               5                   10

( 2 ) INFORMATION FOR SEQ ID NO:211:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.259"

( i x ) FEATURE:
        ( A ) NAME/KEY: Modified-site
        ( B ) LOCATION: 6
        ( D ) OTHER INFORMATION: /label= N- methyl-G
            / note= "The amino acid at position 6 is
            N-Methyl- glycine"

( x i ) SEQUENCE DESCRIPTION: SEQ ID NO:211:

Lys Ser Lys Val Gly Gly Leu Ile Gln Leu Phe His Lys Lys
1               5                   10

( 2 ) INFORMATION FOR SEQ ID NO:212:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.260"

( i x ) FEATURE:
        ( A ) NAME/KEY: Modified-site
        ( B ) LOCATION: 6
        ( D ) OTHER INFORMATION: /label= N- methyl-V
            / note= "The amino acid at position 6 is
            N-Methyl- valine"

( x i ) SEQUENCE DESCRIPTION: SEQ ID NO:212:

Lys Ser Lys Val Gly Val Leu Ile Gln Leu Phe His Lys Lys
1               5                   10

( 2 ) INFORMATION FOR SEQ ID NO:213:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.261"

( i x ) FEATURE:
    ( A ) NAME/KEY: Modified-site
    ( B ) LOCATION: 6
    ( D ) OTHER INFORMATION: /label= N- methyl-L
        / note= "The amino acid at position 6 is
        N-Methyl- leucine"

( x i ) SEQUENCE DESCRIPTION: SEQ ID NO:213:

Lys Ser Lys Val Gly Leu Leu Ile Gln Leu Phe His Lys Lys
1               5                   10

( 2 ) INFORMATION FOR SEQ ID NO:214:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.262"

( x i ) SEQUENCE DESCRIPTION: SEQ ID NO:214:

Lys Ser Lys Val Gly Trp Leu Ile Asn Leu Phe His Lys Lys
1               5                   10

( 2 ) INFORMATION FOR SEQ ID NO:215:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature
    ( D ) OTHER INFORMATION: "XMP.263"

( x i ) SEQUENCE DESCRIPTION: SEQ ID NO:215:

Lys Ser Lys Val Gly Trp Leu Ile Glu Leu Phe His Lys Lys
1               5                   10

( 2 ) INFORMATION FOR SEQ ID NO:216:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i x ) FEATURE:
    ( A ) NAME/KEY: misc_feature (D) OTHER INFORMATION: "XMP.264"

(xi) SEQUENCE DESCRIPTION: SEQ ID NO:216:

```
Lys  Ser  Lys  Val  Gly  Trp  Leu  Ile  Asp  Leu  Phe  His  Lys  Lys
1              5                        10
```

(2) INFORMATION FOR SEQ ID NO:217:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.265"

(xi) SEQUENCE DESCRIPTION: SEQ ID NO:217:

```
Lys  Ser  Lys  Val  Gly  Trp  Leu  Ile  Lys  Leu  Phe  His  Lys  Lys
1              5                        10
```

(2) INFORMATION FOR SEQ ID NO:218:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.266"

(xi) SEQUENCE DESCRIPTION: SEQ ID NO:218:

```
Lys  Ser  Lys  Val  Lys  Val  Leu  Ile  Gln  Leu  Phe  His  Lys  Lys
1              5                        10
```

(2) INFORMATION FOR SEQ ID NO:219:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.267"

(xi) SEQUENCE DESCRIPTION: SEQ ID NO:219:

```
Lys  Ser  Lys  Val  Lys  Trp  Ala  Ile  Gln  Leu  Phe  His  Lys  Lys
1              5                        10
```

(2) INFORMATION FOR SEQ ID NO:220:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.268"

(xi) SEQUENCE DESCRIPTION: SEQ ID NO:220:

```
Lys  Ser  Lys  Val  Gly  Val  Ala  Ile  Gln  Leu  Phe  His  Lys  Lys
1                   5                        10
```

( 2 ) INFORMATION FOR SEQ ID NO:221:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.269"

( x i ) SEQUENCE DESCRIPTION: SEQ ID NO:221:

```
Lys  Ser  Lys  Val  Lys  Val  Ala  Ile  Gln  Leu  Phe  His  Lys  Lys
1                   5                        10
```

( 2 ) INFORMATION FOR SEQ ID NO:222:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.277"

( i x ) FEATURE:
        ( A ) NAME/KEY: Modified-site
        ( B ) LOCATION: 2
        ( C ) OTHER INFORMATION: /label= Substituted-Ala
            / note= "The alanine at position 2 is
            beta-1- naphthyl-substituted."

( x i ) SEQUENCE DESCRIPTION: SEQ ID NO:222:

```
Lys  Ala  Lys  Ala  Gln  Phe  Arg  Phe  Leu  Lys  Lys  Ser  Lys  Val  Gly  Trp
1                   5                        10                       15

Leu  Ile  Leu  Leu  Phe  His  Lys  Lys
                    20
```

( 2 ) INFORMATION FOR SEQ ID NO:223:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
        ( A ) NAME/KEY: misc_feature
        ( D ) OTHER INFORMATION: "XMP.278"

( x i ) SEQUENCE DESCRIPTION: SEQ ID NO:223:

```
Ile  Lys  Ile  Ser  Gly  Lys  Trp  Lys  Ala  Ala  Trp  Arg  Phe  Leu  Lys
1                   5                        10                       15
```

( 2 ) INFORMATION FOR SEQ ID NO:224:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i x ) FEATURE:
- ( A ) NAME/KEY: misc_feature
- ( D ) OTHER INFORMATION: "XMP.279"

( i x ) FEATURE:
- ( A ) NAME/KEY: Modified-site
- ( B ) LOCATION: 10
- ( C ) OTHER INFORMATION: /label= Substituted-Ala
  / note= "The alanine at position 10 is
  beta-1- naphthyl-substituted."

( x i ) SEQUENCE DESCRIPTION: SEQ ID NO:224:

```
Ile Lys Ile Ser Gly Lys Trp Lys Ala Ala Phe Arg Phe Leu Lys
1               5                   10                  15
```

( 2 ) INFORMATION FOR SEQ ID NO:225:

( i ) SEQUENCE CHARACTERISTICS:
- ( A ) LENGTH: 15 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature
- ( D ) OTHER INFORMATION: "XMP.280"

( x i ) SEQUENCE DESCRIPTION: SEQ ID NO:225:

```
Ile Lys Ile Ser Gly Lys Trp Lys Ala Ala Phe Arg Phe Leu Lys
1               5                   10                  15
```

( 2 ) INFORMATION FOR SEQ ID NO:226:

( i ) SEQUENCE CHARACTERISTICS:
- ( A ) LENGTH: 15 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature
- ( D ) OTHER INFORMATION: "XMP.281"

( i x ) FEATURE:
- ( A ) NAME/KEY: Modified-site
- ( B ) LOCATION: 10
- ( C ) OTHER INFORMATION: /label= Substituted-Ala
  / note= "The alanine at position 10 is
  beta-1- naphthyl-substituted."

( x i ) SEQUENCE DESCRIPTION: SEQ ID NO:226:

```
Ile Lys Ile Ser Gly Lys Trp Lys Ala Ala Ala Arg Phe Leu Lys
1               5                   10                  15
```

( 2 ) INFORMATION FOR SEQ ID NO:227:

( i ) SEQUENCE CHARACTERISTICS:
- ( A ) LENGTH: 12 amino acids
- ( B ) TYPE: amino acid
- ( D ) TOPOLOGY: linear ( i i ) MOLECULE TYPE: peptide ( i x ) FEATURE:
- ( A ) NAME/KEY: misc_feature
- ( D ) OTHER INFORMATION: "XMP.170"

( x i ) SEQUENCE DESCRIPTION: SEQ ID NO:227:

```
Lys Trp Lys Ala Gln Lys Arg Phe Leu Lys Met Ser
1               5                   10
```

ANTI-FUNGAL METHODS AND MATERIALS

This is a continuation-in-part of U.S. patent application Ser. No. 08/273,540 filed Jul. 11, 1994, now abandoned, which is a continuation-in-part of U.S. patent application Ser. No. 08/209,762 filed Mar. 11, 1994, which is a continuation-in-part of U.S. patent application Ser. No. 08/183,222 filed Jan. 14, 1994, now abandoned, all of which are herein incorporated by reference.

BACKGROUND OF THE INVENTION

The present invention relates generally to methods of treating fungal infections by administration of bactericidal/permeability-increasing (BPI) protein products.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coil* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. amino acid sequence is set out in SEQ ID NO: 69 hereto.

BPI is a strongly cationic protein. The N-terminal haft of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et at., *J. Exp. Med.*, 174:649 (1991).] An N-terminal BPI fragment of approximately 23 kD, referred to as "rBPI$_{23}$," has been produced by recombinant means and also retains anti-bacterial activity against gram-negative organisms. Gazzano-Santoro et at., *Infect. Immun.* 60:4754–4761 (1992).

The bactericidal effect of BPI has been reported to be highly specific to gram-negative species, e.g., in Elsbach and Weiss, *Inflammation. Basic Principles and Clinical Correlates*, eds. Gallin et at., Chapter 30, Raven Press, Ltd. (1992). BPI is commonly thought to be non-toxic for other microorganisms, including yeast, and for higher eukaryotic cells. Elsbach and Weiss (1992), supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and higher eukaryotic cells tested at that time. It was also reported that BPI at a concentration of $10^6$ M or 160 μg/ml had no toxic effect, when tested at a pH of either 7.0 or 5.5, on the gram-positive organisms *Staphylococcus aureus* (four strains), *Staphylococcus epidermidis*, *Streptococcus faecalis*, *Bacillus subtilis*, *Micrococcus lysodeikticus*, and *Listeria monocytogenes*. BPI at $10^{-6}$ M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also Elsbach and Weiss, *Advances in Inflammation Research*, ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et at., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinnomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain beating, "rough" organisms [Weiss et at., *J. Clin. Invest.* 65:619–628 (1980)]. This first stage of BPI action, permeabilization of the gram-negative outer envelope, is reversible upon dissociation of the BPI, a process requiring the presence of divalent cations and synthesis of new LPS [Weiss et at., *J. Immunol.* 132:3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane (Mannion et at., *J. Clin. Invest.* 86:631–641 (1990)). Specific investigation of this possibility has shown that on a molar basis BPI is at least as inhibitory of cytoplasmic membrane vesicle function as polymyxin B (In't Veld et at., *Infection and Immunity* 56:1203–1208 (1988)) but the exact mechanism as well as the relevance of such vesicles to studies of intact organisms has not yet been elucidated.

Fungi are eukaryotic cells that may reproduce sexually or asexually and may be biphasic, with one form in nature and a different form in the infected host. Fungal diseases are referred to as mycoses. Some mycoses are endemic, i.e. infection is acquired in the geographic area that is the natural habitat of that fungus. These endemic mycoses are usually self-limited and minimally symptomatic. Some mycoses are chiefly opportunistic, occurring in immunocompromised patients such as organ transplant patients, cancer patients undergoing chemotherapy, burn patients, AIDS patients, or patients with diabetic ketoacidosis.

Fungal infections are becoming a major health concern for a number of reasons, including the limited number of anti-fungal agents available, the increasing incidence of species resistant to older anti-fungal agents, and the growing population of immunocompromised patients at risk for opportunistic fungal infections. The incidence of systemic fungal infections increased 600% in teaching hospitals and 220% in non-teaching hospitals during the 1980's. The most common clinical isolate is *Candida albicans* (comprising about 19% of all isolates). In one study, nearly 40% of all deaths from hospital-acquired infections were due to fungi. [Sternberg, *Science*, 266:1632–1634 (1994).]

Anti-fungal agents include three main groups. The major group includes polyene derivatives, including amphotericin B and the structurally related compounds nystatin and pimaricin. These are broad-spectrum anti-fungals that bind to ergosterol, a component of fungal cell membranes, and thereby disrupt the membranes. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated anti-fungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The second major group of anti-fungal agents includes azole derivatives which impair synthesis of ergosterol and lead to accumulation of metabolites that disrupt the function of fungal membrane-bound enzyme systems (e.g., cytochrome P450) and inhibit fungal growth. Significant inhibition of mammalian P450 results in significant drug interactions. This group of agents includes ketoconazole, clotrimazole, miconazole, econazole, butoconazole, oxiconazole, sulconazole, terconazole, fluconazole and itraconazole. These agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole that is used for oral and esophageal candidiasis and cryptococcal meningitis. Miconazole is a parenteral imidazole with efficacy in coccidioidomycosis and several other mycoses, but has side effects including hyperlipidemia and hyponatremia.

The third major group of anti-fungal agents includes allylaminesthiocarbamates, which are generally used to treat skin infections. This group includes tolnaftate and naftifine.

Another anti-fungal agent is griseofulvin, a fungistatic agent which is administered orally for fungal infections of skin, hair or nails that do not respond to topical treatment.

Most endemic mycoses are acquired by the respiratory route and are minimally symptomatic; cough, fever, headache, and pleuritic pain may be seen. Occasionally, endemic mycoses may cause progressive pulmonary disease or systemic infection. Histoplasmosis, caused by Histoplasma, is the most common endemic respiratory mycosis in the United States; over 40 million people have been infected. The disease is noncontagious and ordinarily self-limited, but chronic pulmonary infection and disseminated infection may occur. Pulmonary infection rarely requires treatment, but disseminated infection may be treated with amphotericin B. Coccidioidomycosis, caused by Coccidioides, is a noncontagious respiratory mycosis prevalent in the southwest. It also is usually serf-limited but may lead to chronic pulmonary infection or disseminated infection. Amphotericin B or miconazole may be given for treatment. Blastomycosis, caused by Blastomyces is a noncontagious, subacute or chronic endemic mycosis most commonly seen in the southeast. Most pulmonary infections are probably self-limited. Patients with progressive lung disease or disseminated disease, and immunocompromised patients, may be treated systemically with amphotericin B. Paracoccidioidomycosis, caused by Paracoccidioides, is a noncontagious respiratory mycosis that is the most common systemic mycosis in South America. It may be acute and self-limited or may produce progressive pulmonary disease or extrapulmonary dissemination. Disseminated disease is generally fatal in the absence of therapy. Sulfonamides may be used but have a low success rate. Amphotericin B produces a higher response rate but relapses may still occur.

Cryptococcosis is a noncontagious, often opportunistic mycosis. It is characterized by respiratory involvement or hematogenous dissemination, often with meningitis. A major etiologic agent is *C. neoformans*. Most pulmonary infections are probably overlooked, but cryptococcal meningitis, which accounts for 90% of reported disease, is dramatic and seldom overlooked. Cryptococcosis is a particular problem in immunocompromised patients; cryptococcal meningitis occurs in 7 to 10% of AIDS patients. The principal symptom of meningitis is headache; associated findings include mental changes, ocular symptoms, hearing deficits, nausea, vomiting, and seizures. Without treatment, 80% of patients die within two years. In meningitis, cryptococci can be observed in India ink preparations of cerebrospinal fluid sediment, and can be cultured from the cerebrospinal fluid. Treatment is generally with fluconazole or the combination of amphoteficin B and flucytosine, although amphoteficin B does not cross the blood brain barrier.

Aspergillosis is a term that encompasses a variety of disease processes caused by Aspergillus species. Aspergillus species are ubiquitous; their spores are constantly being inhaled. Of the more than 300 species known, only a few are ordinarily pathogenic for man: *A. fumigatus, A. flavus, A. niger, A. nidulans, A. terreus, A. sydowi, A. flavatus,* and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of eases, there is hematogenous spread to other sites. Aspergillosis is also a rare but devastating complication of bum wounds; amputation is often required for cure. Invasive aspergillosis is commonly fatal, so aggressive diagnosis and treatment is required. Blood, urine and cerebrospinal fluid cultures are rarely positive, but fungi can be seen in smears and biopsies. Amphoteficin B can be given for treatment.

Mucormycosis is an acute suppurative opportunistic mycosis that produces rhinocerebral, pulmonary or disseminated disease in immunocompromised patients, and local or disseminated disease in patients with bums or open wounds. Infection is caused by fungi in the class Zygomycetes, and include Basidiobolus, Conidiobolus, Rhizopus, Mucor, Absidia, Mortierella, Cunninghamella, and Saksenaea. Rhinocerebral mucormycosis accounts for about half of all cases of mucormycosis. It is one of the most rapidly fatal funga diseases, with death occurring within 2–10 days in untreated patients. Early clinical signs include nasal stuffiness, bloody nasal discharge, facial swelling and facial pain. The infection then spreads to the eyes, cranial nerves and brain. Pulmonary mucormycosis is nearly as common as rhinocerebral disease and manifests with the same necrotizing and infarction as aspergillosis. Fungi are virtually never seen or cultured from blood, sputum or cerebrospinal fluid. Disseminated mucormycosis may follow pulmonary or bum wound infection. Treatment is with amphotericin B.

Candidiasis is a general term for a variety of local and systemic processes caused by colonization or infection of the host by species of the yeast Candida. Candidiasis occurs worldwide; superficial infections of the skin, mouth and other mucus membranes are universal. Invasive systemic disease has become a problem due to the use of high doses of antibiotics that destroy normal bacterial flora, immunosuppressive agents, and agents toxic to bone marrow, e.g., during cancer therapy. Neutropenia is a major risk factor for Candida dissemination. Candidiasis is also seen among immunocompromised individuals such as AIDS patients, organ transplant patients, patients receiving parentera nutrition, and cancer patients undergoing radiation treatment and chemotherapy. It is the most common opportunistic mycosis in the world. The most common etiologic agent is *Candida albicans*. Other infectious species include *C. tropicalis, C. parapsilosis, C. stellatoidea, C. krusei, C. parakrusei, C. lusitanae, C. pseudotropicalis, C. guilliermondi* and *C. glabrata*. *Candida albicans* is normally found in the mouth, throat, gastrointestinal tract and vagina of humans. Non-albicans species frequently colonize skin. Candida species occur in two forms that are not temperature- or host-dependent. The usual colonizing form are yeasts that may assume a pseudomycelial configuration, especially during tissue invasion. Pseudomyceliae result from the sequential budding of yeasts into branching chains of elongated organisms.

*Candida albicans* contains cell wall mannoproteins that appear to be responsible for attachment of the yeast cells to specific host tissues. It has been reported that the mannan portion, rather than the protein portion, of the mannoproteins is responsible for adherence of fungal cells to spleen and lymph node tissues in mice. [Kanbe et al., *Infection Immunity*, 61:2578–2584 (1993).]

*C. albicans* also binds avidly to extracellular matrix (ECM) proteins such as fibronectin, laminin, and types I and IV collagen, all of which contain heparin-binding domains. This suggests *C. albicans* may express a heparin-like surface molecule. Adherence of *C. albicans* to the ECM may be important in the pathogenesis of disseminated candidiasis. It has been demonstrated that hepafin, heparan sulfate and dextran sulfate glycosaminoglycans (GAGs) inhibit adherence of *C. albicans* to ECM and ECM proteins, possibly by a mechanism involving binding of GAGs to ECM proteins, thus masking these selective ligands. [Klotz et at., *FEMS Microbiology Letters*, 78:205–208 (1992).]

Clinically, candidiasis manifests as superficial mucocutaneous infections, chronic mucocutaneous candidiasis, or systemic infection. Superficial mucocutaneous infections can occur in any area of skin or mucus membrane. Thrush, commonly seen in AIDS patients, is characterized by a patchy or continuous, creamy to gray pseudomembrane that covers the tongue, mouth, or other oropharyngeal surfaces and may be accompanied by ulceration and necrosis. Laryngeal involvement results in hoarseness. Esophagitis is often an extension of oropharyngeal disease and may manifest with symptoms of retrosternal pain and dysphagia. Intestinal candidiasis is commonly asymptomatic, but is a major source of hematogenous invasion in immunocompromised individuals. Intertrigo involves the axillae, groins, inframammary folds, and other warm, moist areas, and may manifest as red, oozing or dry, scaly lesions. Infections may occur in other areas, including perianal and genital areas. Paronychia, infection of the nails, often follows chronic exposure of the hands or feet to moisture. Some patients with limited T-cell immunodeficiency develop chronic mucocutaneous candidiasis. These patients suffer from persistent superficial Candida infection of the skin, scalp, nails and mucus membranes.

Most cases of systemic candidiasis are caused by *Candida albicans* and *C. tropicalis*, and increasingly, *C. glabrata*. Clinical manifestations of Candida infection appear mainly in the eyes, kidneys and skin. In the eyes, there may be single or multiple raised, white, fluffy chorioretinal lesions. These lesions are a potential cause of blindness. Involvement of the kidneys includes diffuse abscesses, capillary necrosis and obstruction of the ureters. Infection may result in progressive renal insufficiency. Systemic Candida infection can also manifest as maculonodular skin lesions surrounded by a reddened area; these lesions have an appearance similar to acne but are a major clue to a potentially lethal disease. Other manifestations of systemic candidiasis may include osteomyelitis, arthritis, meningitis, and abscesses in the brain, heart, liver, spleen and thyroid. Involvement of the lungs is also common, but pulmonary lesions are usually too small to be seen on chest X-ray. Finally, Candida endocarditis can occur in patients receiving prolonged intravenous therapy or cardiac valve implants, or in intravenous drug abusers. Fungal lesions appear on the valves, and can embolize and occlude large blood vessels.

Superficial infections are diagnosed by microscopic examination of scrapings or swabs of infected lesions in the presence of 10% potassium hydroxide. Candida organisms can also be seen on gram stain. Endocarditis is diagnosed by blood cultures or demonstration of bulky valvular lesions on echocardiography. Systemic candidiasis may be difficult to diagnose because the presence of heavy colonization at the usual sites of infection indicates, but does not prove, that dissemination has occurred. The most reliable evidence of systemic candidiasis is biopsy demonstration of tissue invasion or recovery of yeast from fluid in a closed body cavity, such as cerebral spinal fluid, pleural or peritoneal fluid. Similarly, positive blood or urine or sputum cultures may indicate invasive disease or simply localized disease around indwelling devices, e.g., catheters or intravenous lines.

Mucocutaneous infections may be treated with topical preparations of nystatin, amphotericin B, clotrimazole, miconazole, haloprogin or gentian violet. Oropharyngeal or esophageal candidiasis can be treated with systemic agents such as ketoconazole or fluconazole. Chronic mucocutaneous candidiasis syndrome may respond to topical or systemic therapeutic agents such as amphotericin B or ketoconazole, but often relapses when medication is discontinued. Cystitis may be treated with amphotericin B bladder rinses, or a brief low-dose intravenous course of amphotericin B with or without oral flucytosine. Endocarditis is essentially incurable without valve replacement, accompanied by a 6 to 10 week course of amphotericin B and flucytosine. Even with therapy, however, complete cure of endocarditis is not always possible.

The mortality rate from systemic candidiasis is about 50%. Systemic candidiasis may be treated with fluconazole, a fungistatic agent, or amphotericin B, a fungicidal agent although systemic use of the latter is limited by its toxicity. Both drugs have substantial adverse reactions when used in combination with cyclosporine A, which itself can be nephrotoxic. The removal of precipitating factors such as intravenous lines or catheters is also important for controlling infection. Flucytosine therapy can be added to the amphotericin B therapy for treatment of systemic candidiasis, especially in patients that are not immunocompromised. In immunocompromised patients, however, these infections are problematic and resist effective treatment. Mortality with systemic candidiasis can be over 90% in such patients. Furthermore, chronic mucocutaneous candidiasis and candidal endocarditis often show evidence of disease after having been declared cured.

There continues to exist a need in the art for new anti-fungal methods and materials. In particular, effective anti-fungal therapy for systemic mycoses is limited. Products and methods responsive to this need would ideally involve substantially non-toxic compounds available in large quantities by means of synthetic or recombinant methods. Ideal compounds would have a rapid effect and a broad spectrum of fungicidal or fungistatic activity against a variety of different fungal species when administered or applied as the sole anti-fungal agent. Ideal compounds would also be useful in combinative therapies with other anti-fungal agents, particularly where these activities would reduce the amount of anti-fungal agent required for therapeutic effectiveness, enhance the effect of such agents, or limit potential toxic responses and high cost of treatment.

SUMMARY OF THE INVENTION

The present invention provides methods of treating a subject suffering from a fungal infection by administering a therapeutically effective amount of a BPI protein product. This is based on the surprising discovery that BPI protein products have fungicidal/fungistatic effects. BPI protein products may be administered alone or in conjunction with known anti-fungal agents. When made the subject of adjunctive therapy, the administration of BPI protein products may reduce the amount of anti-fungal agent needed for effective therapy, thus limiting potential toxic response and/or high cost of treatment. Administration of BPI protein products may also enhance the effect of such agents, accelerate the effect of such agents, or reverse resistance of fungi to such agents.

In addition, the invention provides a method of killing or inhibiting growth of fungi comprising contacting the fungi with a BPI protein product. This method can be practiced in vivo or in a variety of in vitro uses such as use to decontaminate fluids and surfaces and to sterilize surgical and other medical equipment and implantable devices, including prosthetic joints and indwelling invasive devices.

A further aspect of the invention involves use of a BPI protein product for the manufacture of a medicament for treatment of fungal infection. The medicament may include, in addition to a BPI protein product, other chemotherapeutic agents such as anti-fungal agents.

Numerous additional aspects and advantages of the invention will become apparent to those skilled in the art upon considering the following detailed description of the invention, which describes the presently preferred embodiments thereof.

DETAILED DESCRIPTION OF THE INVENTION

Figure 1:
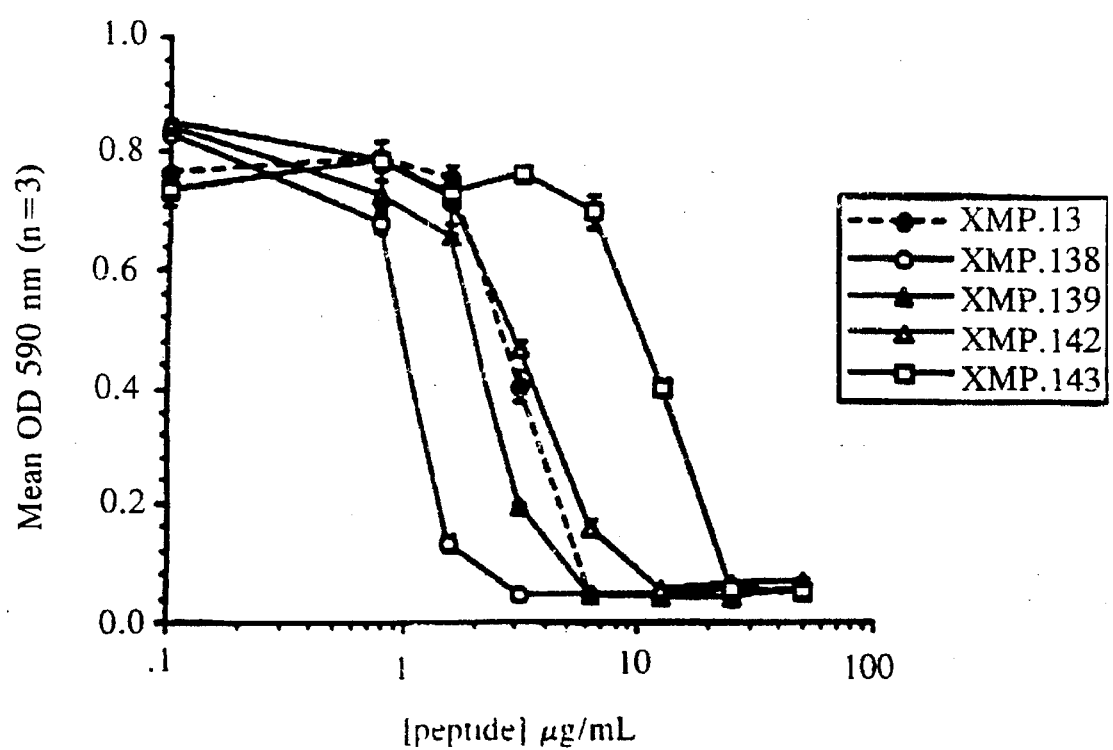
FIG. 1 provides results of broth assay tests of the activity of various BPI protein products against C. albicans.

The present invention relates to the surprising discovery that a BPI protein product can be administered to treat subjects suffering from fungal infection, and provides methods of treating such infections. Unexpectedly, BPI protein products were demonstrated to have anti-fungal activities both in in vitro killing assays and in in vivo models of fungal infection, as measured, for example, by improved survival or reduction of colony-forming units in circulation after fungal challenge. A variety of fungal infections, including infections caused by Aspergillosis, infections caused by Cryptococcus, such as cryptococcal meningitis, and mucocutaneous and systemic candidiasis caused by Candida species, may be treated according to the invention.

The BPI protein product may be administered systemically or topically. Systemic routes of administration include oral, intravenous, intramuscular or subcutaneous injection (including into depots for long-term release), intraocular or retrobulbar, intrathecal, intraperitoneal (e.g. by intraperitoneal lavage), transpulmonary using aerosolized or nebulized drug, or transdermal. Topical routes include administration in the form of salves, ophthalmic drops, ear drops, or irrigation fluids (for, e.g., irrigation of wounds). "Effective dosage ranges from about 100 µg/kg to about 100 mg/kg of body weight are contemplated."

The BPI protein product may be administered in conjunction with other anti-fungal agents presently known to be effective. Preferred anti-fungal agents for this purpose are amphotericin B and fluconazole. Concurrent administration of BPI protein product with anti-fungal agents is expected to improve the therapeutic effectiveness of the anti-fungal agents. This may occur through reducing the concentration of anti-fungal agent required to eradicate or inhibit fungal growth, e.g., replication. Because the use of some agents is limited by their systemic toxicity or prohibitive cost, lowering the concentration of anti-fungal agent required for therapeutic effectiveness reduces toxicity and/or cost of treatment, and thus allows wider use of the agent. Concurrent administration of BPI protein product and another anti-fungal agent may produce a more rapid or complete fungicidal/fungistatic effect than could be achieved with either agent alone. BPI protein product administration may reverse the resistance of fungi to anti-fungal agents. BPI protein product administration may also convert a fungistatic agent into a fungicidal agent.

An advantage provided by the present invention is the ability to treat fungal infections, particularly Candida infections, that are presently considered incurable. Another advantage is the ability to treat fungi that have acquired resistance to known anti-fungal agents. A further advantage of concurrent administration of BPI with an anti-fungal agent having undesirable side effects, e.g., amphotericin B, is the ability to reduce the amount of anti-fungal agent needed for effective therapy. The present invention may also provide quality of life benefits due to, e.g., decreased duration of therapy, reduced stay in intensive care units or reduced stay overall in the hospital, with the concomitant reduced risk of serious nosocomial (hospital-acquired) infections.

"Concurrent administration" as used herein includes administration of the agents together, or before or after each other. The BPI protein products and anti-fungal agents may be administered by different routes. For example, the BPI protein product may be administered intravenously while the anti-fungal agents are administered intramuscularly, intravenously, subcutaneously, orally or intraperitoneally. Alternatively, the BPI protein product may be administered intraperitoneally while the anti-fungal agents are administered intraperitoneally or intravenously, or the BPI protein product may be administered in an aerosolized or nebulized form while the anti-fungal agents are administered, e.g., intravenously. The BPI protein product and anti-fungal agents may be both administered intravenously. The BPI protein product and anti-fungal agents may be given sequentially in the same intravenous line, after an intermediate flush, or may be given in different intravenous lines. The BPI protein product and anti-fungal agents may be administered simultaneously or sequentially, as long as they are given in a manner sufficient to allow both agents to achieve effective concentrations at the site of infection.

Concurrent administration of BPI protein product and antibiotic is expected to provide more effective treatment of fungal infections. Concurrent administration of the two agents may provide greater therapeutic effects in vivo than either agent provides when administered singly. For example, concurrent administration may permit a reduction in the dosage of one or both agents with achievement of a similar therapeutic effect. Alternatively, the concurrent administration may produce a more rapid or complete fungicidal/fungistatic effect than could be achieved with either agent alone.

Therapeutic effectiveness is based on a successful clinical outcome, and does not require that the anti-fungal agent or agents kill 100% of the organisms involved in the infection. Success depends on achieving a level of anti-fungal activity at the site of infection that is sufficient to inhibit the fungi in a manner that tips the balance in favor of the host. When host defenses are maximally effective, the anti-fungal effect required may be minimal. Reducing organism load by even one log (a factor of 10) may permit the host's own defenses to control the infection. In addition, augmenting an early fungicidal/fungistatic effect can be more important than long-term fungicidal/fungistatic effect. These early events are a significant and critical part of therapeutic success, because they allow time for host defense mechanisms to activate.

BPI protein product is thought to interact with a variety of host defense elements present in whole blood or serum, including complement, p15 and LBP, and other cells and components of the immune system. Such interactions may result in potentiation of the activities of BPI protein product. Because of these interactions, BPI protein products can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media contain higher than physiological concentrations of magnesium and calcium, which are typically inhibitors of the activity of BPI protein products. Furthermore, in the host, BPI protein product is available to neutralize translocation of gram-negative bacteria and concomitant release of endotoxin, a further clinical benefit not seen in or predicted by in vitro tests of anti-fungal activity.

It is also contemplated that the BPI protein product be administered with other products that potentiate the activity of BPI protein products, including the anti-fungal activity of BPI protein products. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.*, 265: 15956 (1990) and Levy et al. *J. Biol. Chem.*, 268:6038–6083 (1993) which address naturally-occurring 15 kD proteins potentiating BPI antibacterial activity. See also co-owned, co-pending PCT Application No. US94/07834 filed Jul. 13, 1994, which corresponds to U.S. patent application Ser. No. 08/274,303 filed Jul. 11, 1994 as a continuation-in-part of U.S. patent application Ser. No. 08/093,201 filed Jul. 14, 1993. These applications, which are all incorporated herein by reference, describe methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 filed Jun. 17, 1994, which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are hereby incorporated by reference. It has also been observed that poloxamer surfactants enhance the anti-bacterial activity of BPI protein products, as described in Lambert, U.S. Application No. 08/372,104 filed Jan. 13, 1995, poloxamer surfactants may also enhance the activity of anti-fungal agents.

Without being bound by a theory of the invention, it is believed that BPI protein products may have several modes of action. BPI protein product, through its heparin-binding ability, may interfere with the binding of fungi to the extracellular matrix. For example, heparin-like surface molecules of Candida are believed to mediate adhesion of the yeast to extracellular matrix and host tissues. BPI protein product may also act directly on the cytoplasmic membrane of fungi. In addition, BPI may bind to fungal cell wall mannoproteins that are structurally similar to the LPS of gram-negative organisms or that are responsible for adherence to target host tissues, thus interfering with fungal interaction with host tissues. Binding to fungal mannans may also promote access of BPI protein product to the inner cytoplasmic membrane. Finally, because fungal infection may cause stress-induced translocation of bowel flora and/or LPS, BPI may also act beneficially by killing gram-negative bacteria and neutralizing LPS.

In addition, the invention provides a method of killing or inhibiting growth of fungi comprising contacting the fungi with a BPI protein product. This method can be practiced in vivo or in a variety of in vitro uses such as use in food preparations or to decontaminate fluids and surfaces or to sterilize surgical and other medical equipment and implantable devices, including prosthetic joints. These methods can also be used for in situ sterilization of indwelling invasive devices such as intravenous lines and catheters, which are often foci of infection.

A further aspect of the invention involves use of a BPI protein product for the manufacture of a medicament for treatment of fungal infection. The medicament may include, in addition to a BPI protein product, other chemotherapeutic agents such as anti-fungal agents. The medicament can optionally comprise a pharmaceutically acceptable diluent, adjuvant or carrier.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding, and methods for expression of, BPI proteins including recombinant BPI holoprotein, referred to as $rBPI_{50}$ and recombinant fragments of BPI. Co-owned, copending U.S. patent application Ser. No. 07/885,501 and a continuation-in-part thereof, U.S. patent application Ser. No. 08/072,063 filed May 19, 1993 and corresponding PCT Application No. 93/04752 filed May 19, 1993, which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include a N-terminal fragment of natural human BPI of approximately 25 kD, described in Ooi et at., *J. Exp. Med.*, 174:649 (1991), and the recombinant expression product of DNA encoding N-terminal amino acids from 1 to about 193 to 199 of natural human BPI, described in Gazzano-Santoro et at., *Infect. Immun.* 60:4754–4761 (1992), and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of Gray et at., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 145 and 146) set out in FIG. 1 of Gray et at., supra, with the exceptions noted for $rBPI_{23}$ and with the exception that residue 417 is alanine (specified by GCT) rather than valine (specified by GTT). Other examples include dimeric forms of BPI fragments, as described in co-owned and co-pending U.S. patent application Ser. No. 08/212,132, filed Mar. 11, 1994, now U.S. Pat. No. 5,447,913 the disclosures of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, and dimetic forms of BPI variants. Examples of such hybrid fusion proteins and dimeric forms are described by Theofan et al. in co-owned, copending U.S. patent application Ser. No. 07/885,911, and a continuation-in-part application thereof, U.S. patent application Ser. No. 08/064, 693 filed May 19, 1993 and corresponding PCT Application No. US93/04754 filed May 19, 1993, which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, co-owned, copending U.S. patent application Ser. No. 08/013,801 filed Feb. 2, 1993 and corresponding PCT Application No. US94/01235 filed Feb. 2, 1994, the disclosures of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated $rBPI_{21}\Delta cys$ or $rBPI_{21}$. Other examples include dimetic forms of BPI analogs; e.g. co-owned and co-pending U.S. patent application Ser. No. 08/212,132 filed Mar. 11, 1994, now U.S. Pat. No. 5,447,913, the disclosures of which are incorporated herein by reference.

Other BPI protein products useful according to the methods of the invention are peptides derived from or based on BPI produced by recombinant or synthetic means (BPI-derived peptides), such as those described in co-owned and copending PCT Application No. US94/10427 filed Sep. 15, 1994, which corresponds to U.S. patent application Ser. No. 08/306,473, filed Sep. 15, 1994, and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 fried Mar. 11, 1994), which is a continuation-in-part of U.S. patent application Ser. No. 08/030,644 filed Mar. 12, 1993, the disclosures of all of which are incorporated herein by reference.

Presently preferred BPI protein products include recombinantly-produced N-terminal fragments of BPI, especially those having a molecular weight of approximately between 21 to 25 kD such as $rBPI_{23}$ or $rBPI_{21}$, or dimeric forms of these N-terminal fragments (e.g., $rBPI_{42}$ dimer). Additionally, preferred BPI protein products include $rBPI_{50}$ and BPI-derived peptides. Presently preferred BPI-derived peptides include those having an amino acid sequence of BPI protein from about position 142 to about position 169, subsequences thereof and variants of the sequence or subsequence thereof, which possess a BPI anti-fungal biological activity.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants, other chemotherapeutic agents or additional known anti-fungal agents. A stable pharmaceutical composition containing BPI protein products (e.g., $rBPI_{50}$, $rBPI_{23}$) comprises the BPI protein product at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Dela.). Another stable pharmaceutical composition containing BPI protein products (e.g., $rBPI_{21}$) comprises the BPI protein product at a concentration of 2 mg/ml in 5 mM citrate, 150 mM NaCl, 0.2% poloxamer 188 and 0.002% polysorbate 80. Such preferred combinations are described in co-owned, co-pending PCT Application No. US94/01239 filed Feb. 2, 1994, which corresponds to U.S. patent application Ser. No. 08/190,869 filed Feb. 2, 1994 and U.S. patent application Ser. No. 08/012,360 filed Feb. 2, 1993, the disclosures of all of which are incorporated herein by reference.

Other aspects and advantages of the present invention will be understood upon consideration of the following illustrative examples wherein Example 1 addresses preparation and in vitro anti-fungal testing of BPI protein products; Example 2 addresses the in vivo effect of BPI protein products on survival rate of mice challenged with Candida; Example 3 addresses additional in vitro and in vivo testing of the anti-fungal effect of BPI protein products on a variety of fungal species; Example 4 addresses the in vivo anti-fungal effect of BPI protein products in rats; and Example 5 addresses further in vivo testing of anti-fungal effects.

EXAMPLE 1

IN VITRO ANTI-FUNGAL EFFECTS

This example addresses in vitro screening of BPI protein products, and specifically BPI-derived peptides, for anti-fungal activity in a broth assay and/or in a radial diffusion assay.

The BPI-derived peptides tested were all prepared according to the procedures described in parent U.S. patent application Ser. Nos. 08/209,762 and 08/183,222. Briefly summarized, peptides were prepared by solid phase peptide synthesis according to the methods of Merrifield, *J. Am Chem. Soc.* 85: 2149 (1963) and Merrifield et al. *Anal. Chem.*, 38:1905–1914 (1966) using an Applied Biosystems, Inc. Model 432 peptide synthesizer. Alternatively, peptides may be synthesized by the procedure described in Example 2, infra. Peptide design was based in part on the discovery of three functional domains present in the $NH_2$-terminal region of the BPI holoprotein: domain I comprising BPI amino acids from about position 17 to about position 45 (SEQ ID NO: 1); domain II comprising BPI amino acids from about position 65 to about 99 (SEQ ID NO: 6); and domain III comprising BPI amino acids from about position 142 to about position 169 (SEQ ID NO: 12). Peptides include sequences and subsequences of the domain sequences and variants thereof, including linear and branched chain combination peptides with and without single or multiple amino acid (including atypical amino acid) substitutions as well as cyclized peptides and interdomain sequence peptides. Table 1 below sets out peptides derived from or based on BPI sequences, which are identified by peptide number with a prefix XMP or BPI (e.g., XMP.1 or BPI.1, XMP.2 or BPI.2, etc.), SEQ ID NO:, amino acid sequence based on reference to position within BPI and designation of amino acid substitutions and additions. Also set out in Table 1 are mass spectroscopy and HPLC estimates of purity of the peptides.

In each broth assay screening procedure, a colony of *C. albicans* designated CA-1, Strain SLU #1 that was received from the laboratories of G. Matuschak and A. Lechner, St. Louis University Hospital, St. Louis, Mo., where the strain was maintained, was inoculated into a tube containing 5 ml Sabouraud Dextrose broth (2% dextrose, 1% neopeptone) and incubated overnight at 37° C. with shaking. The overnight culture was diluted 1:50 into 5 ml of fresh broth and incubated for 3 hours at 37° C. Organisms were pelleted by centrifugation in a Beckman J-6M centrifuge for 5 minutes at 3000 rpm (1500×g) and the pellets were resuspended in 5 ml phosphate buffered saline (PBS) and the optical density at 570 nm was determined. On the basis of the determination that one OD unit equals $3 \times 10^7$ colony forming units/ml, yeast cells were diluted to $2 \times 10^6$ cells/ml in Sabouraud Dextrose broth.

Peptides derived from or based on BPI to be screened were originally constituted in Dulbocco's-PBS, were diluted to 100 µg/ml in broth and were serially diluted 2-fold into wells of a 96 well sterile, flat bottom, non-pyrogenic tissue culture plate (Costar, Cambridge, Mass.). All assays were performed in triplicate. $2 \times 10^5$ organisms were added at 100 µl per well; the plate was incubated on a shaker at 37° C. for 18 hours; and the optical densities for each well were read at 590 nm. FIG. 1 hereto graphically illustrates the dose response curves for five peptides XMP.13, XMP.138, XMP.139, XMP.142 and XMP.143). All illustrated peptides reduced optical density of the cultures to below 0.1 at doses of less than about 50 µg/ml, with XMP.138 displaying the best results of the illustrated peptides at low dosages. Table 1 sets out broth assay data in terms of minimum inhibitory concentration (MIC), i.e. the lowest concentration required to reduce the optical density at 590 nm to below 0.1.

In the radial diffusion assay procedures, yeast CA-1 cultures and peptide solutions were prepared as in the broth assay procedure described above. Ten mL of molten underlayer agarose comprising 3% Sabouraud Dextrose broth, 1% agarose (Pharmacia, Piscataway, N.J.), 0.02% Tween 20, and 10 mM sodium phosphate, at pH 7.4 was added to polystyrene robes and maintained in a 56° C. water bath until the addition of yeast. Tubes were cooled to approximately 45° C., yeast were added to give a final concentration of 1×10$^6$ CFU/ml, and the tubes were mixed again by inverting. The contents were poured into level square petri dishes and distributed evenly. The agarose solidified in less than 30 seconds and had a uniform thickness of about 1 min. A series of wells were punched into the hardened agarose using a sterile 3 mm punch attached to a vacuum apparatus.

Peptides to be assayed were 2-fold serially diluted in Dulbecco's PBS (D-PBS) starting from a concentration of approximately 1 mg/mL. Five µL of each dilution was added to each well and the plates were incubated at 37° C. for 3 hours. An overlayer of 10 mL of molten agarose comprising 6% Sabouraud Dextrose broth, 1% agarose, and 10 mM sodium phosphate, pH 7.4, (at approximately 45° C.) was then added and plates were incubated overnight at 37° C. Following this overnight incubation, a dilute Coomassie solution was poured into the plates and allowed to stain for 24 hours.

Clear zones of growth inhibition around each well were measured with calipers. The actual area of growth inhibition (mm$^2$) was calculated by subtracting the area of the well. Table 1 below sets out the results of the radial diffusion assays for tested peptides in terms of the number of picomoles (pmol) of peptide required to establish a 30 mm$^2$ area of growth inhibition.

Peptides XMP.221 through XMP.281 (SEQ ID) NOS: 166 through 226) are prepared and tested for anti-fungal activity as described above.

Further experiments are performed to determine the anti-fungal activity of BPI protein products on strains of Candida considered resistant to other anti-fungal agents: polyene-resistant *C. albicans* (ATCC Accession No. 38247), 5-fluorocytosine-resistant *C albicans* (ATCC No. 44373), azole-resistant *C. albicans* (ATCC No. 62342), and ketoconazole-resistant *C. albicans* (ATCC No. 64124).

TABLE 1

| Peptide # (Seq. ID No.) | Protein AA Segment | MS % Purity | HPLC % Purity | C. albicans MIC (µg/ml) | C. albicans pmol/ 30 mm$^2$ zone |
|---|---|---|---|---|---|
| XMP.1 (4) | 19–33 | — | 2 Peaks | x | x |
| XMP.2 (7) | 85–99 | 64 | 37.2 | >50 | x |
| XMP.3 (11) | 73–99 | — | 17 | x | x |
| XMP.4 (3) | 25–46 | — | No Peak | x | x |
| XMP.5 (67) | 142–163 | — | 18 | x | x |
| XMP.7 (54) | (90–99) × 2 | 69 | 27 | 50.00 | x |
| XMP.8 (8) | 90–99 | 79 | Mixture | >100.00 | x |
| XMP.9 (51) | 95–99, 90–99 | — | 29 | x | x |
| XMP.10 (55, 65) | 94–99, 90–99, 90–99 and 95–99, 90–99, 90–99 | — | Mixture | x | x |
| XMP.11 (13) | 148–151, 153–161 | — | 76 | x | x |
| XMP.12 (14) | 141–169 | — | 26 | >100.00 | x |
| XMP.13 (15) | 148–161 | 78 | 69 | 12.5 | 222 |
| XMP.13P (15) | 148–161 | 100 | 98 | 6.25 | x |
| XMP.14 (2) | 21–50 | — | — | x | x |
| XMP.15 (16) | 85–99, A @ 85 (I) | 66 | 57.6 | x | x |
| XMP.16 (17) | 85–99, A @ 86 (K) | — | 84.1 | x | x |
| XMP.17 (18) | 85–99, A @ 87 (I) | 86 | 77, 67 | x | x |
| XMP.18 (19) | 85–99, A @ 88 (S) | 66 | 70 | x | x |
| XMP.19 (20) | 85–99, A @ 89 (G) | — | 69 | x | x |
| XMP.20 (21) | 85–99, A @ 90 (K) | — | 66 | x | x |
| XMP.21 (22) | 85–99, A @ 91 (W) | 68 | 65.8 | x | x |
| XMP.22 (23) | 85–99, A @ 92 (K) | — | 66 | x | x |
| XMP.23 (24) | 85–99, A @ 94 (Q) | — | 69 | x | x |
| XMP.24 (25) | 85–99, A @ 95 (K) | — | 67 | x | x |
| XMP.25 (26) | 85–99, A @ 96 (R) | — | 73 | x | x |
| XMP.26 (27) | 85–99, A @ 97 (F) | — | 73 | x | x |
| XMP.27 (28) | 85–99, A @ 98 (L) | — | 65 | x | x |
| XMP.28 (29) | 85–99, A @ 99 (K) | — | 80 | x | x |
| XMP.29 (56) | (148–161) × 2 | — | 26 | >50 | >1469 |
| XMP.30 (52) | 90–99, 148–161 | — | 21 | x | >1653 |
| XMP.30-P (52) | 90–99, 148–161 | 95 | 98 | >50 | 1663 |
| XMP.31 (33) | 148–161, A @ 148 (K) | — | 68 | 6.25 | 426 |
| NMP.32 (34) | 148–161, A @ 149 (S) | — | 70 | 3.13 | 294 |
| XMP.33 (35) | 148–161, A @ 150 (K) | — | 58 | 6.25 | 603 |
| XMP.34 (36) | 148–161, A @ 151 (V) | — | 51 | 6.25 | 319 |
| XMP.35 (37) | 148–161, A @ 152 (G) | — | 72 | 3.13 | 442 |
| XMP.36 (38) | 148–161, A @ 153 (W) | — | 64 | 6.25 | 197 |
| XMP.37 (39) | 148–161, A @ 154 (L) | — | 51 | 6.25 | 253 |
| XMP.38 (40) | 148–161, A @ 155 (I) | — | 70 | 6.25 | 391 |
| XMP.39 (41) | 148–161, A @ 156 (Q) | — | 53 | 12.50 | 1792 |
| XMP.40 (42) | 148–161, A @ 157 (L) | — | 53 | 3.13 | 253 |

TABLE 1-continued

| Peptide # (Seq. ID No.) | Protein AA Segment | MS % Purity | HPLC % Purity | C. albicans MIC (μg/ml) | C. albicans pmol/ 30 mm² zone |
|---|---|---|---|---|---|
| XMP.41 (43) | 148–161, A @ 158 (F) | — | 63 | 3.13 | 734 |
| XMP.42 (44) | 148–161, A @ 159 (H) | — | 59 | 6.25 | 549 |
| XMP.43 (45) | 148–161, A @ 160 (K) | — | 53 | 12.50 | 785 |
| XMP.44 (46) | 148–161, A @ 161 (K) | — | 70 | 6.25 | 578 |
| XMP.45 (31) | 85–99, A @ 94 (Q) & 95 (K) | 71 | 46 | x | x |
| XMP.46 (57) | (90–99) × 2, A @ 1st 94 (Q) & 95 (K) | 67 | 47 | x | x |
| XMP.47 (58) | (90–99) × 2, A @ 2d 94 (Q) & 95 (K) | 57 | 34 | x | x |
| XMP.48 (59) | (90–99) × 2, A @ both 94 (Q) & 95 (K) | 68 | 33 | >50 | x |
| XMP.54 (5) | 21–35 | — | — | x | x |
| XMP.55 (61) | 152–172 | — | 28 | x | x |
| XMP.56 (47) | 85–99, K @ 94 (Q) & Q @ 95 (K) | — | 55 | x | x |
| XMP.57 (99) | Cys 85–99 Cys | 50 | Mixture | x | x |
| XMP.58 (9) | Cys-85–99 | 49 | 25.7 | x | x |
| XMP.59 (30) | 85–99, A @ 90 (K) & 92 (K) | 56 | 30.3 | x | x |
| XMP.60 (32) | 85–99, A @ 86 (K) & 99 (K) | 57 | 78.3 | x | x |
| XMP.61 (48) | 85–99, F @ 91 (W) | 60 | 59.8 | x | x |
| XMP.63 (53) | 85–99, 148–161 | 38 | 31.3 | x | >1006 |
| XMP.65 Rd (68) | Cys-85–99-Cys | 41 | 22, 34 | x | x |
| XMP.65 Ox (10) | Cys-85–99-Cys | — | No Peak | x | x |
| XMP.66 (49) | 85–99, $W_D$ @ 91 (W) | — | 70 | x | x |
| XMP.67 (50) | 85–99, β-(1-naphthyl)-A @ 91 | 65 | 52 | x | x |
| XMP.69 (60) | [90–99, A @ 94 (Q) & 95 (K)] × 3 | 44 | 54, 40 | x | x |
| XMP.70 (63) | 85–99, β-(3-pyridyl)-A @ 91 | 66 | 54 | x | x |
| XMP.71 (64) | $A_D$-$A_D$-85–99 | — | 60 | x | x |
| XMP.72 (66) | 85–99, β-(3-pyridyl)-A @ 97 (F) | — | 52 | x | x |
| XMP.73 (62) | 85–99, F @ 95 (K) | — | 44, 39 | x | x |
| XMP.74 (70) | 148–161, 90–99 | — | 29 | x | >2148 |
| XMP.75 (100) | IKKRAISFLGKKWQK (2-mixed) | — | 32 | x | x |
| XMP.76 (71) | 85–99, $F_D$ @ 95 (K) | 53 | 39 | x | x |
| XMP.77 (72) | 85–99, W @ 95 (K) | — | 38 | x | x |
| XMP.79 (73) | 85–99, K @ 94 (Q) | — | 48 | x | x |
| XMP.80 (74) | 85–99, β-(1-naphthyl)-A @ 95 (K) | 71 | 44 | x | x |
| XMP.81 (75) | 85–99, F @ 94 (Q) | 44 | 33, 35 | x | x |
| XMP.82 (76) | 148–161, W @ 158 (F) | 82 | 58 | 3.13 | 518 |
| XMP.83 (77) | 148–161, β(1-naphthyl)-A @ 153 (W) | 85 | 63 | x | 1804 |
| XMP.84 (78) | 85–99, β-(1-naphthyl) A @ 91 (W) & F @ 95 (K) | 64 | 50 | x | x |
| XMP.85 (79) | 148–161, L @ 152 (G) | 79 | 74 | x | >1881 |
| XMP.86 (80) | 148–161, L @ 156 (Q) | 69 | 51 | x | >2048 |
| XMP.87 (81) | 148–161, L @ 159 (H) | 79 | 63 | x | >1536 |
| XMP.88 (82) | 85–99, F @ 94 (Q) & 95 (K) | 62 | 50 | x | x |
| XMP.89 (84) | 85–99, β-(1-naphthyl) A @ 91 (W) & F @ 94 (Q) | 66 | 50 | x | x |
| XMP.90 (85) | 85–99, β-(1-naphthyl) A @ 91 (W), F @ 94 (Q) & 95 (K) | 70 | 63 | x | x |
| XMP.91 (86) | 148–161, F @ 156 (Q) | — | 31 | x | >3844 |
| XMP.92 (87) | 148–161, K @ 156 (Q) | — | 50 | 3.13 | 299 |
| XMP.93 (88) | 85–99 148–161 β-(1-naphthyl) A @ 91 (W), F @ 95 (K) | 72 | 38 | x | >980 |
| XMP.94 (89) | 148–161, F @ 159 (H) | — | 59 | x | >923 |
| XMP.95 (90) | 148–161, F @ 152 (G) | — | 57 | x | >1398 |
| XMP.96 (101) | 148–161, F @ 161 (K) | — | 60 | x | 1856 |
| XMP.97 (92) | 148–161, K @ 152 (G) | — | 67 | 3.13 | 213 |
| XMP.98 (83) | 90–99, β-(1-naphthyl) A @ 91 (W), F @ 95 (K) + 148–161 F @ 156 (Q) | 69 | 31 | x | x |
| XMP.99 (93) | [90–99, W @ 95 (K)] × 3 | — | — | x | x |
| XMP.100 (94) | 148–161, K @ 152 (G) & 156 (Q) | — | 61 | 6.25 | 462 |
| XMP.101 (95) | (148–161) × 2[K @ 152 (G) & 156 (Q), F @ 159 (H) & 161 (K)] | — | 16 | x | x |
| XMP.102 (96) | 90–99 (F @ 95 (K)) + 148–161 L | — | 16 | x | x |

TABLE 1-continued

| Peptide # (Seq. ID No.) | Protein AA Segment | MS % Purity | HPLC % Purity | C. albicans MIC (µg/ml) | C. albicans pmol/ 30 mm² zone |
|---|---|---|---|---|---|
| | @ 156 (Q) | | | | |
| XMP.103 (102) | 85–99, W @ 94 (Q) | — | 28 | x | 1151 |
| XMP.104 (103) | 148–161, S @ 156 (Q) | — | 34 | x | >5569 |
| XMP.105 (104) | 85–99, β-(1-naphthyl)-A @ 94 (Q) | 58 | 43 | x | 1565 |
| XMP.106 (105) | 148–161, T @ 156 (Q) | — | 26 | x | 1032 |
| XMP.107 (106) | 148–161, W @ 159 (H) | — | 55 | x | >2796 |
| XMP.108 (107) | 148–161, W @ 161 (K) | — | 50 | x | >3219 |
| XMP.109 (108) | 148–161, β(1-naphthyl)-A @ 158 (F) | — | 41 | x | x |
| XMP.110 (109) | 148–161, β(1-naphthyl)-A @ 159 (H) | — | 56 | x | x |
| XMP.111 (110) | 148–161, β(1-naphthyl)-A @ 161 (K) | — | 73 | x | x |
| XMP.112 (111) | 85–99, β(1-naphthyl)A @ 91 (W) & 95 (K) | — | 56 | x | x |
| XMP.113 (112) | 148–161, F @ 157 (L) | — | 46 | x | x |
| XMP.114 (113) | KWQLRSKGKIKIFKA | — | 17 | x | x |
| XMP.116 (114) | 148–161, K @ 152 (G), β(1-naphthyl)A @ 153 (W) | — | 72 | x | 670 |
| XMP.119 (115) | 85–99, β(1-naphthyl)A @ 91 (W) & 94 (K) | — | 77 | x | x |
| XMP.120 (116) | 85–99, K @ 97 (F) | — | 52 | x | x |
| XMP.121 (117) | 85–99, β(1-naphthyl)A @ 94 (Q) & 95 (K) | 65 | 35 | x | x |
| XMP.122 (118) | 85–99, β(1-naphthyl)A @ 91 (W), 94 (Q) & 95 (K) | — | 46 | x | x |
| XMP.123 (119) | 148–161, p-Amino-F @ 156 (Q) | — | 64 | 12.50 | 1721 |
| XMP.124 (120) | 148–161, K @ 152 (G), W @ 158 (F) | — | 67 | 6.25 | 351 |
| XMP.125 (121) | 148–161, Y @ 156 (Q) | — | 54 | 25.00 | >3150 |
| XMP.126 (122) | 148–161, $W_D$ @ 153 (W) | 66 | 54 | 25.00 | 1404 |
| XMP.127 (123) | 148–161, F @ 153 (W) | 65 | 63 | 3.13 | 226 |
| XMP.128 (124) | 148–161 $F_D$ @ 153 (W) | 63 | 51 | 25.00 | 1179 |
| XMP.129 (125) | 148–161, 1-β(1-naphthyl)$A_D$ @ 153 (W) | 24 | 28 | 25.00 | 2117 |
| XMP.130 (126) | 148–161, 2-β(1-naphthyl)A @ 153 (W) | 55 | 80 | 50.00 | 1159 |
| XMP.131 (127) | 148–161, 2-β(1-naphthyl)$A_D$ @ 153 (W) | 75 | 60 | 50.00 | 2493 |
| XMP.132 (128) | 148–161, Pyr-A @ 153 (W) | 49 | 50 | 12.50 | 353 |
| XMP.133 (129) | 148–161, p-Amino-F @ 153 (W) | 63 | 47 | 12.50 | 284 |
| MAP.134 (130) | 148–161, p-Amino-F @ 152 (G) | — | 68 | 12.50 | 1255 |
| XMP.135 (131) | 148–161, K @ 153 (W) | — | 70 | 6.25 | 428 |
| XMP.136 (132) | 85–99, E @ 95 (K) | — | 50 | x | x |
| XMP.137 (133) | Cys-148–161-Cys | — | 28 | x | >2286 |
| XMP.138 (134) | 148–161, K @ 152 (G), F @ 153 (W) | — | 61 | 3.13 | 257 |
| XMP.139 (135) | 148–161, Y @ 153 (W) | — | 60 | 6.25 | 323 |
| XMP.140 (136) | 90–99 β(1-naphthyl)A @ 94 (Q) & 95 (K) + 104 | — | 26 | x | x |
| XMP.141 (137) | 85–99, W @ 97 (F) | — | 50 | x | x |
| XMP.142 (138) | 148–161, W @ 157 (L) | — | 57 | 12.50 | 1244 |
| XMP.143 (139) | 148–161, β(1-naphthyl)A @ 157 (L) | — | 65 | 25.00 | >2839 |
| XMP.144 (140) | 148–161, Cyclohexyl-A @ 153 (W) | — | 60 | 12.50 | 695 |
| XMP.145 (141) | 90–99, β(1-naphthyl)A @ 94 (Q) & 95 (K) + 148–161 | — | 20 | x | >1887 |
| XMP.146 (142) | 148–161, β(1-naphthyl)A @ 159 (H) & 161 (K) | — | 53 | >50.00 | >2717 |
| XMP.147 (143) | 85–99 K @ 96 (R) | — | 55 | 100 | >2558 |
| XMP.148 (144) | 148–161, β(1-naphthyl)A @ 153 (W) & 159 (H) | — | 62 | 50.00 | >2805 |
| XMP.149 (147) | KWKVFKKIEK + 148–161 | — | 27 | 12.50 | >1,397 |
| XMP.150 (148) | KWAFAKKQKKRLKRQWLKKF | — | Mixture | x | >2,380 |
| XMP.151 (55) | 94–99, 90–99, 90–99 | — | 14 | x | x |
| XMP.152 (65) | 95–99, 90–99, 90–99 | — | 21 | x | x |
| XMP.153 (149) | (90–99) × 3 | — | 17 | x | x |
| XMP.154 (150) | (90–99) × 2, β(1-naphthyl)A @ 1st 94 (Q) & 95 (K) | — | 31 | >100.00 | x |
| XMP.155 (151) | (90–99) × 2, β(1-naphthyl)A @ 2nd 94 (Q) & 94 (K) | — | 23 | >100.00 | x |
| XMP.156 (152) | (90–99) × 2, β(1-naphthyl)A | — | 38 | >100.00 | x |

TABLE 1-continued

| Peptide # (Seq. ID No.) | Protein AA Segment | MS % Purity | HPLC % Purity | C. albicans MIC (µg/ml) | pmol/ 30 mm² zone |
|---|---|---|---|---|---|
| | @ both 94 (Q) & 95 (K) | | | | |
| XMP.157 (153) | (90–99, β(1-naphthyl)A @ 94 (Q) & 95 (K)) × 3 | — | 38 | >100.00 | x |
| XMP.158 (154) | 85–99, 148–161, β(1-naphthyl)A @ 94 (Q) & 95 (K) | — | 16 | >100.00 | x |
| XMP.159 (155) | (90–99, β(1-naphthyl)A @ 91 (W) & 95 (K)) + 82 | — | 23 | 50.00 | x |
| XMP.160 (156) | (90–99) × 2, β(1-naphthyl)A @ both 91 (W) & 95 (K) | — | 32 | >100.00 | x |
| XMP.161 (157) | 148–161, K @ 152 (G) & A @ 153 (W) | — | 75 | 3.13 | x |
| XMP.162 (158) | 90–99, 148–161, W @ 95 (K) | — | 21 | x | x |
| XMP.163 (159) | (90–99) × 2, W @ both 95 (K) | — | Mixture | x | x |
| XMP.164 (160) | (90–99) × 2, β (1-naphthyl)A @ both 94 (Q) | — | 46 | x | x |
| XMP.165 (161) | (90–99, β (1-naphthyl)A @ 91 (W) & F @ 95 (K)) × 2 | — | 72 | x | x |
| XMP.166 (162) | 148–161, V @ 153 (W) | — | 68 | 3.13 | 170.65 |
| XMP.167 (163) | 90–97 | — | 56 | >50.00 | x |
| XMP.168 (164) | C-90–101-C | — | 13 | >100.00 | x |
| XMP.169 (165) | C-90–97-C | — | 20 | >100.00 | x |
| XMP.170 (227) | 90–101 | — | 69 | >50.00 | x | x = Not tested

EXAMPLE 2

IN-VIVO ANTI-FUNGAL EFFECT OF BPI PROTEIN PRODUCTS IN MICE WITH SYSTEMIC CANDIDA INFECTION

This example addresses the in vivo anti-fungal effect of BPI protein products, specifically BPI-derived peptides, in mitigating the total mortality or mortality rate of mice systemically infected with Candida albicans. BPI-derived peptides that had been screened for anti-fungal activity in the radial diffusion and broth assays described in Example 1 were prepared as described in Example 1 and purified as follows.

Fungicidal peptides selected for additional studies were synthesized on a large scale. Peptides were made using solid phase peptide synthesis on an Advanced Chemtech (ACT-Model 357 MPS) synthesizer utilizing a 1-Fluorenylmethyloxycarbonyl (Fmoc) protection strategy with a double coupling procedure employing N,N-diisopropylcarbodiimide (DIC)/1-hydroxybenzotriazole (HOBt and 2-(1-H-benzotriazol-1-yl)-1,1,3,3,-tetramethyluronium hexafluorophosphate (HBTU)/HOBt/diisopropylethylamine (DIEA).

The solid support used was a polystyrene resin with 1% divinylbenzene (DVB) cross-linking and an 4-(2',4'-dimethoxyphenyl-Fmoc-aminomethyl)-phenoxy (Fmoc-Rink amide) linker with a substitution rate of 0.44 mmoles/gram. The scale used was between 0.5 grams and 5 grams of starting resin. Peptides were purified by HPLC, using a Waters Prep LC 2000 Preparative Chromatography System (Water Corp., Milford, Mass.) equipped with a Delta Pak C-18, 15 um, 300 A cartridge column consisting of a 40×10 mm guard cartridge and a 40×100 mm Prep Pak cartridge. The column was equilibrated in 25% buffer B, where A=5% acetonitrile/0.1% trifluoroacetic acid and B=80% acetonitrile/0.065% trifluoroacetic acid. Peptides were dissolved to ~20 mg/mL in buffer A and 200–800 mg were applied to the column through the LC pump operating at a flow rate of 8 mL/min. Bound material was eluted with gradient of 25–35% buffer B/30 min applied at 8 mL/min. (Some peptides were purified with a gradient of 23–33%B/30 min). The eluate was monitored at both 220 and 280 nm with a Waters 490E Programmable Multiwavelength Detector. Fractions were collected and assayed for the peptide of interest on an Ultrafast Micoprotein Analyzer (Michrom BioResources, Inc., Pleasanton, Calif.) equipped with a Zorbax C-8, 150×1 mm, 5 um, 300 A maintained at 40° C. Fractions containing the peptide of interest at >95% purity were pooled and lyophilized to dryness.

Figure 2:
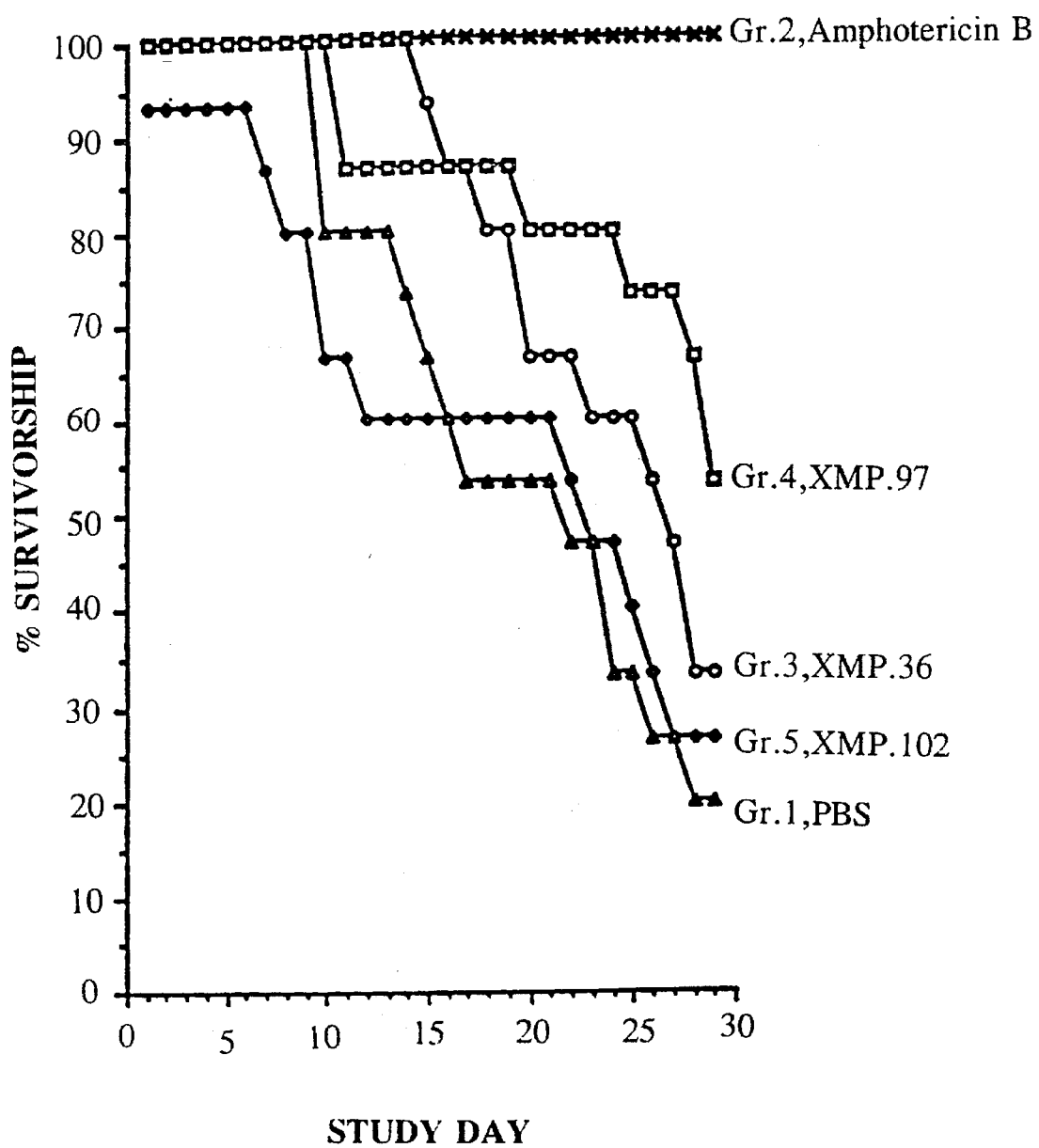
FIGS. 2 and 3 graphically represent survival data in mice after C. albicans challenge and treatment with BPI-derived peptides or buffer.

Five groups of 15 male DBA/2J mice at age 6–8 weeks (Jackson Laboratory, Bar Habor, Me.) were inoculated with $1.24 \times 10^5$ C. albicans (batch SLU-1 from St. Louis University Medical Center, Mo.) by intravenous injection into the tail vein. A Candida inoculation of $1 \times 10^5$ results in an $LD_{80}$ over 28 days in this model. Immediately after fungal challenge, the mice were intravenously injected via the tail vein with 10 mg/kg XMP.36, 5 mg/kg XMP.97, 10 mg/kg XMP.102, 1 mg/kg amphotericin B (Sigma, St. Louis, Mo.), or 0.1 mL of phosphate buffered saline (PBS) as a control. Treatment with the same amounts of BPI protein products was repeated at Day 2 and Day 4 (except that the second dose of XMP.36 was given at a dose of 5 mg/kg). Mice were monitored twice daily for mortality until termination of the study at Day 28. The mortality data, displayed in FIG. 2, show that 100% of the mice treated with amphotericin B survived, 53% of mice treated with XMP.97 survived ($p<0.05$ compared to control), 33% of mice treated with XMP.36 survived, 27% of mice treated with XMP.102 survived, and 20% of mice treated with PBS survived until Day 28. In FIG. 2, the symbol "X" represents survival after treatment with amphotericin B; open squares, treatment with XMP.97; open circles, treatment with XMP.36; open diamonds, treatment with XMP.102; and open triangles, treatment with buffer. Statistical significance was evaluated using the Lifetest Survival Curve analysis. [Lawless, Statistical Models and Methods for Lifetime Data, John Wiley & Sons, New York (1982).] The duration and almost linear decline in survival is analogous to human opportunistic candidiasis.

Figure 3:
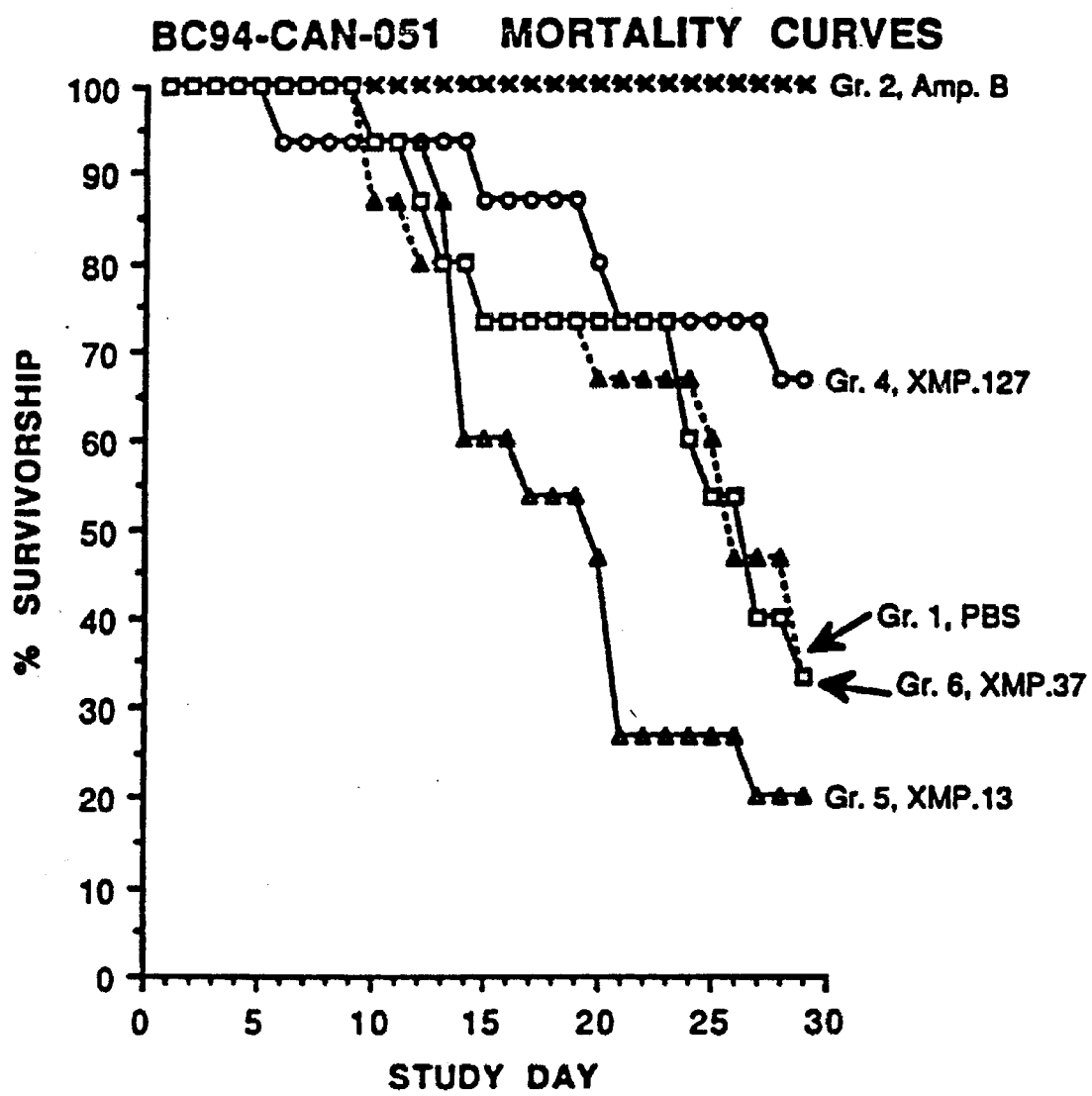

A second experiment was conducted on five groups of 15 mice, with a fungal challenge of $0.5 \times 10^5$ C. albicans, followed by treatment at Day 0, Day 2 and Day 5 with 10 mg/kg XMP.127, 5 mg/kg XMP.13, 5 mg/kg XMP.37, 1 mg/kg amphotericin B, or 0.1 mL PBS as a control. The mortality data, displayed in FIG. 3, show that 100% of the mice treated with amphotericin B survived, 67% of mice treated with XMP.127 survived (p<0.05 compared to control), 33% of mice treated with XMP.37 survived, 20% of mice treated with XMP.13 survived, and 33% of mice treated with PBS survived until Day 28. In FIG. 3, the symbol "X" represents survival after treatment with amphotericin B; open circles, treatment with XMP.127; filled triangles, treatment with buffer; open squares, treatment with XMP.37; open triangles, treatment with XMP.13.

In these studies, amphotericin B was completely protective, as expected. The effect of XMP.102, a control peptide without anti-fungal activity, was no different than PBS. The data demonstrate that administration of BPI-derived peptides XMP.97 and XMP.127 to mice challenged systemically with C. albicans unexpectedly provided a significant reduction in mortality compared to buffer-treated controls.

Further experiments are performed to confirm the anti-fungal activity of BPI protein products on strains of Candida considered resistant to other anti-fungal agents: polyene-resistant C. albicans (ATCC Accession No. 38247), 5-fluorocytosine-resistant C. albicans (ATCC No. 44373), azole-resistant C. albicans (ATCC No. 62342), and ketoconazole-resistant C. albicans (ATCC No. 64124).

EXAMPLE 3

IN VITRO AND IN VIVO EFFECT OF BPI PROTEIN PRODUCTS ON A VARIETY OF FUNGAL SPECIES

The anti-fungal activity of BPI protein products is evaluated in vitro, e.g., in broth assays, and in vivo in animal models for a variety of fungal species, including Cryptosporidium parvum, Cryptococcus neoformans and Histoplasma capsulatum. Animal models for C. parvum include severe combined immunodeficiency (SCID) mouse models and a colostrum-deprived SPF piglet model.

EXAMPLE 4

IN VIVO ANTI-FUNGAL EFFECT OF BPI PROTEIN PRODUCTS IN CANDIDA-INFECTED NEUTROPENIC RATS

This example addresses the in vivo testing of BPI protein products for anti-fungal activity, and specifically the efficacy of a BPI protein product, rBPI$_{23}$, in blunting or preventing symptoms of infection and sequelae thereof, including septic shock progression, following infection of neutropenic rats with a massive and lethal dose of a yeast-phase suspension of a clinical isolate of Candida albicans. Treatment of the rats with rBPI$_{23}$ (n=6 rats) was compared to treatment with thaumatin (n=5 rats), a control protein having a similar molecular weight and charge but without rBPI$_{23}$'s microbicidal effects. During an initial experiment of overwhelming infection with Candida organisms in immunocompromised host animals, animals were monitored for multiple indices including: survival through 24 hours post-infection, systemic arterial pressure, pulse, respiration rate and core temperature, blood cell counts and blood gases, circulating colony-forming units (CFU) of Candida, and the microvascular permeability and histopathology of lungs, livers, hearts, and kidneys. Under such conditions of overwhelming infection, treatment with BPI protein may be expected to have little or no effect on survival but may have effects on other indices monitored during infection.

Specifically, the following procedures were followed. Male Sprague-Dawley rats (initial weight=280–300 g, specific pathogen-free; Harlan, Indianapolis, Ind.) were caged in isolation and permitted free access to food and water before and during experiments. Absolute neutropenia (defined as a combined segmented and band neutrophil count<500 PMN/µl) listing 4–7 days was induced in these animals with 100 mg/kg cyclophosphamide (using a 20 mg/ml solution reconstituted from crystals in sterile phosphate-buffered saline, pH 7.4; Sigma, St. Louis, Mo.) injected intraperitoneally 4 days prior to infection with Candida. On the day before infection, animals were anesthetized with ketamine:xylazine (2:1, 0.9 ml/kg, injected intramuscularly), and the left carotid artery and right jugular vein were aseptically catheterized. Animals received 2.5 mg amikacin sulfate and 300 mg penicillin intravenously immediately after catheterization surgery.

Cultures of Candida albicans (CA) of the CA-1 strain were maintained by weekly transfer to Saboumud dextrose agar slants containing penicillin/streptomycin at 28° C.; these were transferred to Sabouraud's broth, incubated at 37° C. in a shaking water bath for 48–72 hours, and resuspended in fresh Sabouraud's broth for 24 hours before use. Yeast-phase CA Colastoconidia) for infusions were sedimented at 400 ×g for 10 min at 4° C.), washed twice in saline, and resuspended in saline to $1 \times 10^9$ organisms/ml using serial dilutions and a hemacytometer, and kept at 4° C. until use. Endotoxin levels in CA infusates were ≦30 pg/ml as assayed by a quantitative chromogenic Limulus amebocyte lysate assay (Whittaker M. A. Bioproducts, Walkersville, Md.). Viability of CA inocula were confirmed by trypan blue exclusion to be >99%, and microscopic examination before use showed no germination. For CA inocula enumerated as $1 \times 10^9$/ml, the actual colony forming units (CFU) were determined to be $5.7 \pm 0.2 \times 10^8$ CFU/ml (mean±SEM) by streak-plated serial dilutions on Sabouraud's dextrose agar at 3° C. for 24 hours.

Animals were treated with 2 mg/ml solutions of either rBPI$_{23}$ or the control protein, thaumatin (both in 150 mM NaCl, 5 mM Na-citrate, pH 5.0) before and after CA infection. Five minutes before the start of the CA infusion, rBPI$_{23}$ or thaumatin was administered as a 6.6 mg/kg intravenous bolus. The rats were then infected with a massive infusion of organisms over 30 min. (Sage Pump, Cambridge, Mass.) [$1 \times 10^9$ CA in 1 ml which yields an LD$_{100}$ in less than 12 hours]. T=0 was considered to be the time at which the CA infusion was completed. Immediately after infection the rats were administered rBPI$_{23}$or thaumatin as a continuous intravenous infusion of 6.6 mg/kg/hour for 4 hours, followed by a saline infusion of 1 ml/hour for the next 4 hours. Infected animals received additional antibiotics (2.5 mg amikacin sulfate and 300 mg penicillin, intravenously) at T=30 min. after the completion of CA infusion. Six neutropenic control rats were sham-infected with saline and received neither rBPI$_{23}$ nor thaumatin treatment.

Hemodynamic and vital signs were recorded every 30 min. Arterial pressure (mm Hg) and pulse rates (beats/min.) were continuously recorded on a multichannel physiograph (MK-III-S; Narco Bio-Systems, Houston, Tex.). Respiratory frequency (breaths/min.) was assessed by direct observation, and rectal temperature (°C.) was measured by a miniprobe (Diatek, San Diego, Calif.). A baseline arterial blood sample (1.5 ml) was obtained after a 30 min. equilibration, and additional arterial blood samples were taken at T=1.5 and 4.5 hours (or at death, if occurring earlier). After each blood sample, isovolumetric saline was given via the jugular catheter. These blood samples underwent duplicate analyses of microhematocrit, blood gases using an IL-1306 machine (Instrumentation Laboratory, Lexington, Mass.), total leukocyte and platelet counts by phase microscopy), differential leukocyte counts (Diff-Quik; Baxter, Miami, Fla.), and quantitative blood culture (results in FIG. 6).

Any animal which exhibited convulsions or increasingly severe respiratory distress was humanely sacrificed and was counted as having survived the previous time point. At death, the cranial lobe of the right lung was excised after bronchial ligation for determination of wet/dry weight ratio (W/D), which is an index of altered microvascular permeability and edema, by drying to constant weight at 70° C. Left lungs were fixed in situ with cacodylate-buffered glutaraldehyde for 30 min. at a transpulmonary inflation pressure of 20–22 cm $H_2O$, followed by fixation of 2–3 mm midlobar slices in fresh glutaraldehyde overnight at 5° C. before dehydration and embedding in parafin. Serial 6 μm lung sections were stained with hematoxylin and eosin for routine histopathology, periodic acid-Schiff (PAS) to identify yeast, and chloroacetate esterase (CAE) to stain neutrophil granules. Liven, hearts, and kidneys were excised, and standardized tissue sections from these organs were also isolated for W/D determinations, or immersion-fixed in buffered formalin and processed as described above for lung.

Data are presented as means±SEM, with sequential changes for intra- and intergroup variables analyzed by repeated-measures ANOVA and post-hoc comparisons using a Newman-Keuls test. Mortality data were analyzed using Fisher's exact test. Statistical significance was accepted for P-values <0.05.

In this initial experiment, in response to the massive dose of $1\times10^9$ CA, neutropenic rats developed lethal fungemic infection which progressed to shock within 6 hours and which, under these conditions, was not delayed or prevented by treatment with $rBPI_{23}$. It should be noted that the rapid onset of lethal shock in many animals resulted in small n-values at later sampling time points. Although no effect on survival was demonstrated with this dose of $1\times10^9$ CA, these $BPI_{23}$-treated rats showed statistically significant enhanced intravascular clearance of circulating CA at 1.5 and 4.5 hours relative to animals receiving thaumatin (p<0.05; see quantitative blood culture results in FIG. 6). Such an antifungal effect is surprising and highly significant because reduction of circulating Candida levels even by a factor of 10 can be an important factor in therapeutic success.

Figure 4:
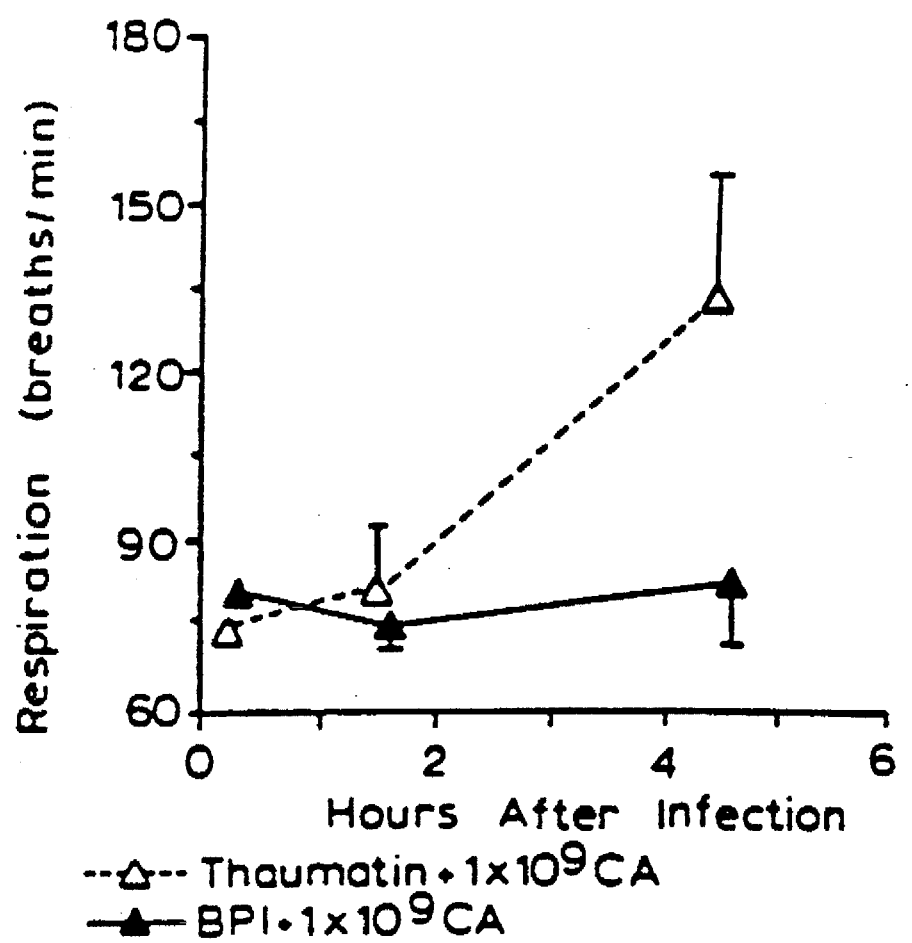
FIG. 4 graphically represents respiration rate in rats after C. albicans infection and treatment with $rBPI_{23}$ or thaumatin.
Figure 5:
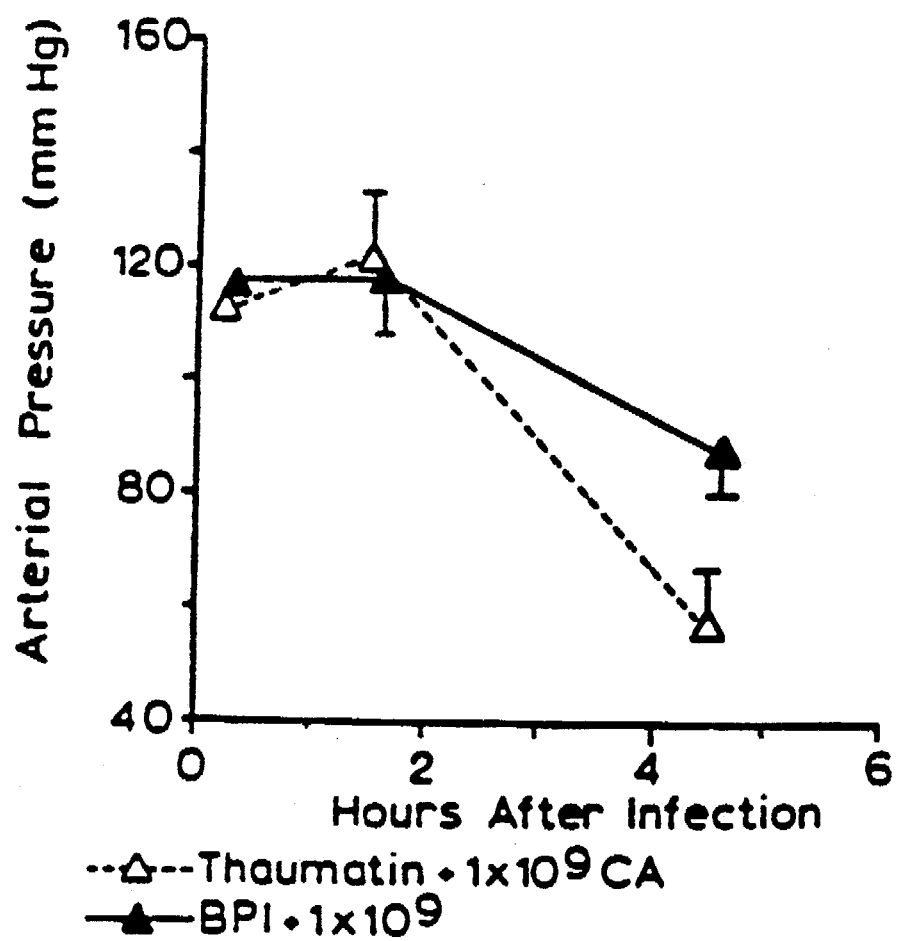
FIG. 5 graphically represents arterial blood pressure in rats after C. albicans infection and treatment with $rBPI_{23}$ or thaumatin.
Figure 6:
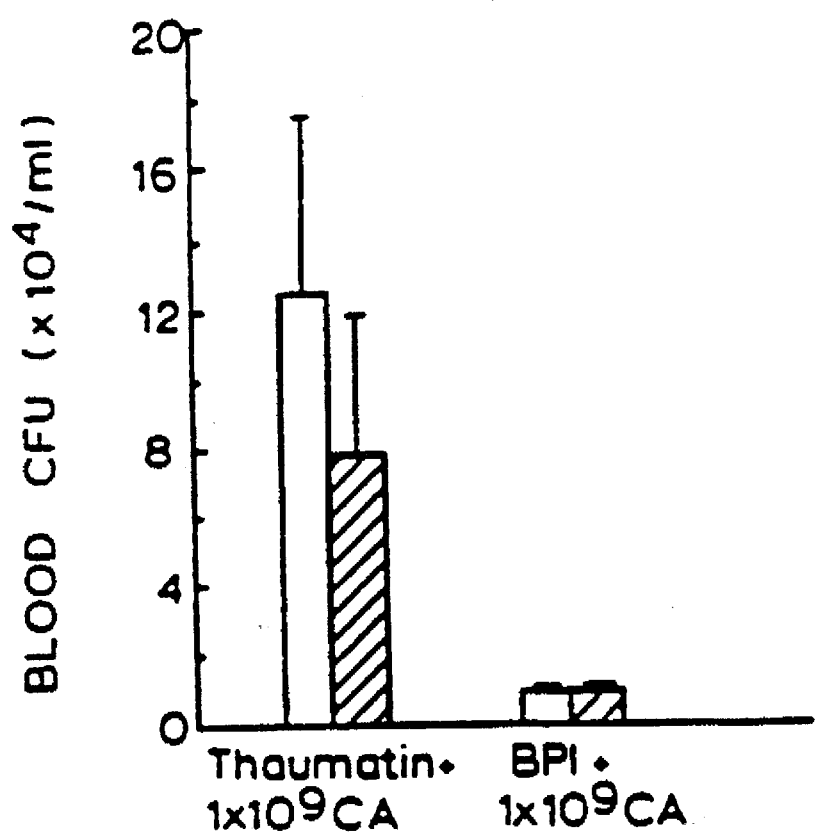
FIG. 6 graphically represents the number of circulating C. albicans colony forming units in rats after infection and treatment with $rBPI_{23}$ or thaumatin.

With this dose of $1\times10^9$ CA organisms, treatment with $rBPI_{23}$ (vs. control protein) did not consistently delay the onset of systemic hypotension and tachypnea with respiratory distress following CA infection. Fungemic circulatory failure in both thaumatin- and $rBPI_{23}$-treated rats was preceded by bradycardia and hypotension which were remarkably abrupt in onset, with the $1\times10^9$ CA-infected animals progressing from hemodynamic stability to death within 15–30 min. Although $rBPI_{23}$ did not prolong survival time among such candidemic animals, it did attenuate the severe tachypnea (FIG. 4) and hypotension (FIG. 5) noted by 4.5 hours (or at death, if earlier) in the $1\times10^9$ CA-infected rats treated only with control protein. Thus, $rBPI_{23}$ had unexpected beneficial effects in this model of overwhelming CA infection, by dramatically enhancing the introvascular clearance of circulating organisms as shown in FIG. 6 above and by stabilizing both cardiopulmonary indices and vital signs during CA-induced sepsis as shown in FIGS. 4 and 5. Higher or more sustained doses of BPI protein product are expected to achieve greater beneficial effects in this model. BPI protein product is also expected to provide even better effects at the lower levels of CA seen during relevant clinical CA infection.

Figure 7:
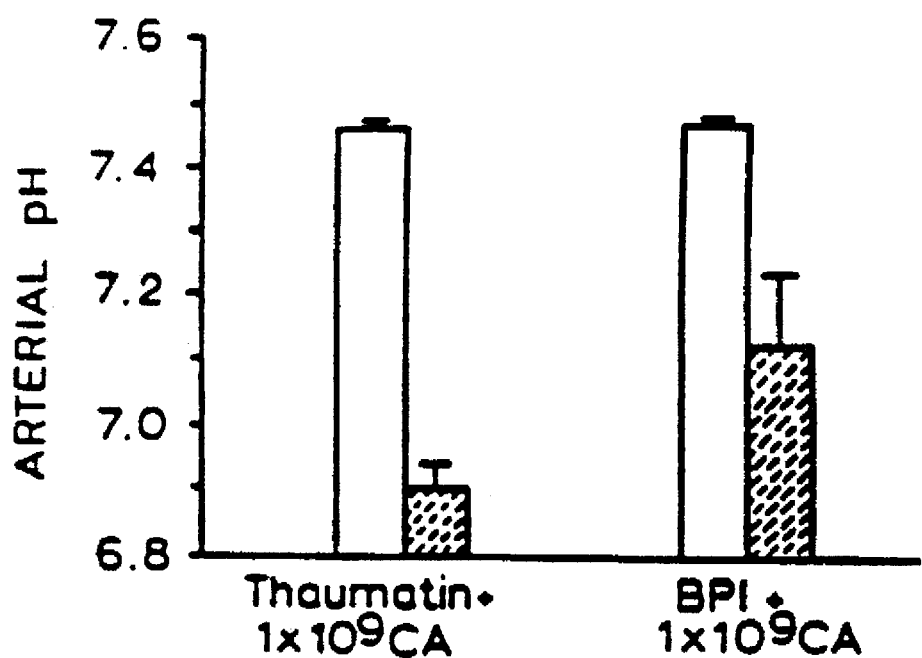
FIG. 7 graphically represents arterial pH in rats after C. albicans infection and treatment with $rBPI_{23}$ or thaumatin.
Figure 8:
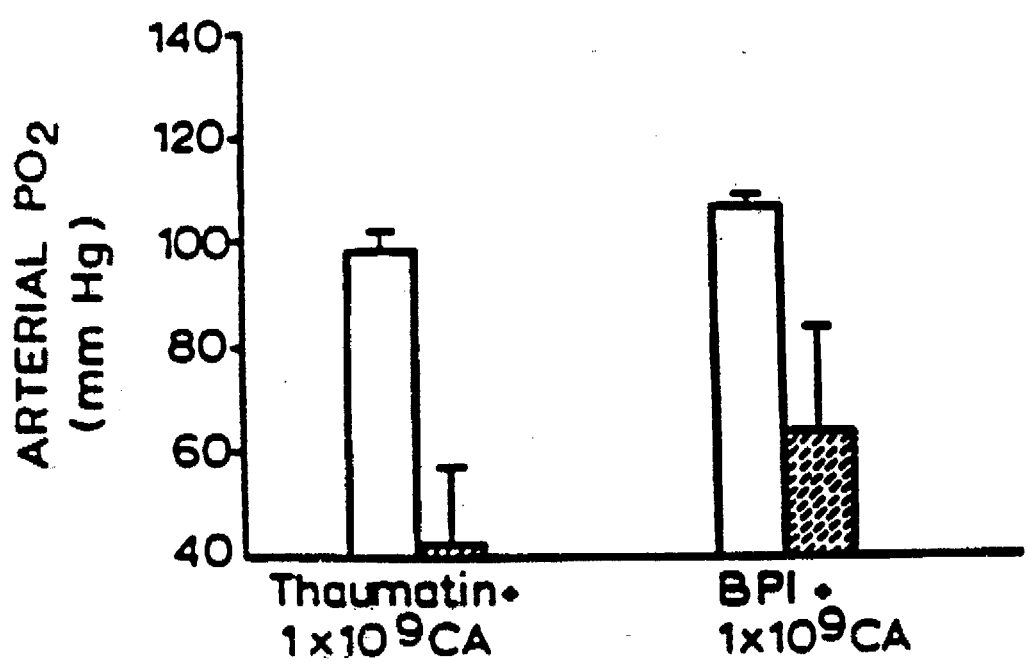
FIG. 8 graphically represents arterial $PO_2$ in rats after C. albicans infection and treatment with rBPI23 or thaumatin.

Lethal candidemia in thaumatin-treated rats was associated with significant arterial acidemia, hypoxemia, and hypercarbia by death at 3–6 hours. Treatment with $rBPI_{23}$ slightly attenuated both the arterial acidemia (FIG. 7) and hypoxemia (FIG. 8) during candidemic shock. In all rats studied, the baseline hematological indices of arterial hematocrit, total leukocyte counts, and platelet counts reflected respectively the slight, severe, and moderate decreases induced by cyclophosphamide in this animal model. Higher hematocrits among candidemic rats reflect hemoconcentration due to plasma extravasation, a result which was slightly attenuated by $rBPI_{23}$ treatment when compared to results for candidemic animals receiving the control protein thaumatin. Although total arterial leukocyte counts were low at baseline due to pre-treatment with cyclophosphamide, there was a gradual onset of leukopenia among candidemic rats, and there were no significant differences in leukocyte counts between the $rBPI_{23}$ and thaumatin treatment groups. Finally, all infected rats developed significant arterial thrombocytopenia, which was evident by 4.5 hours (or at death, if earlier) among candidemic animals; treatment with $rBPI_{23}$ did not alter the magnitude or kinetics of peripheral platelet loss compared to thaumatin for any CA-infected group.

Compared to neutropenic control rats which were sham-infected with saline, candidemic rats injected with $1\times10^9$ organisms as described and treated with either control protein (thaumatin) or BPI protein product ($rBPI_{23}$) had significantly elevated lung wet/dry weight ratios (W/D) but had lesser increases in liver W/D and kidney W/D. Histological examination of lungs from these animals dying of infection by $1\times10^9$ CA revealed that treatment with $rBPI_{23}$ did not alter the rapid development of hemorrhagic pulmonary edema, characterized by severe perivascular and peribronchiolar cuffing and extensive alveolar flooding with fibrin deposition. *Candida blastoconidia* were observed erupting directly into alveolar airspaces from intravascular yeast aggregates as germinating hyphae. Histological changes in the liver were also severe, with hepatocytes showing both complete glycogen depletion and zonal vacuolation with progressive distance from portal triads and adjacent to germinating CA which had been phagocytized but not killed by sinusoidal Kupffer cells. Although other tissues contained germinated yeast as well, notably the heart and kidney, the overall appearance of these organs was unremarkable except for focal masses of CA hyphae.

EXAMPLE 5

IN VIVO ANTI-FUNGAL EFFECT OF BPI PROTEIN PRODUCTS IN CANDIDA NEUTROPENIC RATS

This example addresses additional in vivo experiments in view of the beneficial effects of BPI protein product treatment on overwhelming Candida infection (i.e., $1\times10^9$ CA organism dose, as described in Example 2) including specifically the significant reduction of *C. albicans* colony-forming units in circulation brought about by BPI protein product administration. Additional experiments are carried out using the neutropenic rat model of Candida infection described in Example 2 but wherein lower doses of CA organisms are administered in the animal model and/or increased dosages of BPI protein products are administered, in the same or longer time course, either alone or in combination with known anti-fungal agents. Such experiments are designed to test in a model system designed to more closely approximate typical responses to casual CA infection, the efficacy of BPI protein products in treating fungal infection, including, e.g., protecting against death and fungemic shock.

Numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed is:

1. A method of treating fungal infections comprising administering to a subject suffering from a fungal infection a therapeutically effective amount of a bactericidal/permeability-increasing (BPI) protein product.

2. The method of claim 1 wherein the BPI protein product is selected from the group consisting of BPI holoprotein, rBPI$_{23}$ or rBPI$_{21}$.

3. The method of claim 1 wherein the BPI protein product is a BPI-derived peptide selected from the group consisting of XMP.97 (SEQ. ID NO: 92) and XMP.127 (SEQ. ID NO: 123).

4. The method of claim 1 wherein the BPI protein product is administered intravenously.

5. The method of claim 1 wherein the BPI protein product is administered as an aerosol.

6. The method of claim 1 wherein the BPI protein product is a BPI-derived peptide having an amino acid sequence of BPI protein from about position 142 to about position 169, subsequences thereof and variants of the sequence or subsequence thereof, which possess anti-fungal activity.

7. The method of claim 1 wherein the BPI protein product is administered at dosages from about 100 μg/kg to about 100 mg/kg of body weight.

8. The method of claim 1 wherein the BPI protein product is an N-terminal fragment of BPI or dimeric form thereof.

9. The method of claim 8 wherein the N-terminal fragment has a molecular weight of approximately between 21 kD and 25 kD determined by SDS-PAGE analysis.

10. The method of claim 1 wherein the fungal infection involves a fungal species selected from the group consisting of Candida, Aspergillosis, and Cryptococcus species.

11. The method of claim 10 wherein the fungal species is C. albicans.

12. The method of claim 1 comprising the additional step of administering a non-BPI anti-fungal agent.

13. The method of claim 12 wherein the non-BPI anti-fungal agent is amphotericin B.

14. The method of claim 12 wherein the non-BPI anti-fungal agent is fluconazole.

15. A method of killing or inhibiting replication of fungi comprising contacting the fungi with a bactericidal/permeability-increasing (BPI) protein product.

16. The method of claim 15 further comprising contacting the fungal species with an anti-fungal agent.

* * * * *

UNITED STATES PATENT AND TRADEMARK OFFICE
CERTIFICATE OF CORRECTION

PATENT NO.    : 5,627,153
DATED         : May 6, 1997
INVENTOR(S)   : Little et al.

It is certified that error appears in the above-identified patent and that said Letters Patent is hereby corrected as shown below:

Column 1,
Line 34, "haft of" should be -- half of --.
Line 55, "Inflammation." should be -- Inflammation: --.
Line 65, "$10^6$" should be -- $10^{-6}$ --.

Column 2,
Line 49, "actinnomycin" should be -- actinomycin --.
Line 54, "beating," should be -- bearing, --.

Column 4,
Line 20, "serf-limited" should be -- self-limited --.
Line 53, "amphoteficin" should be -- amphotericin --.
Line 54, "amphoteficin" should be -- amphotericin --.

Column 5,
Line 7, "eases," should be -- cases, --.
Line 9, "bum" should be -- burn --.
Line 13, "Amphoteficin" should be -- Amphotericin --.
Line 17, "bums" should be -- burns --.
Line 22, "funga" should be -- fungal --.
Line 30, "bum" should be -- burn --.

Column 8,
Line 37, "rBPI23" should be --$rBPI_{23}$ --.
Line 61, "drag," should be -- drug, --.
Line 63, ""Effective" should be -- Effective --.
Line 65, "contemplated"" should be -- contemplated --.

Column 14,
Line 64, "XMP.13," should be -- (XMP.13, --.

Column 15,
Line 11, "robes" should be -- tubes --.

Column 16,
Line 15, "ID) NOS:" should be -- ID NOS: --.

UNITED STATES PATENT AND TRADEMARK OFFICE
CERTIFICATE OF CORRECTION

PATENT NO.    : 5,627,153
DATED         : May 6, 1997
INVENTOR(S)   : Little et al.

It is certified that error appears in the above-identified patent and that said Letters Patent is hereby corrected as shown below:

Column 21,
Line 48, "(HOBt and" should be -- (HOBt) and --.

Column 24,
Line 29, "Colastonconidia)" should be -- (blastoconidia) --.
Line 30, "4°C.)." should be -- 4°C. --.

Column 25,
Line 9, "microscopy)" should be -- microscopy --.
Line 27, "Liven," should be -- Livers, --.

Signed and Sealed this

Twenty-sixth Day of March, 2002

Attest:

JAMES E. ROGAN
Attesting Officer    Director of the United States Patent and Trademark Office